United States Patent
Uwais et al.

(10) Patent No.: US 11,433,422 B2
(45) Date of Patent: Sep. 6, 2022

(54) POLYETHYLENE-CNT-HYDROXYAPATITE COATED MATERIALS

(71) Applicant: KING FAHD UNIVERSITY OF PETROLEUM AND MINERALS, Dhahran (SA)

(72) Inventors: Zahid Ahmed Uwais, Dhahran (SA); Abdul Samad Mohammed, Dhahran (SA); Madhan Kumar, Dhahran (SA); Mohamed Abdrabou Hussein, Dhahran (SA); Nasser Al-Aqeeli, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 419 days.

(21) Appl. No.: 16/568,380

(22) Filed: Sep. 12, 2019

(65) Prior Publication Data

US 2020/0188952 A1 Jun. 18, 2020

Related U.S. Application Data

(60) Provisional application No. 62/780,508, filed on Dec. 17, 2018.

(51) Int. Cl.
| | |
|---|---|
| *B05D 1/06* | (2006.01) |
| *A61F 2/28* | (2006.01) |
| *A61L 27/06* | (2006.01) |
| *A61L 27/32* | (2006.01) |
| *A61L 27/34* | (2006.01) |
| *A61K 6/84* | (2020.01) |
| *B05D 3/14* | (2006.01) |
| *A61L 27/30* | (2006.01) |

(52) U.S. Cl.
CPC ............... *B05D 1/06* (2013.01); *A61L 27/06* (2013.01); *A61L 27/303* (2013.01); *A61L 27/32* (2013.01); *A61L 27/34* (2013.01); *B05D 3/142* (2013.01); *A61L 2420/06* (2013.01); *B05D 2202/35* (2013.01); *B05D 2301/00* (2013.01); *B05D 2518/00* (2013.01)

(58) Field of Classification Search
None
See application file for complete search history.

(56) References Cited

U.S. PATENT DOCUMENTS

| | | | |
|---|---|---|---|
| 7,132,015 B2 | 11/2006 | Wen et al. | |
| 2015/0004209 A1* | 1/2015 | Bose | A61L 27/32 514/769 |
| 2015/0073560 A1* | 3/2015 | Shavit | A61F 2/30767 623/18.11 |
| 2018/0298154 A1 | 10/2018 | Lundorf et al. | |

FOREIGN PATENT DOCUMENTS

| | | |
|---|---|---|
| CN | 101949046 A | 1/2011 |
| CN | 102501444 B | 4/2014 |

OTHER PUBLICATIONS

Prof. Bikramjit Basu, et al., "Electrostatic Spraying of UHMWPE-HA-CNT Biocomposite", Introduction to Biomaterials, Lecture No. 25, Jul. 3, 2012, 28 pages.
Bokai Zhang, et al., "Fabrication of nano-structured HA/CNT coatings on Ti6Al4V by electrophoretic deposition for biomedical applications", Journal of Nanoscience and Nanotechnology, 2010, 6 pages (Abstract only).
Xibo Pei, et al., "Single-walled carbon nanotubes/hydroxyapatite coatings on titanium obtained by electrochemical deposition", Applied Surface Science, vol. 295, Mar. 15, 2004, pp. 71-80 (Abstract Only).
Alireza Abrishamchian, et al., "Preparation and characterization of multi-walled carbon nanotube/hydroxyapatite nanocomposite film dip coated on Ti—6Al—4V by sol-gel method for biomedical applications: An in vitro study", Material Science and Engineering: C, vol. 33, Issue 4, May 2013, pp. 2002-2010 (Abstract only).
S. R. Bakshi, et al., "Synthesis and characterization of multiwalled carbon nanotube reinforced ultra high molecular weight polyethylene composite by electrostatic spraying technique", Composites: Part A, vol. 38, 2007, pp. 2493-2499.
M. Abdul Samad, et al., "Nanocomposite UHMWPE-CNT Polymer Coatings for Boundary Lubrication on Aluminium Substrates", Tribology Letters, vol. 38, No. 3, 2010, pp. 301-311.
Ankur Gupta, et al., "Compression Molded Ultra High Molecular Weight Polyethylene-Hydroxyapatite-Aluminum Oxide-Carbon Nanotube Hybrid Composites for Hard Tissue Replacement", Journal of Materials Science & Technology, vol. 29, Issue 6, Jun. 2013, pp. 514-522.
A. M. Cunha, et al., "The Influence of Processing Conditions on the Mechanical Behaviour of UHMWPE/HA and PMMA/HA Composites", Advances in Materials Science and Implant Orthopedic Surgery, 1995, pp. 163-176.
S.L. Ruan, et al., "Toughening high performance ultrahigh molecular weight polyethylene using multiwalled carbon nanotubes", Polymer, vol. 44, 2003, pp. 5643-5654.
Y. Chen, et al., "Carbon nanotube reinforced hydroxyapatite composite coatings produced through laser surface alloying", Carbon, vol. 44, 2006, pp. 37-45.
Y. Chen, et al., Wear studies of hydroxyapatite composite coating reinforced by carbon nanotubes, Carbon, vol. 45, 2007, pp. 998-1004.

(Continued)

*Primary Examiner* — Sheeba Ahmed
(74) *Attorney, Agent, or Firm* — Oblon, McClelland, Maier & Neustadt, L.L.P.

(57) ABSTRACT

A biocompatible polymer hybrid nanocomposite coating on a surface of a substrate, such as titanium and its alloys. The coating can be achieved by an electrostatic spray coating, preferably using ultra-high molecular weight polyethylene (UHMWPE) as a matrix for the coating. For example, up to 2.95 wt. % carbon nanotubes can be used as reinforcement, as can up to 4.95 wt. % hydroxyapatite. A dispersion of CNTs and HA in the coating is substantially uniform. The tribological performance of such coatings include high hardness, improved scratch resistance, excellent wear resistance, and corrosion resistance compared to pure UHMWPE coatings.

15 Claims, 52 Drawing Sheets

(56) References Cited

OTHER PUBLICATIONS

Joana Reis, et al., Carbon Nanotubes—Interactions with Biological Systems, Carbon Nanotubes: Growth and Applications, Chapter 19, Aug. 9, 2011, pp. 476-492.
C.T. Kwok, et al., "Characterization and corrosion behavior of hydroxyapatite coatings on Ti6Al4V fabricated by electrophoretic deposition", Applied Surface Science, vol. 255, 2009, pp. 6736-6744.
Shilun Ruan, et al., "Ultra-strong gel-spun UHMWPE fibers reinforced using multiwalled carbon nanotubes", Polymer, vol. 47, 2006, pp. 1604-1611.
Kantesh Balani, et al., "Tribological behavior of plasma-sprayed carbon nanotube-reinforced hydroxyapatite coating in physiological solution", Acta Biomaterialia, vol. 3, 2007, pp. 944-951.
Yang Xue, et al., "Tribological behaviour of UHMWPE/HDPE blends reinforced with multi-wall carbon nanotubes", Polymer Testing, vol. 25, 2006, pp. 221-229.
Debrupa Lahiri, et al., "Carbon nanotube reinforced hydroxyapatite composite for orthopedic application: A review", Materials Science and Engineering C, vol. 32, 2012, pp. 1727-1758.
Bharat Panjwani, et al., "Tribological characterization of a biocompatible thin film of UHMWPE on Ti6Al4V and the effects of PFPE as top lubricating layer", Journal of the Mechanical Behavior of Biomedical Materials, vol. 4, 2011, pp. 953-960.
Shekhar Nath, et al., "Tribological investigation of novel HDPE-HAp-$Al_2O_3$ hybrid biocomposites against steel under dry and simulated body fluid condition", Journal of Biomedical Materials Research Part A, 2017, pp. 191-208.
I. V. Knets, et al., "Ultrahigh-Molecular Weight Polyethylene and Hydroxylapatite-Based Materials for Replacement of Bone Tissue", Mechanics of Composite Materials, vol. 29, Issue 2, Mar.-Apr. 1993, pp. 181-189.
Juan C. Baena, et al., "Wear Performance of UHMWPE and Reinforced UHMWPE Composites in Arthroplasty Applications: A Review", Lubricants, vol. 3, 2015, pp. 413-436.
Z. Wei, et al., "A study of the tribological behavior of carbon-nanotube-reinforced ultrahigh molecular weight polyethylene composites", Surface and Interface Analysis, vol. 38, 2006, pp. 883-886.
Kantesh Balani, et al., "Plasma-sprayed carbon nanotube reinforced hydroxyapatite coatings and their interaction with human osteoblasts in vitro", Biomaterials, vol. 28, 2007, pp. 618-624.
Liming Fang, et al., "Processing of hydroxyapatite reinforced ultrahigh molecular weight polyethylene for biomedical applications", Biomaterials, vol. 26, 2005, pp. 3471-3478.
Yanping Wang, et al., "Study on the preparation and characterization of ultra-high molecular weight polyethylene-carbon nanotubes composite fiber", Composites Science and Technology, vol. 65, 2005, pp. 793-797.
M.J. Abden, et al., "Pressureless sintering and mechanical properties of hydroxyapatite/functionalized multi-walled carbon nanotube composite", Materials Science and Engineering C, vol. 67, 2016, pp. 418-424.
Liming Fang, et al., "Processing and mechanical properties of HA/UHMWPE nanocomposites", Biomaterials, vol. 27, 2006, pp. 3701-3707.

Bikramjit Basu, et al., "Processing, Tensile, and Fracture Properties of Injection Molded Hdpe-$Al_2O_3$-Hap Hybrid Composites", Journal of Applied Polymer Science, vol. 121, 2011, pp. 2500-2511.
J.L. Xu, et al., "Preparation and characterization of a novel hydroxyapatite/carbon nanotubes composite and its interaction with osteoblast-like cells", Materials Science and Engineering C, vol. 29, 2009, pp. 44-49.
Qinggang Tan, et al., "Mineralization of surfactant functionalized multi-walled carbon nanotubes (MWNTs) to prepare hydroxyapatite/MWNTs nanohybrid", Applied Surface Science, vol. 255, 2009, pp. 7036-7039.
Ankur Gupta, et al., "Dependence of Protein Adsorption on Wetting Behavior of UHMWPE-HA-$Al_2O_3$-CNT Hybrid Biocomposites", JOM, vol. 64, Issue 4, Apr. 2012, pp. 506-513.
Catherine Kealley, et al., "Development of carbon nanotube-reinforced hydroxyapatite bioceramics", Physica B, vols. 385-386, 2006, pp. 496-498.
M. Abdul Samad, et al., "Dry sliding and boundary lubrication performance of a UHMWPE/CNTs nanocomposite coating on steel substrates at elevated temperatures", Wear, vol. 270, 2011, pp. 395-402.
Yeong-Seokzoo, et al., "Effect of carbon nanotube addition on tribological behavior of UHMWPE", Tribology Letters, vol. 16, No. 4, May 2004, pp. 305-309.
M. Abdul Samad, et al., "Effects of counterface material and UV radiation on the tribological performance of a UHMWPE/CNT nanocomposite coating on steel substrates", Wear, vol. 271, 2011, pp. 2759-2765.
Cengiz Kaya, "Electrophoretic deposition of carbon nanotube-reinforced hydroxyapatite bioactive layers on Ti—6Al—4V alloys for biomedical applications", Ceramics International, vol. 34, 2008, pp. 1843-1847.
Yu Bai, et al., "Electrophoretic deposition of carbon nanotubes-hydroxyapatite nanocomposites on titanium substrate", Materials Science and Engineering C, vol. 30, 2010, pp. 1043-1049.
Ming Li, et al., "Graphene oxide/hydroxyapatite composite coatings fabricated by electrophoretic nanotechnology for biological applications", Carbon, vol. 67, 2014, pp. 185-197.
Byung-Dong Hahn, et al., "Mechanical and in vitro biological performances of hydroxyapatite-carbon nanotube composite coatings deposited on Ti by aerosol deposition", Acta Biomaterialia, vol. 5, 2009, pp. 3205-3214.
Yao Chen, et al., "Laser-surface-alloyed carbon nanotubes reinforced hydroxyapatite composite coatings", Applied Physics Letters, vol. 86, 2005, pp. 251905-1-251905-3.
M. Abdul Samad, et al., "Mechanical, thermal and tribological characterization of a UHMWPE film reinforced with carbon nanotubes coated on steel", Tribology International, vol. 44, 2011, pp. 1932-1941.
Muhammad Umar Azam, et al., "UHMWPE hybrid nanocomposite coating reinforced with nanoclay and carbon nanotubes for tribological applications under water with/without abrasives", Tribology International, vol. 124, 2018, pp. 145-155.
Muhammad Umar Azam, et al., "Tribological Evaluation of a UHMWPE Hybrid Nanocomposite Coating Reinforced With Nanoclay and Carbon Nanotubes Under Dry Conditions", Journal of Tribology, vol. 140, No. 5, Sep. 2018, pp. 051304-1-051304-9.
Abdul Samad Mohammed, "UHMWPE Nanocomposite Coatings Reinforced with Alumina ($Al_2O_3$) Nanoparticles for Tribological Applications", Coatings, vol. 8, No. 280, 2018, pp. 1-14.

\* cited by examiner

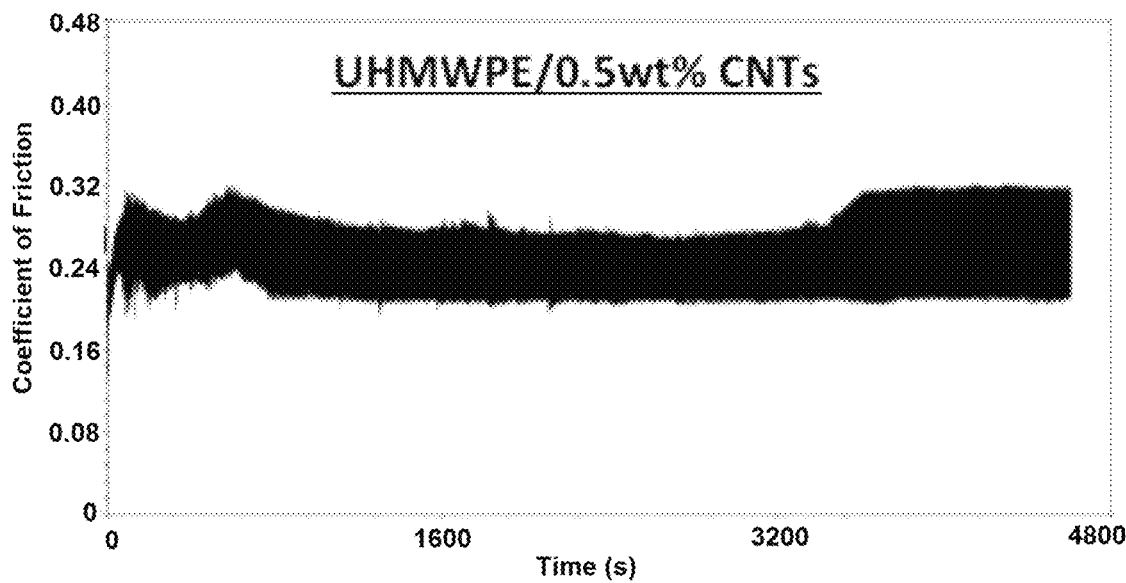
Fig. 4B
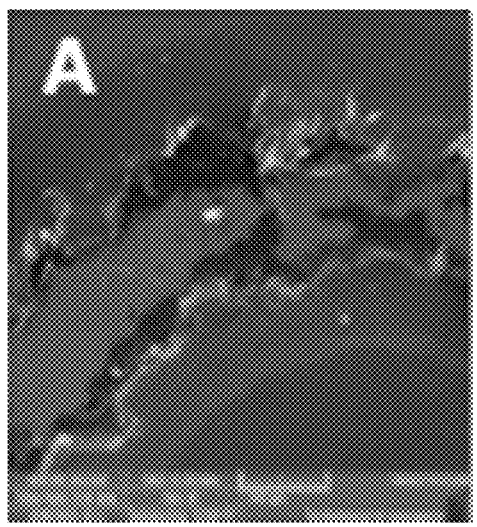 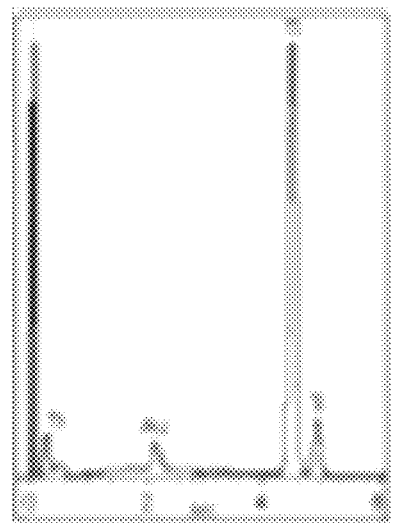
Fig. 4C              Fig. 4D

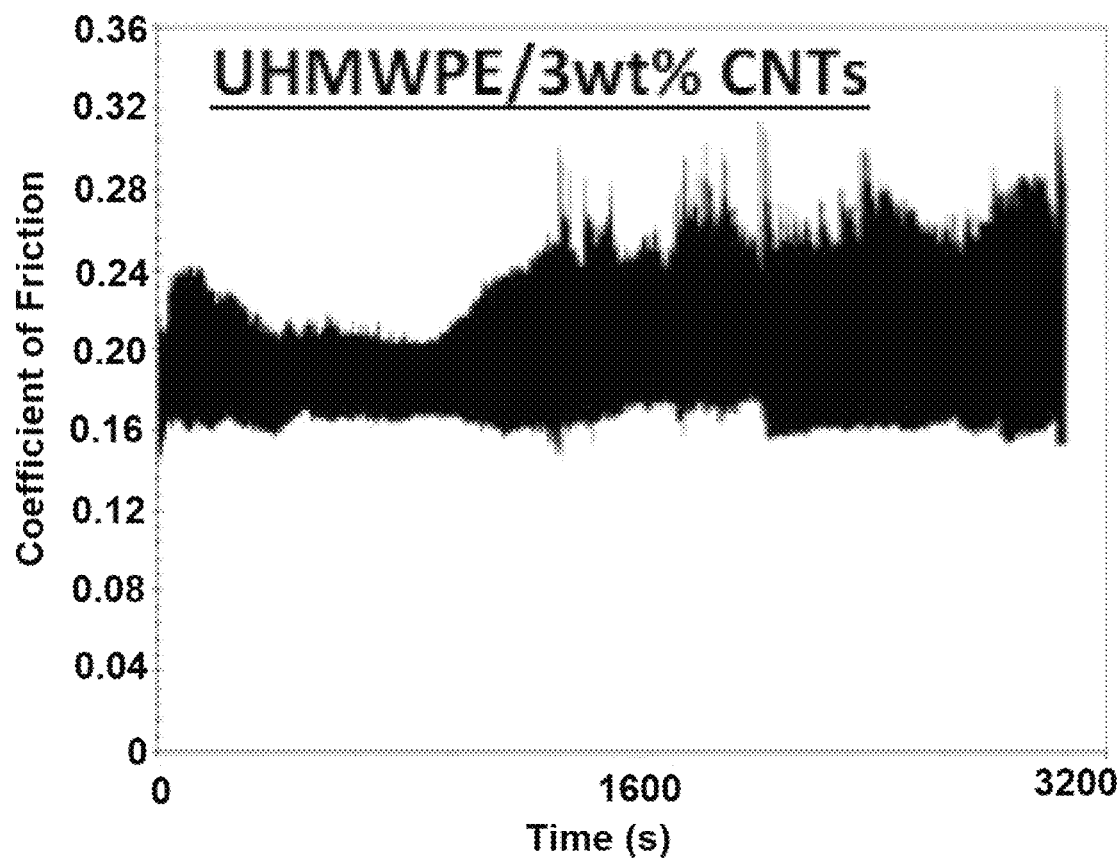
Fig. 4H
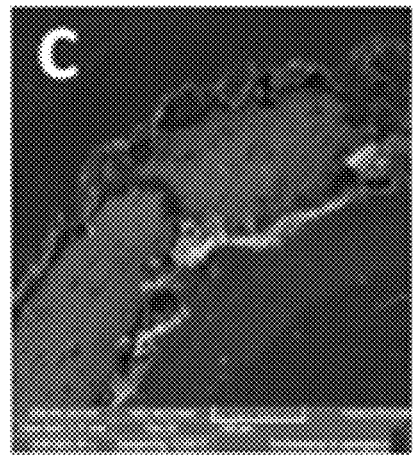 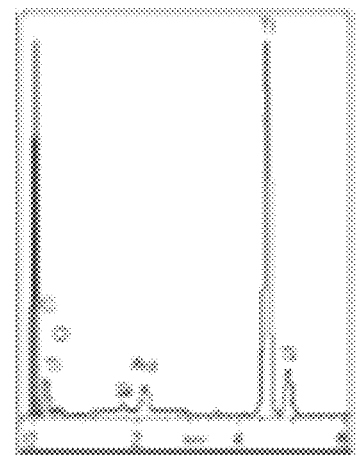
Fig. 4I  Fig. 4J

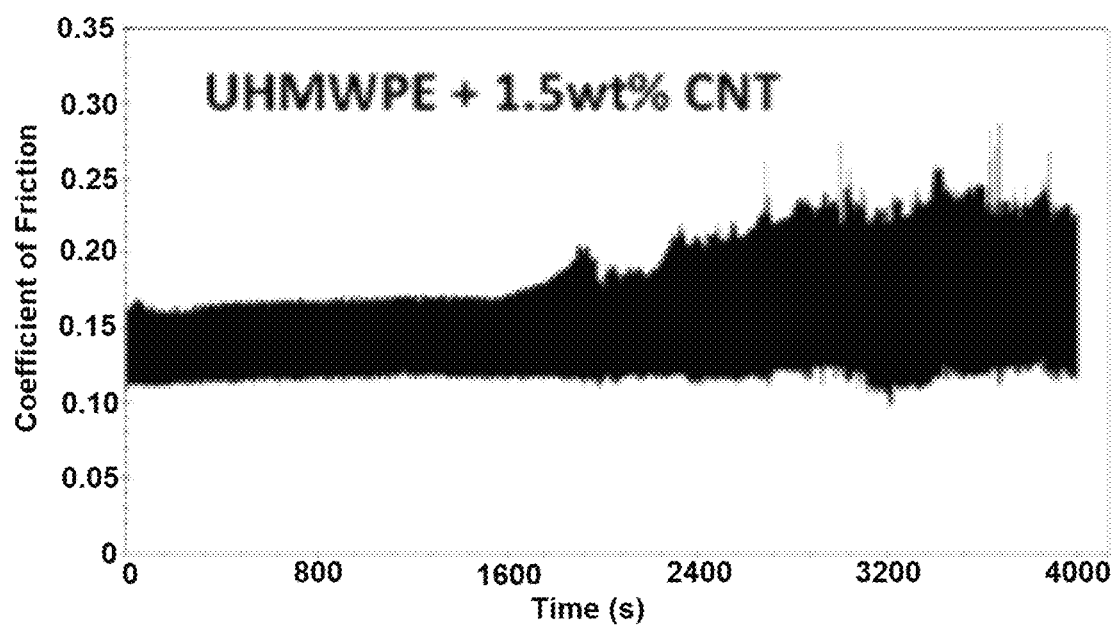
Fig. 5B
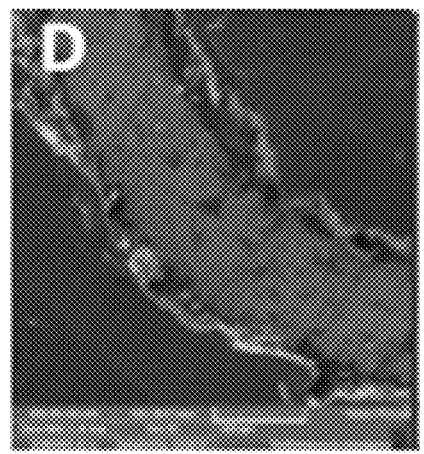 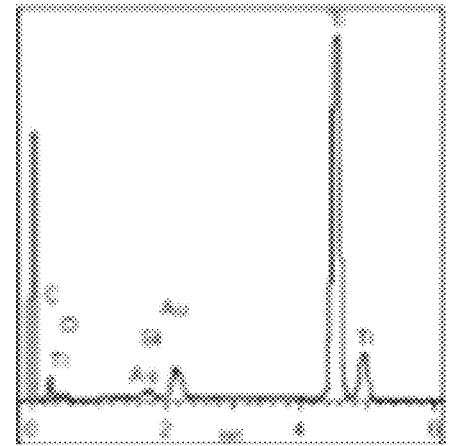
Fig. 5C        Fig. 5D

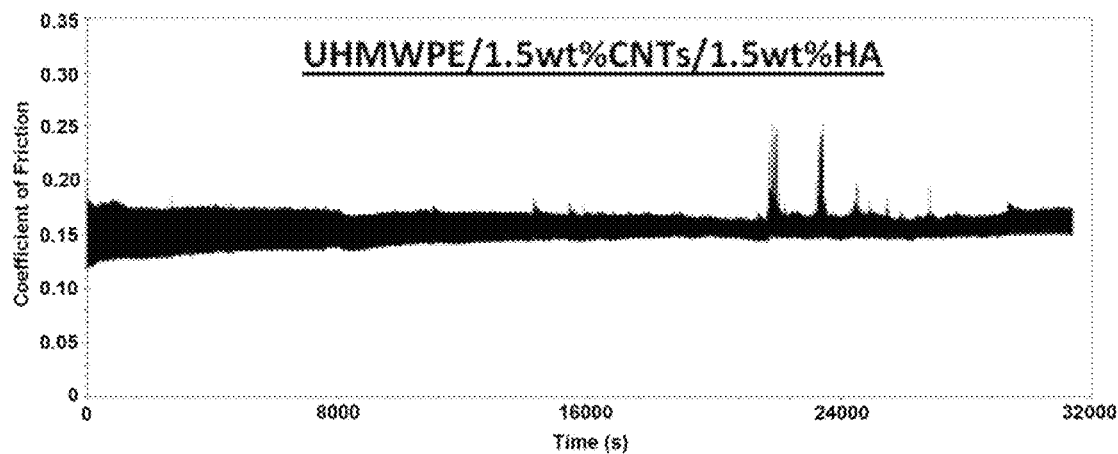
Fig. 9E
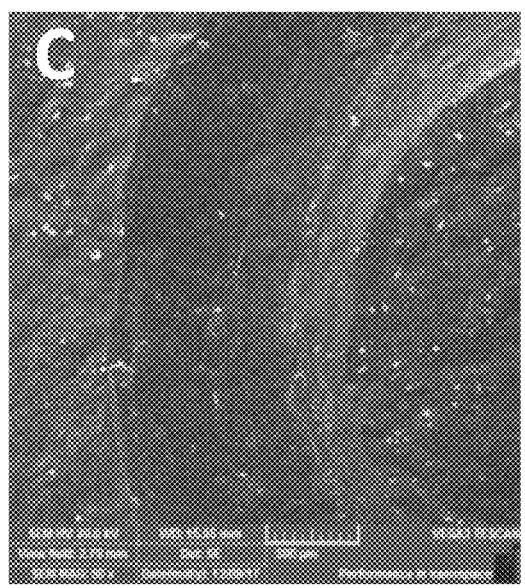 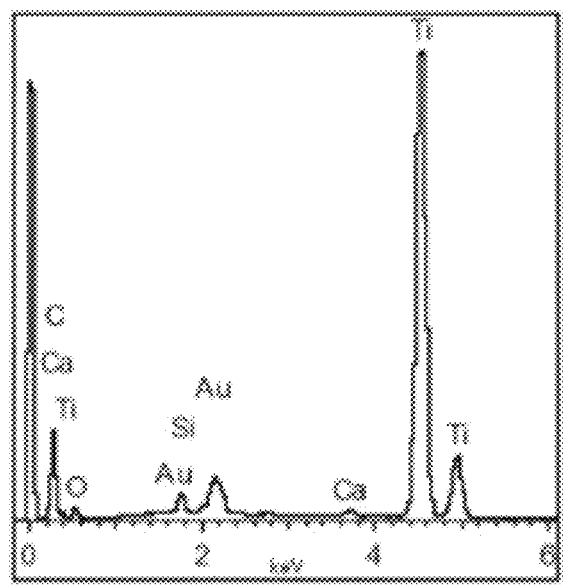
Fig. 9F　　　　　Fig. 9G

POLYETHYLENE-CNT-HYDROXYAPATITE COATED MATERIALS

CROSS-REFERENCE TO RELATED APPLICATIONS

The present application claims priority to U.S. provisional application 62/780,508, filed on Dec. 17, 2018, which is incorporated by reference herein in its entirety.

STATEMENT OF ACKNOWLEDGMENT

The inventors gratefully acknowledge the financial support funding this work from the King Abdulaziz City for Science and Technology (KACST) in the Science & Technology Unit at King Fahd University of Petroleum & Minerals (KFUPM) through project #15-ADV4632-04 as part of the National Science, Technology, and Innovation Plan.

STATEMENT REGARDING PRIOR DISCLOSURES BY THE INVENTOR(S)

Aspects of the application are described in the master's thesis of inventor, Zahid Ahmad UWATS, at King Fahd University of Petroleum and Minerals entitled "Tribological Characterization of a Novel UHMWPE Hybrid Nanocomposite Coating for Biomedical Applications" (Uwais Thesis), submitted in December of 2017, an abstract of which was published on May 2, 2018. The Uwais Thesis is incorporated by reference herein in its entirety.

BACKGROUND OF THE INVENTION

Field of the Invention

The present disclosure relates to surface coatings and layered arrangements, particularly for biological, veterinary, and/or human medicinal applications, as well as to methods of making and using such coatings and arrangements. In particular, the coatings may comprise particular amounts of hydroxyapatite (HA), e.g., 0.5 to 5 wt. %, and carbon nanotubes (CNTs), e.g., 0.5 to 2.5 wt. %, in a polymer matrix including a polyolefin, such as a polyethylene (PE), particularly an ultra high molecular weight polyethylene (UHMWPE).

Description of the Related Art

Titanium and its alloys have been used in various biomedical implants for replacing damaged hard tissue since the 1970s. A few examples of titanium used in biomedical applications include pacemakers, artificial hearts, bone plates, cornea back plates, artificial hip joints, artificial knee joints, screws for fracture fixation, cardiac valve prostheses, and dental and orthopedic implants, as detailed in *Arab. J. Sci. Eng.* 2017, 42, 4493-4512, which is incorporated by reference herein in its entirety.

The low modulus, excellent biocompatibility, and corrosion resistance of titanium alloys make them a good choice for orthopedic materials compared to stainless steel and cobalt alloys. Thus, numerous devices have been made from titanium alloys for biomedical applications. Nevertheless, certain parameters of titanium alloys, such as poor tribological properties, low abrasive resistance, and oxide layer mechanical instability have limited the successful implementation of titanium alloys in certain applications.

These negative factors of titanium alloys may affect the long-term success of the implant and could be related to aseptic loosening and osteolysis, and potentially failing to meet all the clinical requirements. Several surface modification technologies applicable to titanium and titanium alloys have been investigated, as described in *Proc. Inst. Mech. Eng. J. —J. Eng. Tribol.* 2009, 223(3), 311-316, and *Mater. Sci. Eng. Reports* 2004, 47, 49-121, each of which is incorporated by reference herein in its entirety.

Surface properties of titanium and its alloys can be enhanced using one or more appropriate highly wear resistant coatings, such as diamond like carbon (DLC), hydroxyapatite, titanium nitride, micronite, etc., and/or surface treatment techniques such, as plasma immersed ion implantation, thermal oxidation, nitrogen ion implantation, carburization, etc. Materials are usually deposited by dip coating, spin coating, electrostatic powder coating, plasma spray coating, laser deposition, etc., as described in *Appl. Surf Sci.* 2009, 255, 4082-4086, *Acta Biomater.* 2007, 3, 944-951, *Surf. Coatings Techn.* 2014, 258, 1159-1170, *Surf Coatings Techn.* 2007, 201, 6847-6850, *J. Shanghai Univ.* (English Edition) 2005, 9(2), 164-171, *Proc. Inst. Mech. Eng. J. —J. Eng. Tribol.* 2009, 223(3), 311-316, *Appl. Surf Sci.* 2018, 449, 181-185, *J. Alloys Compounds* 2009, 473(1-2), 394-400, *Appl. Surf Sci.* 2018, 441, 187-193, *J. Biomed. Mater. Res.* 2004, 69A(2), 279-285, *Appl. Surf Sci.* 2018, 434, 1064-1073, each of which is incorporated by reference herein in its entirety.

Polymer coatings have been increasingly used in engineering applications due to their remarkable properties such as excellent corrosion and wear resistance, low cost, self-lubricating properties, and the ability to coat onto complex shapes, for example, as described in *Surf Coatings Techn.* 2008, 202(15), 3698-3708, which is incorporated by reference herein in its entirety. To be used in biomedical applications, polymer coatings should not only have good mechanical and tribological properties, but should also be biocompatible. One such polymer is ultra-high molecular weight polyethylene (UHMWPE).

Since 1962, when UHMWPE was introduced commercially, UHMWPE has been used in several biomedical applications due to its high strength and bio-compatibility. In addition, its high stiffness and strength make UHMWPE useful as a component of structural materials and in fiber production, as described in *JOM* 2007, 59(7), 50-53, which is incorporated by reference herein in its entirety. The outstanding properties of UHMWPE, such as abrasive resistance, notched impact strength, and low coefficient of friction, make UHMWPE feasible for use in highly stressed part for instance in total joint replacement, UHMWPE is still commercially used for manufacturing cups and tibial inserts, as described in *J. Biomed. Mater. Res. A* 2006, 78A, 473-480, *Tribol. Int.* 2016, 96, 349-360, and Kurtz, S. M. (ed) *UHMWPE Biomaterials Handbook* $3^{rd}$ Ed., Elsevier: New York, 2016, each of which is incorporated by reference herein in its entirety.

Despite its excellent tribological properties, the use of UHMWPE in biomedical applications has been hindered due to its low load-bearing capacity, causing the generation of wear debris particles and leading to complications such as osteolytic lesions and radiographic loosening. Addressing these issues has been the focus of considerable scientific research, as described in *J. Orthop. Res.* 2002, 20, 1038-1041, and *J. Biomed. Mater. Res.* 2000, 53, 100-10, each of which is incorporated by reference herein in its entirety. Reinforcing the UHMWPE polymer matrix with carbon nanotubes (CNTs) has been proposed as a possible solution to overcome the low load-bearing capacity issue in UHMWPE, as described in *Wear* 2011, 270, 395-402, which is incorporated by reference herein in its entirety.

Carbon nanotubes (CNT's) are cylinders of graphite sheets either in the form of multi-walled (MW) or single-walled (SW) assemblies. Several studies have shown that the reinforcement of polymer matrices with CNTs in bulk form and in coating form can result in improved hardness and wear resistance, owing to the high tensile strength, high stiffness, and excellent electrical and thermal properties of CNTs. Such reinforcement applications are described in *Lubricants* 2015, 3(2), 413-436, *Surf. Coat. Techn.* 2011, 206, 759-766, *Appl. Phys. A* 1999, 69(3), 255-260, and Dresselhaus, M. S., Dresselhaus G., Avouris P. (eds) *Carbon Nanotubes*, Topics in Applied Physics Vol. 80, Springer: Berlin, 2001, each of which is incorporated by reference herein in its entirety.

Further approaches to improving the biocompatibility of the UHMWPE include adding various components such as graphene oxide, graphene nano-platelet, zirconium particles, etc., as described in *Eur. Polym. J.* 2012, 48, 1026-1033, *ACS Appl. Mater. Interf.* 2012, 4, 2234-2241, Wear 2009, 267, 710-717, each of which is incorporated by reference herein in its entirety. Hydroxyapatite (HA), $Ca_{10}(PO_4)_6(OH)_2$, is a biomaterial present in bone and teeth, which has gained interest. The biocompatibility and bioactivity of hydroxyapatite promote osteoblasts, therefore hydroxyapatite coatings have been used in several biomedical applications such as dental implants, skeletal implants, bone repair scaffolds, body insert material, etc., as detailed in *Biomaterials* 2007, 28, 618-624, which is incorporated by reference herein in its entirety.

Recently, the development of hydroxyapatite (HA)-reinforced coatings, such as magnesium oxide/HA, titania/HA, strontium/HA, polycaprolactone/HA, nanodiamond/HA, etc., have been prepared, as described in *Mater. Lett.* 2012, 68, 439-442, *Biomaterials* 2001, 22, 1425-1431, *Biomaterials* 2004, 25, 4393-4403, *Biomaterials* 2010, 31, 9006-9014, *Biomaterials* 2004, 25, 1279-1287, *Appl. Surf. Sci.* 2018, 439, 60-65, each of which is incorporated by reference herein in its entirety. When deposited on titanium and other biomaterials, HA can enhance biocompatibility while preserving the mechanical properties of the substrate.

However, little research has been conducted into the feasibility of using two (or more) individual reinforcements together, to explore whether a synergistic effect can be achieved. Certain efforts and investigations in the art warrant discussion.

CN 102501444 B by Li et al. (Li) discloses a $TiO_2$ nanotube array-carbon nanotube (CNT)-hydroxyapatite (HA) biological composite coating, prepared by uniformly coating CNTs and HA on a titanium substrate with a $TiO_2$ nanotube array on the surface, wherein the uniformly arranged $TiO_2$ nanotube array has a tube diameter of 100±20 nm, the HA is 70 to 99.9 wt. %, and the CNTs are 0.1 to 30 wt. %. Li's coating has good mechanical properties, biocompatibility, has the interface binding strength of 31 to 48 MPa, and can be used for surface modification of titanium and titanium alloy to prolong the service life of titanium and titanium alloy in a human body. Li does not disclose using a polyolefin, nor PE or UHMWPE in its coating, much less by electrostatic spray coating a powder comprising the UHMWPE, CNT, and HA.

CN 101949046 A by Guo et al. (Guo) discloses a method for preparing a $CO_3^{2-}$-HA/CNT composite coating, involving: (1) depositing $CaCO_3$ (containing) powder and CNTs on the surface of a metal matrix to obtain a $CaCO_3$ powder/CNT coating by electrophoretic deposition; and (2) treating the $CaCO_3$ powder/CNT coating with a $H_3PO_4$ buffer solution, and converting the treated solution into the $CaCO_3$ powder/CNT composite coating. Guo's method is executed at STP and is suitable for preparing implants of various complicated shapes. Guo does not disclose any polymers for its coating, much less PE or UHMWPE, nor the even application of a surface coating on a Ti-containing substrate by electrostatic spray. Moreover, Guo requires $CaCO_3$ for its coating.

US 2018/0298154 A1 by Lundorf et al. (Lundorf) discloses a composite material, where the matrix material and the additive are held together by covalently or non-covalently bound ligands. Lundorf has a linker unit between matrix and additive, Ligand1-LinkerL-Ligand 2, wherein Ligand1 and Ligand2 are a bond or a chemical entity that is capable of binding covalently or non-covalently to a structural entity, such as a polymer matrix or the additive, such as CNT, graphene, carbon nanofiber, etc., and LinkerL is a chemical bond or entity that links Ligand1 and Ligand2. While Lundorf mentions polymers, such as PE, within its vast array of generally described materials, Lundorf's arrangement requires a linker, fullerene, and amino acids.

U.S. Pat. No. 7,132,015 to Wen et al. (Wen) discloses dental enamel inspired materials for biomedical and dental applications. Wen's materials are apatite-like calcium phosphate complexes and may comprise apatite, octacalcium phosphate crystals, or mixtures thereof. Wens' materials may be mixtures of crystals of apatite and its precursor, octacalcium phosphate, nucleated on a titanium surface, prepared so as to form biological apatite similar to that in natural bone and teeth. Wen's materials may be prepared by placing a titanium substrate in a supersaturated calcifying solution containing native or purified recombinant amelogenins. Wen's materials may be used in dental tissue replacement, orthopeadic implants for bone repair, and coatings for improving the biocompatibility and bone regeneration capability of currently available implants/devices. Wen does not use a polyolefin matrix for its coatings, instead at most coating such materials with HA, nor coating by electrostatic spray.

The lecture from the Indian Institutes of Technology (Bombay, Delhi, Kanpur, Kharagpur, Madras, Guwahati and Roorkee) and the Indian Institute of Science, by Basu, B.; and Balani, K. "Electrostatic Spraying of UHMWPE-HA-CNT Biocomposite" National Programme on Technology Enhanced Learning (NPTEL), Computers and Writing Conference, 23 May 2003, Indian Institute of Technology, Kanpur, lecture 25 (Basu) discloses electrostatic spraying UHMWPE comprising 5% HA and 2, 4, or 5 wt % CNTs onto a substrate, such as titanium. Basu teaches ball milling rather than sonicating/mechanical mixing, and no plasma pretreatment or pre-heating. Basu's ideal coating is 40-50 μm thick, and generally not thicker than 200 μm.

*J. Nanosci. Nanotechn.* 2011, 11(12), 10740-10745(6) by Zhang et al. (Zhang) discloses improving bone bioactivity and osteointegration of metallic implants, by depositing nanostructured HA coatings via cathodic electrophoretic deposition (EPD) on titanium alloy Ti6Al4V followed by sintering at 800° C. Zhang uses nano-sized HA powder for dense coatings, as well as multiwalled carbon nanotubes (CNTs) to reinforce the HA coating and enhance mechanical strength. Zhang describes CNT contents of 4 to 25% on Ti6Al4V, and Zhang's HA and HA/CNT coatings had a thickness of about 10 μm, with adhesion strength higher than that of plasma sprayed HA coating. Zhang does not teach using a polymer, much less a polyolefin or PE, in its coating, and Zhang teaches CNT contents above 4 wt. %.

*Appl. Surf Sci.* 2014, 295, 71-80 by Pei et al. (Pei) discloses single-walled carbon nanotube/hydroxyapatite (SWNT/HA) composite coatings made by electrochemical deposition. Pei incorporates different concentrations of SWNTs into the apatite coating by adding functionalized SWNTs into the electrolyte, and coating titanium. Pei teaches potential applications in biomaterials, especially metal implants. However, Pei does not use a polymer matrix in its coating, nor electrospraying.

*Mater. Sci Eng.* C 2013, 33(4), 2002-2010 by Abrishamchian et al. (Abrishamchian) discloses introducing multiwalled carbon nanotubes (MWCNTs) into an HA matrix and dip coating the HA-MWCNT nanocomposite on titanium alloy (Ti-6Al-4V) plate in a sol-gel process. Abrishamchian describes HA/MWCNT coatings with different MWCNT weight percentages, and teaches that 0.5 and 1 wt. % MWCNT concentrations improved the mechanical properties of the coatings. Abrishamchian does not use a polymer matrix in its coating, nor electrospraying.

*Composites A* 2007, 38, 2493-2499 by Bakshi et al. (Bakshi) discloses multiwalled carbon nanotube (MWNT) reinforced UHMWPE composite films were prepared by electrostatic spraying followed by consolidation. Bakshi does not use HA in its coatings.

*Tribol. Lett.* 2010, 38(3), 301-311 by Samad et al. (Samad) discloses UHMWPE films with 0.1 wt. % SWCNTs coated on Al substrates under dry and base oil (without any additives)-lubricated conditions. Samad does not use HA in its coatings.

*J. Mater. Sci. Techn.* 2013, 29(6), 514-522 by Gupta et al. (Gupta) discloses UHMWPE based polymer composites synergistic reinforced with HA, $Al_2O_3$, and CNTs using compression molding. Gupta does not disclose electrospraying, nor particular ranges of HA and CNT, and Gupta requires aluminum oxide in its coatings.

In light of the above, a need remains for polymeric composite coatings useful in biotechnological applications, particularly for implants and implant coatings, such as coatings using a polyethylene matrix, carbon nanotubes (CNTs), and hydroxyapatite (HA), and methods of making such coatings, and bio-compatible medical devices.

SUMMARY OF THE INVENTION

Aspects of the invention provide articles, comprising: a substrate; and directly contacting the substrate, a coating comprising, relative to total coating weight, 0.5 to 4.75 wt. % hydroxyapatite and 0.5 to 2.75 wt. % carbon nanotubes in a polymer matrix comprising at least 75 wt. % ultra high molecular weight polyethylene. Such coatings may have a thickness of between 60 and 1000 µm, and/or be modified by one or more of the features described herein in any permutation, particularly the following.

The substrate may be metallic, e.g., comprising elemental titanium, gold, cobalt, tantalum, chromium, nickel, and/or stainless steel, and/or may comprise at least 75 wt. % pure titanium or Ti6Al4V, based upon total substrate weight. The substrate may be pure titanium or Ti6Al4V.

The coating may comprise the carbon nanotubes in a range of from 1 to 2 wt. % and/or the hydroxyapatite in a range of from 2.5 to 3.5 wt. %. The coating may comprise the ultra high molecular weight polyethylene in an amount of at least 97.5 wt. %, relative to all polymer content in the coating. The ultra high molecular weight polyethylene may have a Mn of at least 1,000,000 g/mol. The coating may have a thickness of at least 100 µm. At least 95 wt. % of the hydroxyapatite and carbon nanotubes, relative total weights thereof in the coating, may be completely surrounded by the polymer matrix. The coating may be configured to directly contact animal tissue in operation.

The carbon nanotubes may have an outer diameter in a range of from 40 to 60 nm, a length in a range of from 1 to 2 µm, and/or a specific surface area in a range of from 60 to 70 $m^2/g$. The carbon nanotubes may be multi-walled.

Inventive articles may have a Vickers hardness on a surface of the coating opposite the substrate of at least 8.

Aspects of the invention include methods of preparing coated substrates in any permutation described herein. Such methods may comprise: pretreating the substrate including contacting the substrate with plasma, to obtain a pretreated substrate; and electrospraying onto the pretreated substrate a solid comprising at least 75 wt. % of ultra high molecular weight polyethylene, 0.5 to 4.75 wt. % of hydroxyapatite, and 0.5 to 2.75 wt. % of carbon nanotubes, to obtain a coated substrate. The pretreating may further comprise, after the contacting, heating the substrate to at least 140° C., to obtain the pretreated substrate. Such methods may further comprise, after the electrospraying: heating the coated substrate to at least 140° C.

Aspects of the invention comprise methods for improving the wear resistance of a coated substrate in any inventive permutation described herein, the method comprising coating a substrate with a mixture comprising at least 50 wt. % UHMWPE and between 0.25 and 2.75 wt. % carbon nanotubes and 0.25 to 4.75 wt. % hydroxyapatite, a remainder comprising polymer material.

Aspects of the invention provide methods of improving the uniformity of the distribution of hydroxyapatite and carbon nanotube additives in a coating, the method comprising: combining 0.5 to 4.75 wt. % hydroxyapatite, 0.5 to 2.75 wt. % carbon nanotubes, and at least 75 wt. % ultra high molecular weight polyethylene to obtain a coating precursor mixture; mechanically agitating the coating precursor mixture, to obtain an agitated mixture; and applying the agitated mixture to a preheated substrate by electrostatic spray coating a powder, wherein the preheated substrate is preheated to a temperature of at least the melting point of the ultra high molecular weight polyethylene.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4B shows a coefficient of friction (COF) plot of a substrate coated with UHMWPE comprising 0.5 wt. % of CNTs after a wear test conducted at a normal load of 12 N and a sliding velocity of 0.1 m/s for 50,000 cycles (6276 seconds);

FIG. 4C shows an SEM image of the wear track from the coated substrate from FIG. 4B;

FIG. 4D shows an EDX spectrum of the region of the wear track from the coated substrate from FIG. 4B;

FIG. 4H shows a COF plot of a substrate coated with UHMWPE comprising 3 wt. % of CNTs after a wear test conducted at a normal load of 12 N and a sliding velocity of 0.1 m/s for 50,000 cycles (6276 seconds);

FIG. 4I shows an SEM image of the wear track from the coated substrate from FIG. 4G;

FIG. 4J shows an EDX spectrum of the region of the wear track from the coated substrate from FIG. 4G;

FIG. 5B shows a COF plot of the article akin to that of FIG. 4E, wherein the wear test uses a normal load of 15 N, rather than 12 N;

FIG. 5C shows an SEM image of the wear track from the coated substrate from FIG. 5B;

FIG. 5D shows an EDX spectrum of the region of the wear track from the coated substrate from FIG. 5B;

FIG. 9E to 9G show the COF graph, SEM image of the wear track, and EDX spectrum of a sample of the same type as shown in FIG. 8C wherein the wear test is conducted for 250,000 cycles (31380 seconds);

DETAILED DESCRIPTION OF THE PREFERRED EMBODIMENTS

Figure 1:
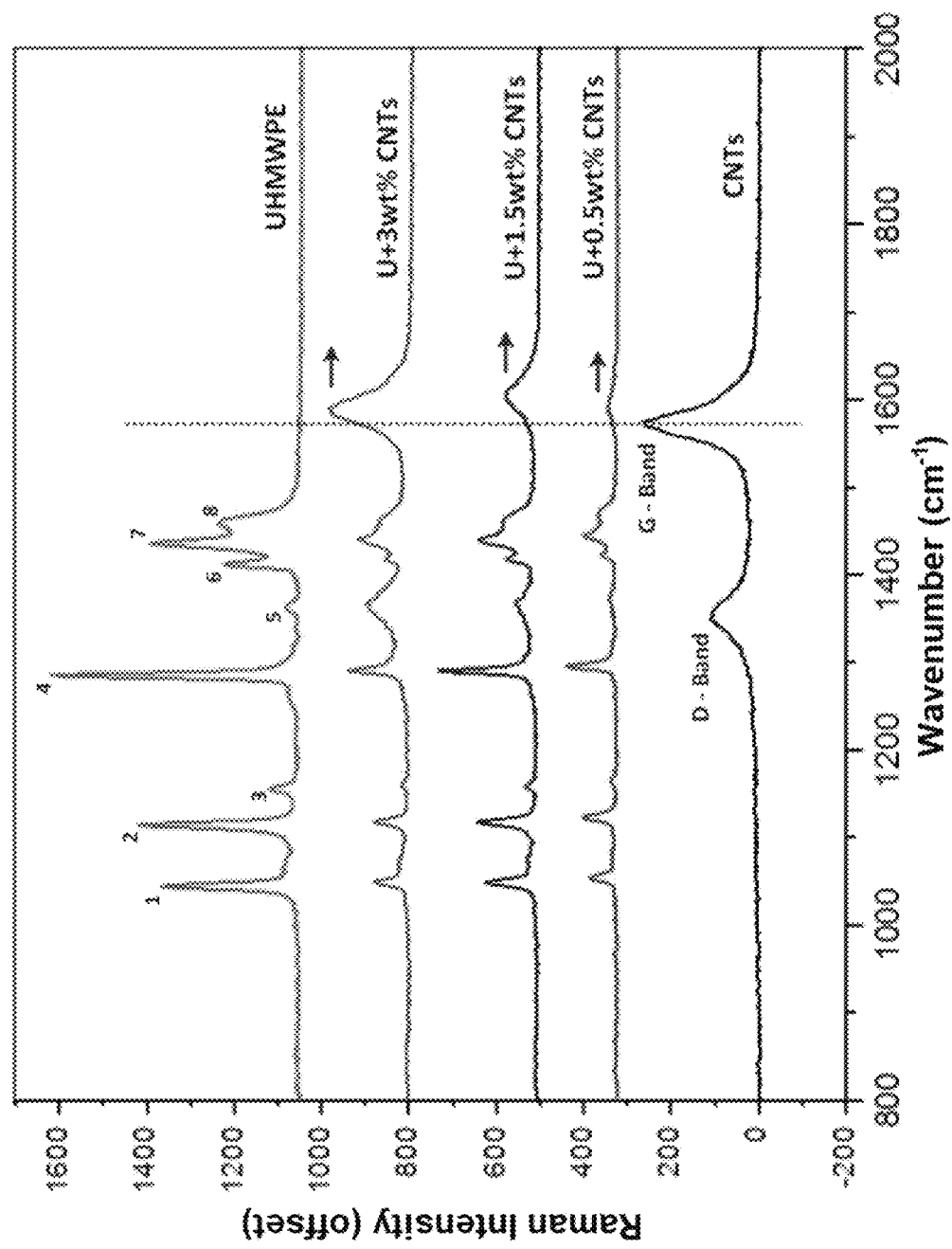
FIG. 1 shows the Raman spectra peaks of pure ultra high molecular weight polyethylene (UHMWPE), UHMWPE including 0.5 wt. % carbon nanotubes (CNTs), UHMWPE including 1.5 wt. % CNTs, UHMWPE including 3 wt. % CNTs, and CNTs.

Aspects of the invention provide articles, comprising: a substrate; and directly contacting the substrate, a coating comprising, relative to total coating weight, 0.5 to 4.75 wt. % hydroxyapatite (e.g., at least 0.5, 0.6, 0.67, 0.75, 0.8, 0.85, 0.9, 0.95, 1, 1.1, 1.2, 1.25, 1.33, 1.4, 1.45, 1.5, 1.75, 2, or 2.25 wt. % HA and/or up to 4.75, 4.67, 4.6, 4.5, 4.33, 4.25, 4.15, 4.1, 4.05, 4, 3.95, 3.9, 3.85, 3.8, 3.75, 3.67, 3.6, 3.5, 3.33, 3.25, or 3.15 wt. % HA) and 0.5 to 2.75 wt. % carbon nanotubes (e.g., at least 0.5, 0.6, 0.67, 0.75, 0.8, 0.85, 0.9, 0.95, 1, 1.05, 1.1, 1.15, 1.2, 1.25, 1.3, 1.33, 1.375, 1.4, 1.45, 1.5, 1.6, 1.67, 1.7, 1.75, 1.8, 1.85, 1.9, 1.95, or 2 wt. % CNTs and/or up to 2.75, 2.67, 2.6, 2.55, 2.5, 2.45, 2.4, 2.375, 2.33, 2.3, 2.25, 2.2, 2.15, 2.1, 2.05, 2, 1.95, 1.9, 1.85, 1.8, 1.75, 1.67, 1.6, 1.55, 1.5, 1.45, 1.4, 1.375, 1.33, 1.25 wt. % CNTs) in a polymer matrix comprising at least 75, 80, 85, 90, 91, 92, 92.5, 93, 94, 95, 96, 97, 97.5, 98, 99, 99.1, 99.5, or 99.9 wt. % ultra high molecular weight polyethylene, relative to the mass of all materials in the polymer matrix. The weight percentages of the coating compositions are given above relative to the total weight of the coating material. The coating may comprise the carbon nanotubes in a range of from 1 to 2 wt. % and/or the hydroxyapatite in a range of from 2.5 to 3.5 wt. %. Inventive coatings generally contact the underlying substrate directly, i.e., without any intervening layers other than, e.g., inevitable interfacial/surface oxide layer(s)/gradient(s). Such coatings may have a thickness of between 60 and 1000 μm. Inventive coatings may have a thickness of, e.g., at least 75, 100, 110, 125, 135, 142.5, 150, 160, 170, 175, 177.5, 180, 182.5, 185, 187.5, 190, 200, or 225 μm and/or up to 1000, 750, 500, 450, 400, 350, 325, 300, 275, 250, 225, 215, 200, 195, 190, 185, 180, or 175 μm. The coating may have a thickness of at least 100 μm. Inventive articles may consist essentially of (e.g., have at least 95, 96, 97, 97.5, 98, 98.5, 99, 99.5, or 99.9% the hardness and/or wear resistance of an article with 1.5 wt. % CNTs and 3 wt. % HA under the 12 N test described below) or consist of the substrate and coating, or may have no further layers beyond the coating on the coating side opposite the substrate and/or on the coating side facing the substrate.

The coatings may supplant portions or all of the polymer matrix with an alternate, preferably biologically compatible polymer, such as different molecular weight PE, PP, polylactide, and/or polyamide. Inventive coatings may exclude other components beyond the CNT, HA, and polymer matrix (e.g., UHMWPE), or contain no more than 5, 4, 3, 2.5, 2, 1, 0.5, 0.1, 0.01, 0.001, 0.0001, or 0.00001 wt. %, relative to total coating weight, of any substance beyond CNT, HA, and polymer matrix (e.g., UHMWPE). The articles may comprise not further layers beyond the coating and the substrate, though the coating and/or substrate may be infused and/or surface-treated with, e.g., an antibiotic and/or a chemical and/or biologic to prevent immunological rejection.

The substrate may be metallic, e.g., comprising elemental titanium, gold, cobalt, tantalum, chromium, nickel, and/or stainless steel, and/or may comprise at least 75 wt. % pure titanium or Ti6Al4V, based upon total substrate weight. The substrate may be pure titanium or Ti6Al4V. Substrates useful in combination with inventive coatings may include UWHWPE, titanium (Grade 1—ASTM F67/ISO 5832-2/3.7025/R50250, Grade 2—ASTM F67/ISO 5832-2/R50400/~3.7035/T40, . . . Grade 5), titanium alloy (e.g., TiZr1317, Ti6Al4V, Ti20Nb13Zr, Ti-8Ni-Cr, Ti6Al7Nb, Ti5Al2.5Fe, etc.), tantalum, tantalum alloy, (austenitic) stainless steel (e.g., X10CrNi18-8/~AISI 301, X5CrNiMo17-12-2/~AISI 316, X2CrNiMo17-12-2/~AISI 316L, X2CrNiMo18-14-3/~AISI 316L, X2CrNiMo18-15-3/ISO 5832-1/ASTM F139, etc.), cobalt chromium alloy (e.g., austenitic cobalt-based alloy 40% Co, 20% Cr, 16% Ni, and 7% Mo, each percentage potentially varying by 0.1, 0.25, 0.5, 0.75, 1, 1.5, or 2.5%), or the like. Relevant substrate materials are described in, e.g., *J. Powder Metall. Min.* 2013, 2, 110, *Biomater.* 2009, 30(8), 1512-1523, *Mater. Res.* B. 2016, 104B, 1282-1289, *Joint Replacement Technology* $2^{nd}$ Ed., Peter A. Revell (ed.), Woodhead: London, 2014, *Biomaterials Science* $3^{rd}$ Ed., Hallab and J. J. Jacobs (eds.), Academic Press: New York, 2013, *J. Endourol.* 1997, 11(6), 383-389, *Int. J. Prosthodont.* 1993, 6(2), 106-117, *Clin. Oral Implants Res.* 2012, 23(10), 1136-1141, *World J. Clin. Cases* 2015, 3(1), 52-57, U.S. Pat. No. 9,700,652, *Mater. Sci. Eng. A* 1996, 213(1-2), 138-147, *Nanotox.* 2017, 11(3), 327-338, *Advances in Metallic Biomaterials*. M. Niinomi, T. Narushima, and M. Nakai (eds.), vol 3, Springer: Berlin, 2015, *Arch. Metall. Mater.* 2016, 61(2), 695-700, each of which are incorporated by reference herein in its entirety.

Useful UHMWPE materials may have a Mw of, e.g., at least 500,000, 750,000, 1,000,000, 1,250,000, 1,500,000, 1,750,000, 2,000,000, 2,250,000, 2,500,000, 2,750,000, 3,000,000, 3,250,000, 3,500,000, 3,750,000, 4,000,000, 4,250,000, 4,500,000, 4,750,000, 5,000,000, 5,250,000, 5,500,000, 5,750,000, or 6,000,000 g/mol and/or up to 15,000,000, 12,500,000, 12,000,000, 11,000,000, 10,500,000, 10,000,000, 9,750,000, 9,500,000, 9,250,000, 9,000,000, 8,750,000, 8,500,000, 8,250,000, 8,000,000, 7,750,000, 7,500,000, 7,250,000, 7,000,000, 6,750,000, 6,500,000, 6,250,000, 6,000,000, 5,750,000, 5,500,000, 5,250,000, 5,000,000, 4,750,000, 4,500,000, 4,250,000, or 4,000,000 g/mol. The ultra high molecular weight polyethylene may have a Mn of at least 1,000,000 g/mol. Useful UHMWPE powders/materials may have a polydispersity index (PDI) of, e.g., at least 1.01, 1.025, 1.05, 1.1, 1.15, 1.2, 1.25, 1.33, 1.4, 1.45, 1.5, 1.6, 1.75, 1.85, 2, 2.25, 2.5, or 3 and/or up to 10, 7.5, 6.5, 5.5, 5, 4.5, 4, 3.75, 3.5, 3.25, 3, 2.75, 2.5, 2.25, 2, 1.9, 1.85, 1.8, 1.75, 1.7, 1.65, 1.6, 1.55, 1.5, 1.45, 1.4, 1.35, or 1.3. The polymer's molecular weight distribution may be monomodal, bimodal, trimodal, tetramodal, etc.

At least 50, 60, 70, 75, 80, 85, 90, 91, 92, 92.5, 93, 94, 95, 96, 97, 97.5, 98, 99, 99.1, or 99.5 wt. % of the hydroxyapatite and carbon nanotubes, relative total weights thereof in the coating, may be completely surrounded by the polymer matrix. That is, rather than being present as a separate layer or coating upon the coating, the HA and CNT are generally embedded in the polymer matrix, potentially even entirely, though generally at least to the extent that only inevitable statistical distributions of particles are exposed at the outer surface of the polymer matrix of the coating. Generally, no HA and/or CNT agglomerations are visible on the surface of the coating under SEM analysis of the coating, e.g., no more than 5, 4, 3, 2.5, 2, 1, 0.5, 0.1, 0.01, 0.001, 0.0001, 0.00001, 0.000001, or 0.0000001% of the outer (non-substrate) surface area of the coating has any such agglomerations.

The coating may be configured to directly contact animal tissue in operation. That is, the coating generally has two sides relative to the substrate, the first side contacting the substrate and the second side being exposed to the biological system for which the article is intended, e.g., mouth or bone environment. The animal may be a human, household pet (dog, cat, etc.), livestock (cow, pig, goat, etc.), zoological animal (tiger, lion, panda, bear, giraffe, gorilla, chimpazee, rhinoceros, ostrich, alligator, etc.) or the like.

The carbon nanotubes may have an outer diameter in a range of from 40 to 60 nm, a length in a range of from 1 to 2 μm, and/or a specific surface area in a range of from 60 to 70 $m^2/g$. Useful carbon nanotubes (CNTs) within the scope of the invention are not particularly limited, but may have, for example, outer diameters of at least 40, 41, 42, 43, 44, 45, 46, 47, 48, 49, or 50 nm and/or up to 60, 59, 58, 57, 56, 55, 54, 53, 52, 51, or 50 nm. Useful CNTs may have a length of, e.g., at least 1, 1.05, 1.1, 1.15, 1.2, 1.25, 1.3, 1.35, 1.4, 1.45, or 1.5 μm and/or up to 2, 1.95, 1.9, 1.85, 1.8, 1.75, 1.7, 1.65, 1.6, 1.55, or 1.5 μm. Useful CNTs may have a specific surface area of, e.g., at least 60, 60.5, 61, 61.5, 62, 62.5, 63, 63.5, 64, 64.5, 65 $m^2/g$ and/or up to 70, 69.5, 69, 68.5, 68, 67.5, 67, 66.5, 66, 65.5, or 65 $m^2/g$). The carbon nanotubes may include single and/or multi-walled CNTs.

Inventive articles may have a Vickers hardness on a surface of the coating opposite the substrate of at least 8, 8.25, 8.5, 8.75, 9, 9.25, 9.5, 9.75, 10, 10.25, 10.5, 10.75, 11, 11.25, 11.5, 11.75, or 12, and/or up to 20, 19, 18, 17, 16, 15, 14.5, 14, 13.5, 13, 12.5, 12, 11.5, 11, 10.5, or 10.

Aspects of the invention include methods of preparing coated substrates in any permutation described herein. Such methods may comprise: pretreating the substrate including contacting the substrate with plasma, e.g., some kind of plasma such as air-plasma, $N_2$-plasma, He-plasma, Xe-plasma, Ar-plasma, $O_2$-plasma, or the like, to obtain a pretreated substrate. The contacting may generally involve flowing a plasma onto the substrate. The methods generally further involve electrospraying, i.e., electrostatic powder spray coating, onto the pretreated substrate a solid comprising at least 75 wt. % (or any amount discussed above) of ultra high molecular weight polyethylene, 0.5 to 4.75 wt. % (or any amount discussed above) of hydroxyapatite, and 0.5 to 2.75 wt. % (or any amount discussed above) of carbon nanotubes, to obtain a coated substrate. The solid electrosprayed onto the substrate is generally a mixed, sonicated, substance, which may have been prepared by mechanical mixing, optionally in solution or suspension in a solvent (or liquid), such as pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pet ether, pentane, hexane(s), cyclohexane, decane(s), decalin, THF, dioxane, benzene, toluene, xylene(s), o-dichlorobenzene, diethyl ether, methyl t-butyl ether, diisopropyl ether, ethylene glycol, methanol, ethanol, isopropanol, propanol, n-butanol, and/or water.

The pretreating may further comprise, after the contacting, heating the substrate to at least the melting point of the polymer matrix, such as at least 140, 145, 150, 155, 160, 165, 170, 175, 180, 185, 190, 195, or 200° C. (and/or up to 300, 290, 280, 270, 260, 250, 240, 230, 220, 210, 200, 190, or 180° C.), to obtain the pretreated substrate. Such methods may further comprise, after the electrospraying: heating the coated substrate to at least the melting point of the polymer matrix, such as at least 140, 145, 150, 155, 160, 165, 170, 175, 180, 185, 190, 195, or 200° C. and/or up to 280, 270, 260, 250, 240, 230, 220, 210, 200, 190, or 180° C.

Aspects of the invention comprise methods for improving the wear resistance of a coated substrate in any inventive permutation described herein, the method comprising coating a substrate with a mixture comprising at least 50, 60, 70, 75, 80, 85, 90, or 95 wt. % UHMWPE (or any amount described above) and between 0.25 and 2.75 wt. % (or any amount described above) carbon nanotubes and 0.25 to 4.75 wt. % (or any amount described above) hydroxyapatite, a remainder comprising polymer material.

Aspects of the invention provide methods of improving the uniformity of the distribution of hydroxyapatite and carbon nanotube additives in a coating, the method comprising: combining 0.5 to 4.75 wt. % (or any amount described above) hydroxyapatite, 0.5 to 2.75 wt. % (or any amount described above) carbon nanotubes, and at least 75 wt. % (or any amount described above) ultra high molecular weight polyethylene to obtain a coating precursor mixture; mechanically agitating, e.g., with a stirrer, sonicator, and/or shaker, generally less destructive than, e.g., ball milling, the coating precursor mixture, to obtain an agitated mixture; and applying the agitated mixture to a preheated substrate by electrostatic spray coating a powder, wherein the preheated substrate is preheated to a temperature of at least the melting point of the ultra high molecular weight polyethylene (or any temperature described above).

Inventive materials and/or polymer matrices need not comprise any $TiO_2$ nanostructures, e.g., nanotubes, nanospheres, nanowires, or the like, or amorphic powder, and/or may contain no more than 5, 4, 3, 2.5, 2, 1, 0.5, 0.1, 0.01, 0.001, 0.0001, or 0.00001 wt. %, relative to total material and/or matrix weight, of such $TiO_2$ nanostructures and/or $TiO_2$, and/or those of $SiO_2$, $ZrO_2$, $Al_2O_3$, $Fe_2O_3$, $Fe_3O_4$, and/or $CaCO_3$ Inventive materials and/or polymer matrices need not comprise any $TiO_2$, $SiO_2$, $ZrO_2$, $Al_2O_3$, $Fe_2O_3$, $Fe_3O_4$, and/or $CaCO_3$, and/or may contain no more than 5, 4, 3, 2.5, 2, 1, 0.5, 0.1, 0.01, 0.001, 0.0001, or 0.00001 wt. %, relative to total material and/or matrix weight, of $TiO_2$, $SiO_2$, $ZrO_2$, $Al_2O_3$, $Fe_2O_3$, $Fe_3O_4$, and/or $CaCO_3$.

Inventive materials may include hydroxyapatite (HA) and carbon nanotube (CNT) in a HA-to-CNT weight ratio of, e.g., at least 9:1, 8:1, 7:1, 6:1, 5:1, 4:1, 3:1, 2.5:1, 2:1, 1.75:1, 1.5:1, 1.25:1, or 1:1 and/or up to 1:6, 1:5, 1:4, 1:3.5, 1:3, 1:2.5, 1:2, 1:1.75, 1:1.5, 1:1.25, 1:1, especially centered around 2±0.05, 0.1, 0.15, 0.2, 0.25, 0.3, 0.33, 0.35, 0.4, 0.45, or 0.5:1.

Inventive coatings do not require a ligand-structural entity complex, nor any ligands, but instead may rely entanglements, rather than, for example covalent, ionic, π-stacking, T-stacking, and/or cation/aromatic interactions, etc., using instead entanglements in the polymer matrix to bind the coating and/or its components together, locking their dispersion locations with respect to each other, and/or to the surface of the substrate. Inventive coatings generally need not provide any interaction that stabilizes the $sp^2$-hybridization of the carbon nanotubes.

Useful polymers for inventive coatings are generally (co, ter)polymers of monoolefins and/or diolefins, for example, ethylene, propylene, isobutylene, but-1-ene, 4-methylpent-1-ene, vinylcyclohexane, isoprene, butadiene, cyclopentene, and/or norbornene, which may be crosslinked and/or branched. Examples of polyethylenes which may be useful in inventive coatings may be, e.g., high density polyethylene (HDPE), (high density and) high molecular weight polyethylene (HMWPE), (high density and) ultrahigh molecular weight polyethylene (UHMWPE), medium density polyethylene (MDPE), low density polyethylene (LDPE), linear low density polyethylene (LLDPE), (VLDPE), and/or (ULDPE), though high molecular weights, e.g., above 500,000 may be preferred in biological applications. Such polymers may supplement or replace UHMWPE in the coating.

Inventive materials, beyond CNT and/or HA, may exclude or have no more than (UV spectroscopically detectable amounts of one more additives including (poly and/or oligo)peptide, amino acids, nucleotides, nucleosides, RNA, DNA, amelogenin, carbon fiber/thread, ceramic, fullerene including (buckyball, buckytube, etc.), graphane, prismane, graphene oxide, MWCNT, SWCNT, graphite, graphyne, (metal-, HOOC—, HO—, $H_2N$—, HS—, etc.) functionalized CNT, (metal-, HOOC—, HO—, $H_2N$—, HS— etc.) functionalized graphene, multi-layer graphene, reduced graphene oxide, dodecahedrane, diamond, diamond-like carbon, synthetic diamond, carbon black, carbon nanofoam, fluorinated graphene, exfoliated graphite, exfoliated silicate, glass fiber, E-glass, S-glass, doped glass, silica, fused silica, wood, battery, capacitor, dielectric/insulator, ionic crystal, electrode (anode and/or cathode), diode, mineral, piezoelectric, sapphire, semiconductor, sensor, calcium metasilicate, hydrous magnesium silicate, borosilicate, metal oxide, silicon nitride, sol-gel, tungsten carbide, gallium arsenide, gallium nitride, alumina trihydrate, aluminum boride, iron oxides, lead zirconium titanate, lithium niobate, silicon carbide, silicon nitride, zirconia, $TiO_2$, tooth (cementum, dentine, and/or enamel), lonsdaleite, $Mg(OH)_2$, MgO, $Al_2O_3$, $Al(OH)_3$, ZnO, $CaSO_4$, amalgam, elastomer, anthracite, asbestos, clay, mica, bone, metalloid, catalyst, metal alloy, transition metal, actinide, lanthanide, platinum group metal, post-transition metal, rare earth element, Si, Ba, Al, Cr, Cu, Ge, Au, Mn, Mo, Ni, B, Pd, Pt, W, Ag, Ta, Ti, Fe, steel, intermetallic, brass, polyester, polyether, polyamide, aramid, polycarbonate, PEEK, PES, nylon, and/or combinations of two or more of any of these. Inventive materials may contain no more than 5, 4, 3, 2.5, 2, 1, 0.5, 0.1, 0.01, 0.001, 0.0001, or 0.00001 wt. %, relative to total material and/or matrix weight, of such additives, alone or in combination.

Aspects of the invention provide a polymer-based hybrid nanocomposite coating comprising UHMWPE, 0.25 to 3 wt. % carbon nanotubes (CNT), e.g., 0.5, 1.5, and 3 wt. %, and 0.25 to 5 wt. % hydroxyapatite (HA), e.g., 0.5, 1.5, 3, and 5 wt. %, preferably on a substrate, which may be a polymer itself, e.g., UHMWPE, or may include pure titanium (Grade 1, 2, . . . ), titanium alloy, such as Ti6Al4V, or the like. The substrate may include at least 75, 80, 85, 90, 91, 92, 92.5, 93, 94, 95, 96, 97, 97.5, 98, 99, 99.1, 99.5, or 99.9 wt. % of UHMWPE, pure titanium (Grade 1 or 2), or titanium alloy, relative to total substrate weight.

While pure UHMWPE coatings may fail at a normal load of 12N and a sliding velocity of 0.1 m/s showing a wear life of ~3600 cycles, 0.5 wt. % CNT-filled coatings can survive 28,000 cycles, 1.5 wt. % CNT-filled coatings can survive 50,000 cycles, and 3 wt. % CNT-filled coatings can survive 7000 cycles. Adding 3 wt. % HA to the 0.5 wt. % CNT-filled coatings can provide an endurance of 250,000 cycles.

Aspects of the invention provide hybrid nanocomposite coatings on (pure) titanium and Ti6Al4V to enhance their tribological properties, generally including UHMWPE as a parent polymer matrix, e.g., for biocompatibility and good tribological properties, and preferably also CNTs, e.g., 0.5, 1.5, and 3 wt. %, introduced into the UHMWPE matrix to enhance the load bearing capacity of UHMWPE. Different amounts, e.g., 0.5, 1.5, 3, and 5 wt. %, of HA may be (further) added, e.g., to improve the biocompatibility of the hybrid nanocomposite coating.

While the following properties of relevant UHMWPE materials are not required to practice the invention, they may be useful in certain applications. Useful UHMWPE powders/materials may have a coefficient of friction of, e.g., at least 0.07, 0.08, 0.085, 0.09, 0.095, 0.0975, 0.098, 0.099, 0.1, 0.1025, 0.105, 0.1075, 0.11, 0.1125, 0.115, 0.1175, 0.12, 0.1225, 0.125, 0.1275, 0.13, 0.1325, 0.135, 0.1375, 0.14, 0.1425, 0.145, 0.1475, 0.15 and/or up to 0.4, 0.35, 0.325, 0.3, 0.295, 0.29, 0.285, 0.28, 0.275, 0.27, 0.265, 0.26, 0.255, 0.25, 0.245, 0.24, 0.235, 0.23, 0.2275, 0.225, 0.2225, 0.22, 0.2175, 0.215, 0.2125, 0.21, 0.2075, 0.205, 0.2025, 0.2, 0.1975, 0.195, 0.1925, 0.19, 0.1875, 0.185, 0.1825, or 0.18. Relevant UHMWPE powders/materials may have an elongation at break, e.g., up to 1000, 900, 800, 750, 700, 650, 600, 575, 550, 525, 500, 475, 450, 425, or 425% and/or at least 250, 300, 350, 400, 425, 450, 475, 500, 525, 550, 575, or 600%. Useful UHMWPE powders/materials may have a Rockwell hardness of, e.g., at least R40, 42.5, 45, 47.5, 50, 52.5, 55, 57.5, or 60 and/or up to R90, 87.5, 85, 82.5, 80, 77.5, 75, 72.5, 70, 67.5, 65, 62.5, 60, 57.5, 55, 52.5, or 50. Useful UHMWPE powders/materials may have an Izod impact strength of, e.g., at least 900, 950, 975, 1000, 1025, 1050, 1075, 1100, 1125, 1150, 1175, 1200, or 1250 J/m and/or up to 1500, 1450, 1400, 1375, 1350, 1325, 1300, 1275, or 1250 J/m. Useful UHMWPE powders/materials may have a Poisson's ratio of, e.g., at least 0.4, 0.41, 0.415, 0.42, 0.425, 0.43, 0.435, 0.44, 0.445, 0.45, 0.455, 0.46, 0.465, 0.47, 0.475, 0.48, 0.485, 0.49, 0.495, or 0.5 and/or up to 0.6, 0.59, 0.58, 0.57, 0.56, 0.55, 0.54, 0.53, 0.52, 0.51, 0.5, 0.49, 0.485, 0.48, 0.475, 0.47, 0.465, 0.46, 0.455, 0.45, 0.445, or 0.44. Useful UHMWPE powders/materials may have a tensile modulus of, e.g., at least 0.1, 0.125, 0.15, 0.175, 0.2, 0.225, 0.25, 0.275, 0.3, 0.325, 0.35, 0.4, 0.45, 0.5, 0.55, 0.6, 0.65, 0.7, or 0.75 GPa and/or up to 1.5, 1.45, 1.4, 1.35, 1.3, 1.25, 1.2, 1.15, 1.1, 1.05, 1, 0.95, 0.9, 0.85, 0.8, or 0.75 GPa.

Useful UHMWPE powders/materials may have a tensile strength of, e.g., at least 15, 16, 17, 17.5, 18, 19, 20, 21, 22, 22.5, 25, or 27.5 MPa and/or up to 50, 47.5, 45, 44, 43, 42.5, 42, 41, 40, 39, 38, 37.5, 37, 36, or 35 MPa. Useful UHMWPE powders/materials may have a density of, e.g., at least 0.935, 0.9375, 0.938, 0.938, 0.94, 0.941, 0.942, 0.9425, 0.945, 0.9475, 0.95, 0.9525, 0.955, 0.9575, 0.96, 0.9625, 0.965, 0.9675, 0.97, 0.9725, 0.975, 0.9775, or 0.98 and/or up to 0.98, 0.975, 0.97, 0.9675, 0.965, 0.9625, 0.96, 0.9575, 0.955, 0.9525, 0.95, 0.9475, 0.945, 0.9425, 0.942, 0.941, 0.94, 0.939, 0.938, 0.9375, or 0.935 g/cm$^3$. Useful UHMWPE powders/materials may have a coefficient of thermal expansion of, e.g., 120, 125, 130, 135, 140, 145, or $150 \cdot 10^{-6}$/K and/or up to 220, 215, 210, 205, 200, 195, 190, 185, 180, or $175 \cdot 10^{-6}$/K. Useful UHMWPE powders/materials may have a specific heat of, e.g., at least 1850, 1860, 1870, 1875, 1880, 1885, 1890, 1895, 1900 J/K-kg and/or up to 1950, 1940, 1930, 1925, 1920, 1915, 1910, 1905, or 1900 J/K-kg. Useful UHMWPE powders/materials may have thermal conductivity at 23° C. of, e.g., at least 0.375, 0.38, 0.385, 0.39, 0.395, 0.4, 0.405, 0.41, 0.415, 0.42, 0.425, 0.43, 0.435, 0.44, 0.445, or 0.45 W/m-K and/or 0.51, 0.505, 0.5, 0.495, 0.49, 0.485, 0.48, 0.475, 0.47, 0.465, or 0.46 W/m-K.

EXAMPLES

Materials: Commercially available titanium sheets of Ti Grade 2—ASTM F67 (pure titanium), and Titanium Grade 5—ASTM F136 (Ti6Al4V) with the dimensions of 1 m×0.5 m×0.003 m were purchased from Xi'an Saite Metal Materials Development Co. Ltd. A gelatin machine was used to cut the samples into 25 mm×25 mm square samples. All the substrates were grinded to an average surface roughness of (Ra)=0.51±0.04 µm.

UHMWPE powder was purchased from the Goodfellow Corp., UK, having an average particle size ranged between 80 to 90 µm and a density of 0.94 g/cm$^3$. Carbon nanotubes (CNTs) were purchased from Nanostructured & Amorphous Materials Inc., Houston, Tex., USA. The outer diameter of the CNTs ranged from 40 to 60 nm with a length of from 1 to 2 µm and a specific surface area of from 60 to 70 m$^2$/g.

Hydroxyapatite (HA), $Ca_5(PO_4)_3(OH)$ or $Ca_{10}(PO_4)_6(OH)_2$, was used as a second filler along with the CNTs, in an effort to improve biocompatibility and enhance mechanical properties of the hybrid coating. HA was prepared according to the method described in *Quim. Nova* 2012, 35(9), 1724-1727, which is incorporated by reference herein in its entirety. Calcium chloride, i.e., $CaCl_2$, (0.555 g, 5.00 mmol), 0.150 g (1.25 mmol) of sodium dihydrogen phosphate, i.e., $NaH_2PO_4$, and 0.073 g (0.869 mmol) of sodium bicarbonate, i.e., $NaHCO_3$, were dissolved in 500 mL of distilled water. The solution was stirred for 24 hours at 37° C. and 80 rpm. At the end of the procedure, the precipitate was washed with deionized water and dried at 110° C. for 2 hours in an oven. This procedure was successfully scaled 50-fold to obtain HA for experiments herein. The HA powder was white in color and had a plate-like structure with a thickness ranging from 0.3 to 0.5 µm.

Hybrid Nanocomposite Powder Preparation

To prepare exemplary nanocomposite powders, 10 g of UHMWPE reinforced with X wt. % of carbon nanotubes (CNTs), with X indicating grams of CNT weighed and emptied into a beaker containing 50 mL of ethanol and sonicated for 10 minutes using a probe sonicator. After sonication, the solution was magnetically stirred at 1000 RPM and the particular quantity of UHMWPE powder was added gradually. The magnetic stirring was continued for 60 minutes, followed by a heat treatment to completely evaporate the ethanol and yield a nanocomposite powder of UHMWPE reinforced with CNTs, which was collected and stored for subsequent characterization and tests.

Exemplary hybrid nanocomposite powders of 10 g of UHMWPE reinforced with X wt. % CNT and Y wt. % hydroxyapatite (HA) were prepared by the method in *Appl. Surf. Sci.* 2009, 255, 6736-6744, which is incorporated by reference herein in its entirety. Masses of Y grams of HA were added to 50 mL of ethanol and stirred using a magnetic stirrer for 10 minutes. After the stirring, the solution of ethanol and HA was sonicated for 30 minutes. Masses of X grams of CNT were then added to the sonicated solution containing ethanol and HA, sonicating for another 30 minutes. After the sonication, the solution was magnetically stirred followed by a heat treatment to evaporate ethanol and obtain the hybrid nanocomposite powders.

Coating Procedure

A Craftsman Model No. 17288 electrostatic powder spray coating gun was used to coat the samples. Prior to coating, all samples were ultrasonically cleaned, dried, then treated with air-plasma, and pre-heated for 5 minutes at 180° C. for better adhesion of the coating. The plasma treatment involved directing a Harrick Plasma device at the substrate for 10 minutes at a radio-frequency power of 30 W. Plasma treatments may be as described in *Med. Device Technol.* 1999, 10, 24-30, which is incorporated by reference herein in its entirety. After the plasma treatment, the substrates were further pre-heated for 15 minutes on a hot plate to a temperature of 180° C. After the spraying of powder of the specified compositions, the samples were cured at 180° C. for 30 to 35 minutes, followed by air cooling, to attain the final specimens for further characterization, as described in *Prog. Org. Coatings* 2018, 118, 97-107, which is incorporated by reference herein in its entirety.

Thickness Measurements

The thickness of the coatings was evaluated using the eield emission scanning electron microscope (FE-SEM) and confirmed by an Elcometer 456 dry film thickness gauge. Two samples of each composition were used, and three recordings were made, with the average value of the thickness being reported. Pure (unfilled) UHMWPE had an average coating thickness of 142±4 µm. The nanocomposite (carbon nanotube, CNT-filled) coating had an average coating thickness of 181±4 µm. The hybrid (CNT and hydroxyapatite, HA-filled) nanocomposite coating had an average coating thickness of 185±4 µm.

Tribological Characterization

A Bruker UMT-3 Tribometer, with a ball on disk configuration, was used for the tribological tests. A 440C stainless steel ball with a diameter of 6.3 mm and a Rockwell C hardness of RC 62 was used as a counterface. The coatings were tested under loads of 7, 9, 12, and 15 N to optimize the loadings of the reinforcements.

To evaluate coating failure a sudden spike in the friction coefficient was taken to suggest a metal to metal contact or too many fluctuations in the coefficient of friction (COF) graph. Wear track analysis coupled with EDX analysis was used to ascertain the coating failure optical microscopic assessment for wear and tear on the counterface ball. Wear tests were conducted on three samples of each composition and the average value of coefficient of friction and specific wear rate are reported.

Wear depth, wear volume, and specific wear rates were calculated using a Bruker 3D GTK-A optical profilometer. Specific wear rates can be calculated by initially finding the area under the curve of a 2-D profilometer plot provided by the computer and multiplying it with the track circumference, i.e., $2\pi r$, where r stands for the track radius, to calculate the wear volume. The wear volume is then divided by the applied normal load and distance traveled by the ball as shown in Equation 1, below:

$$\text{Specific Wear rate} = \frac{\text{Wear volume}}{\text{Applied Normal load} \times \text{Distance}} = \frac{mm^3}{Nm}. \quad \text{Eq. 1}$$

A Thermo Scientific DXR Raman spectroscopy instrument (455 nm) was used for the analysis of coatings of UHMWPE reinforced with CNT to study the interaction of CNTs with the UHMWPE matrix. A Tescan VEGA3 scanning electron microscope was used to analyze the dispersion of CNTs and HA in the UHMWPE matrix. Prior to SEM imaging, the samples were sputter-coated with gold using a JFC-1100 fine coat ion sputterer.

Hardness Measurement

Vickers Hardness tests were conducted on coated samples using a Micro-Combi tester with a contact force of 0.01 N and an approach speed of 16.6 µm/min. The maximum applied load was 0.1 N with a loading and unloading rate of 0.20 N/min. The measurement was carried out on 3 samples of each type, taking the average value of 20 readings at different locations.

Scratch Test

A linear, progressive scratch test was performed for the optimized coatings using a Micro-Combi tester to ascertain the adhesion of the coatings. A rigidly mounted diamond having a Rockwell C geometry with a radius of 100 µm was used as the indenter to perform these tests. An initial load of 0.03 N, an end load of 30 N, and a loading rate of 15 N/m and a scratch length of 10 mm were defined as test parameters.

Electrochemical Corrosion Analyses

Electrochemical corrosion analyses were carried out using a typical three-electrode cell with the Gamry Instruments Reference 3000 potentiostat/galvanostat/zero resistance ammeter (ZRA). A saturated calomel electrode (SCE) was used as a reference electrode and a graphite rod as a counter electrode. A simulated human body fluid (SBF) solution was used as an electrolyte for electrochemical characterization. The preparation of SBF and the procedure for conducting the experiments is described in *J. Mater. Eng. Perform.* 2017, 26, 5553-5562 and *Materials* (Basel) 2017, 11, 26, each of which is incorporated by reference herein in its entirety. The exposed area of each sample was 1.76 cm². Open circuit potential (OCP) monitoring was conducted for about 30 minutes. Electrochemical impedance spectroscopy (EIS) measurements were taken in a frequency range from 100 kHz to 10 mHz with a sinusoidal AC voltage of 10 mV amplitude. The electrochemical corrosion experiments were repeated at least three times to confirm reproducibility.

Referring now to the drawings, wherein like reference numerals designate identical or corresponding parts throughout the several views.

Raman Evaluation of UHMWPE-CNT Interaction

Raman spectroscopy was used to study the interfacial interaction between the UHMWPE matrix and CNTs. The characteristic Raman spectrum for the pure UHMWPE and UHMWPE with the different loadings (0.5, 1.5, and 3 wt. %) of CNTs are shown in FIG. 1. As observed from the spectrum of pure UHMWPE, peaks 1 and 2 are associated with the asymmetric and symmetric stretching modes of the C—C bond whereas peaks 3 to 8 are subsequent to the twisting and bending modes of $CH_2$.

The Raman spectrum of CNTs alone (without polymer) exhibited two characteristic peaks. The first CNT-Raman peak at 1357 $cm^{-1}$ can be assigned to the D band indicating disordered graphite structures. The second CNT-Raman peak, centered at 1574 $cm^{-1}$, can be assigned to the G-band and correlates with the tangential C—C bond stretching motions.

Upon addition of 1.5 wt. % CNT, a maximum shift of 27 $cm^{-1}$ in the position of the G-band peak is observed. The shifting of the G-Band peak to a higher frequency may be attributed to the disentanglement and extrication of CNTs as a result of successive dispersion in the UHMWPE matrix. The up-shift of the G-band may also represent stronger compressive forces associated with the UHMWPE chains on CNTs, indicating intercalation of the polymer into nanotube bundles. In the case of 3 wt. % CNT and 0.5 wt. % CNT in UHMWPE, the upshift in the G-band was respectively only 19 and 14 $cm^{-1}$, i.e., less shifted than for 1.5 wt. % CNT, suggesting less interaction of the CNTs with the UHMWPE matrix in the case of 3 and 0.5 wt. % CNT loading.

SEM Dispersion Analysis of CNT-UHMWPE

Figure 2A:
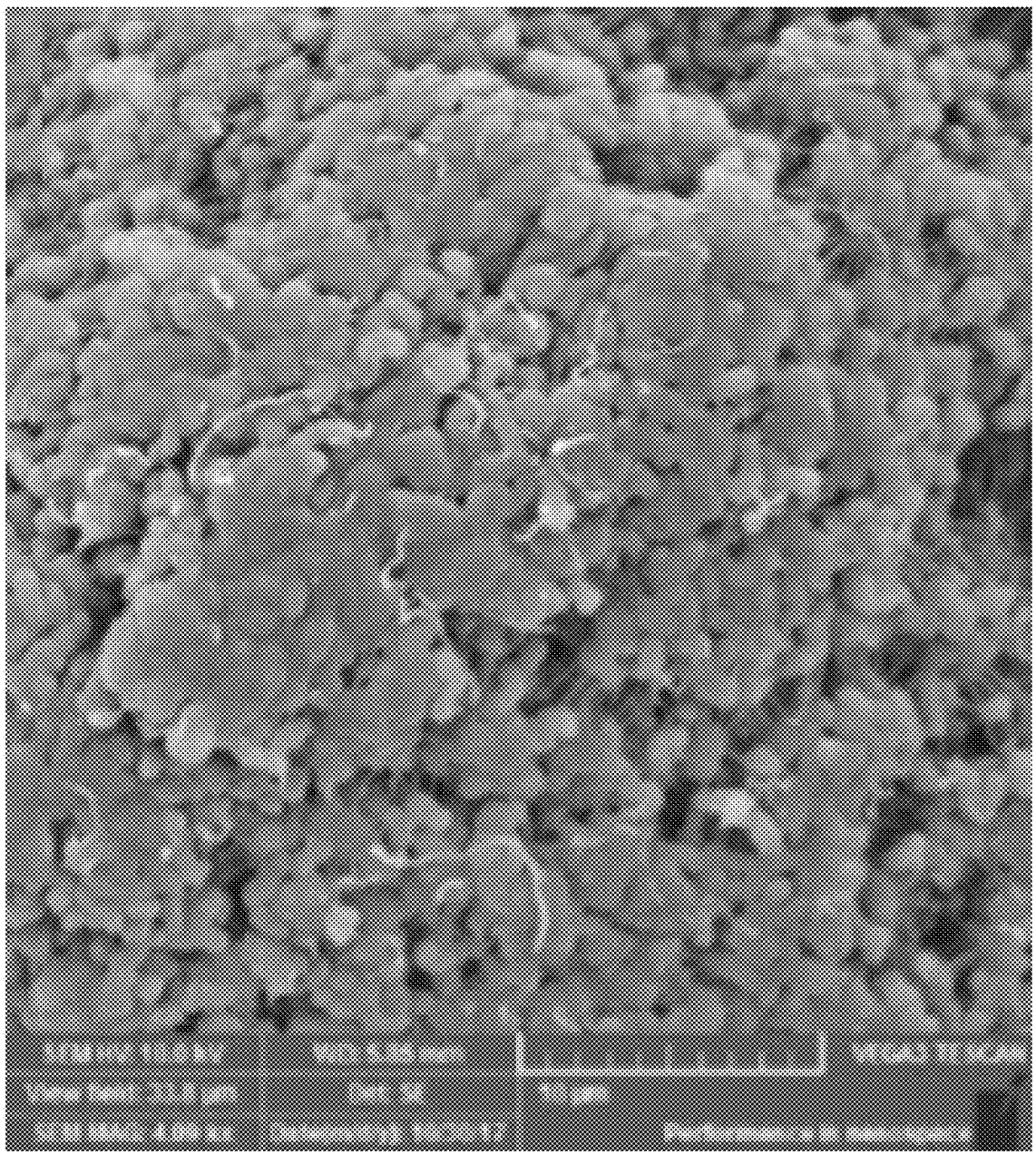
FIG. 2A shows a scanning electron microscope (SEM) image of UHMWPE including 0.5 wt. % CNTs.
Figure 2B:
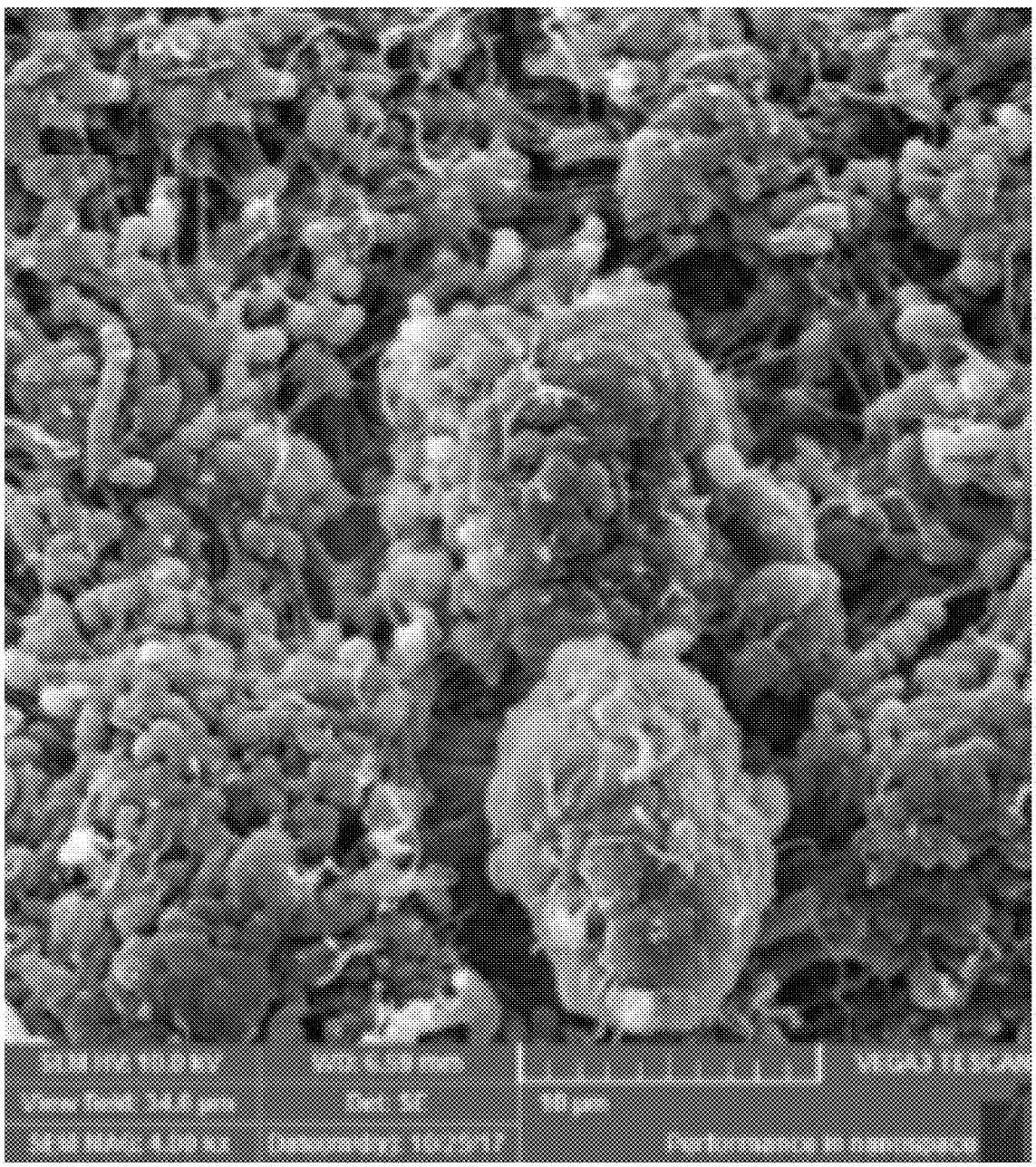
FIG. 2B shows an SEM image of UHMWPE including 1.5 wt. % CNTs.
Figure 2C:
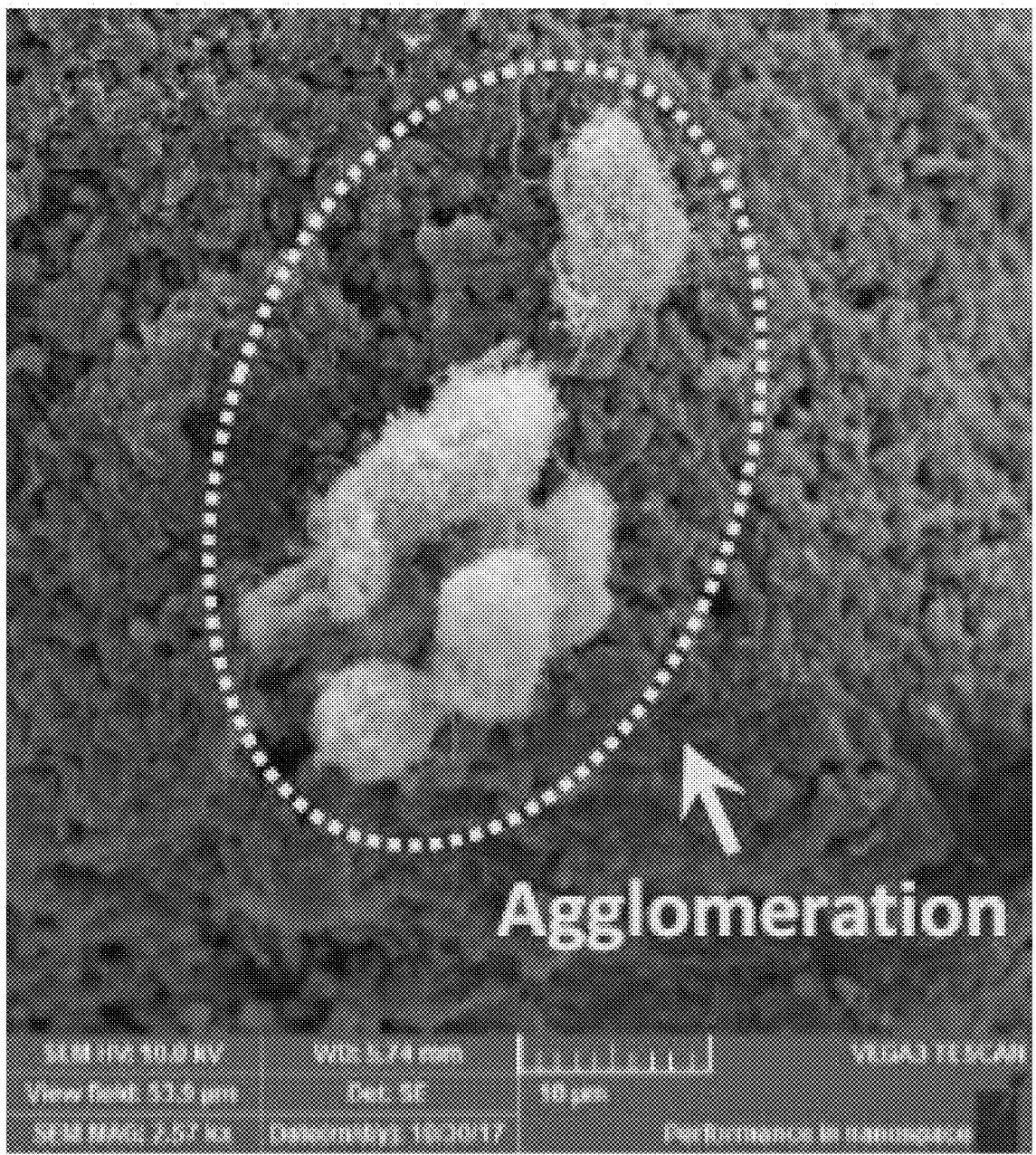
FIG. 2C shows an SEM image of UHMWPE including 3 wt. % CNTs.

Scanning electron microscope (SEM) analysis of the nanocomposite powders of UHMWPE reinforced with 0.5, 1.5, and 3 wt. % loadings of CNTs was conducted to ascertain the dispersion of CNTs in the UHMWPE polymer matrix, as shown in FIG. 2A to 2C. As seen in FIG. 2A, for nanocomposite powders of UHMWPE with 0.5 wt. % CNT loading (UHMWPE/0.5 wt % CNTs), the CNTs seem to be evenly distributed without any apparent agglomerations. A lack of agglomerations is also observed for the UHMWPE/1.5 wt % CNTs nanocomposite powders as seen in FIG. 2B. The presence of individual CNTs in different locations indicates good dispersion and almost negligible agglomeration, suggesting that the sonication process employed is effective to disperse the 0.5 and 1.5 wt. % CNTs in the UHMWPE polymer matrix. However, when the loading of CNT was increased to 3 wt. % traces of agglomeration were observed as shown in FIG. 2C.

Tribological Characterization of Pure UHMWPE Coating

Figure 3A:
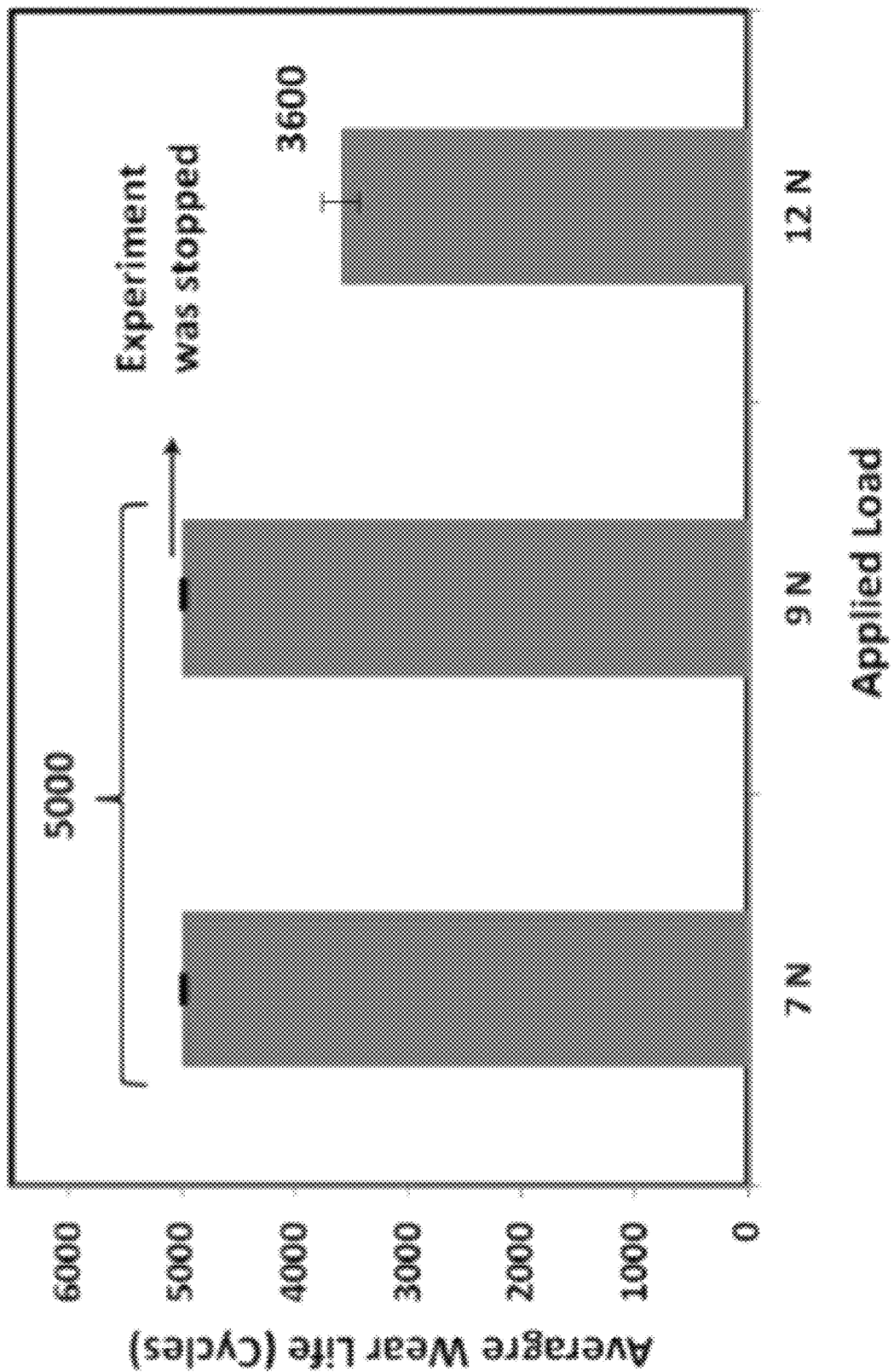
FIG. 3A shows a chart presenting the average wear life as a function of normal load of a pure UHMWPE-coated substrate.
Figure 3B:
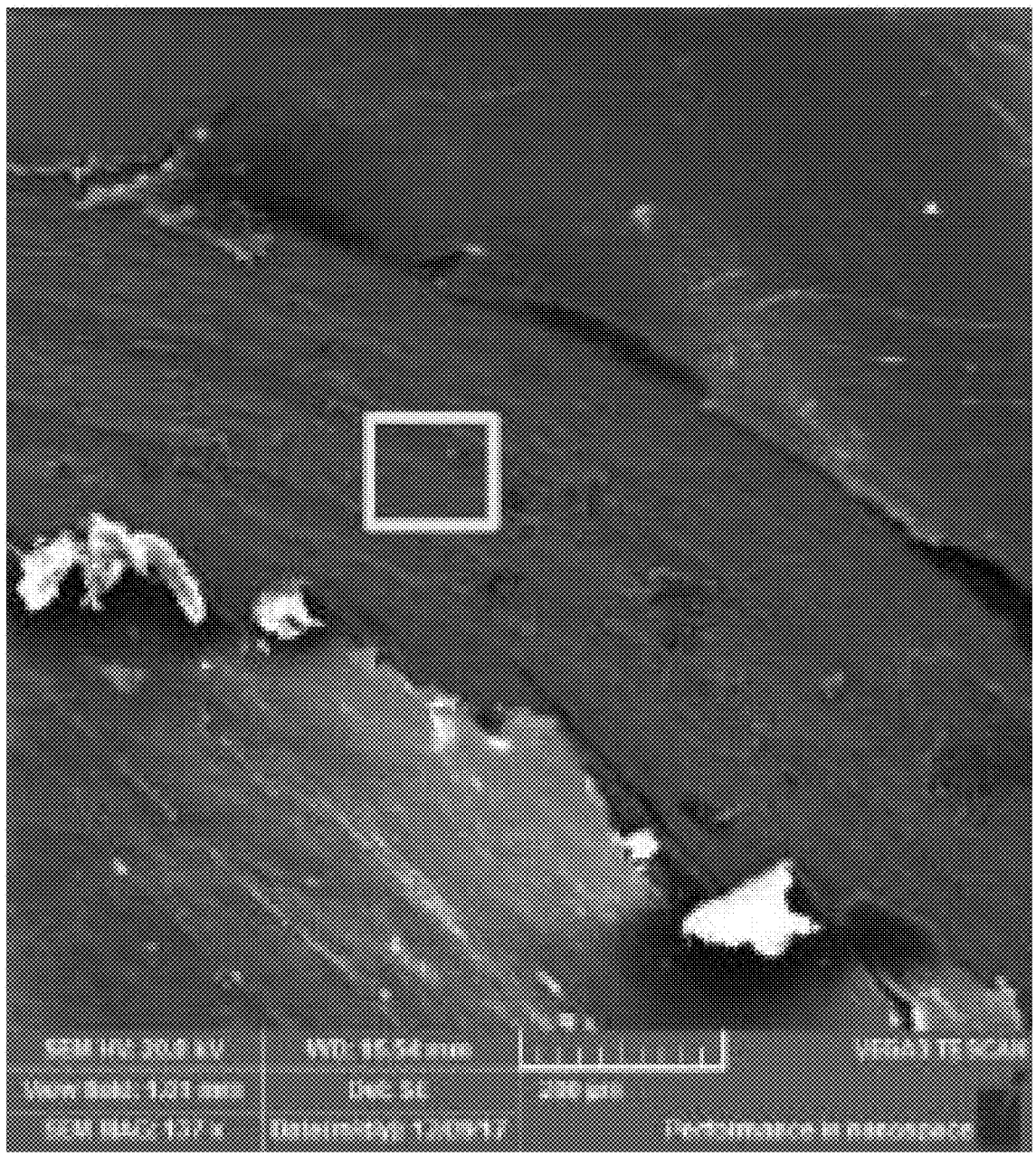
FIG. 3B shows an SEM image of the wear track of a pure UHMWPE coating after a wear test at a normal load of 12N and a sliding velocity of 0.1 m/s.
Figure 3C:
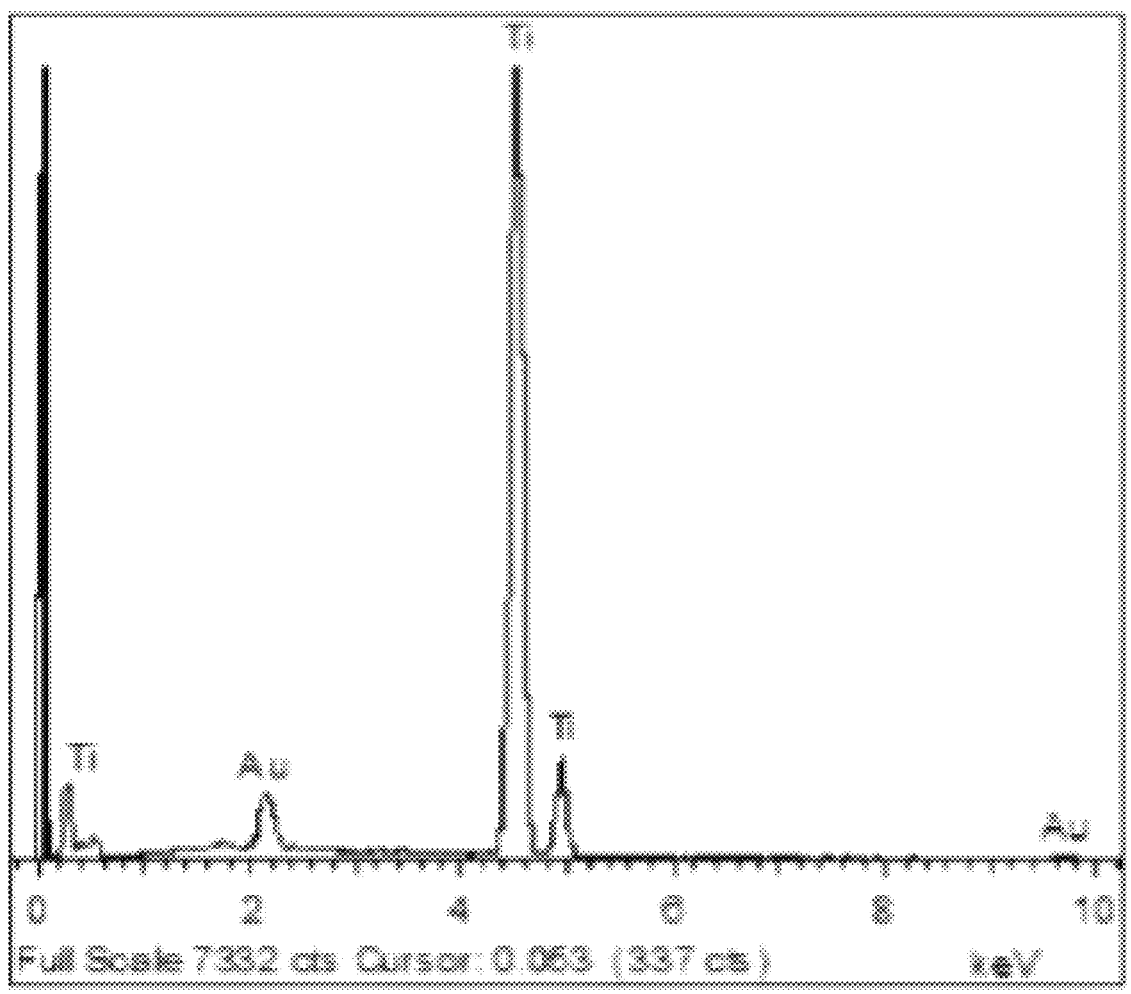
FIG. 3C shows an energy-dispersive x-ray spectroscopy (EDX) spectrum of a pure UHMWPE coating after a wear test at a normal load of 12N and a sliding velocity of 0.1 m/s.

To determine the load bearing capacity of the pure UHMWPE coating, wear tests were carried out at normal loads of 7, 9, and 12 N. Three samples were tested for each loading conditions. Tests were carried out at a constant sliding velocity of 0.1 m/s for 5000 cycles. FIG. 3A shows average wear life as a function of applied load for pure UHMWPE. The pure UHMWPE coating did not fail for 5000 cycles at a load of 7 and 9N. The test was stopped after 5000 cycles for 7 N and 9 N loads in view of the nano-failure of the coating. At a normal load of 12N, the pure UHMWPE coating failed after ~3600 cycles, as confirmed by the EDX analysis of the wear track. FIG. 3B shows a clear peak of titanium, the substrate material, indicating the failure of the coating attributable to a combination of adhesive and abrasive wear resulting in the peeling off and plowing of the coating.

Tribological Characterization of UHMWPE-CNT Coating

Figure 4A:
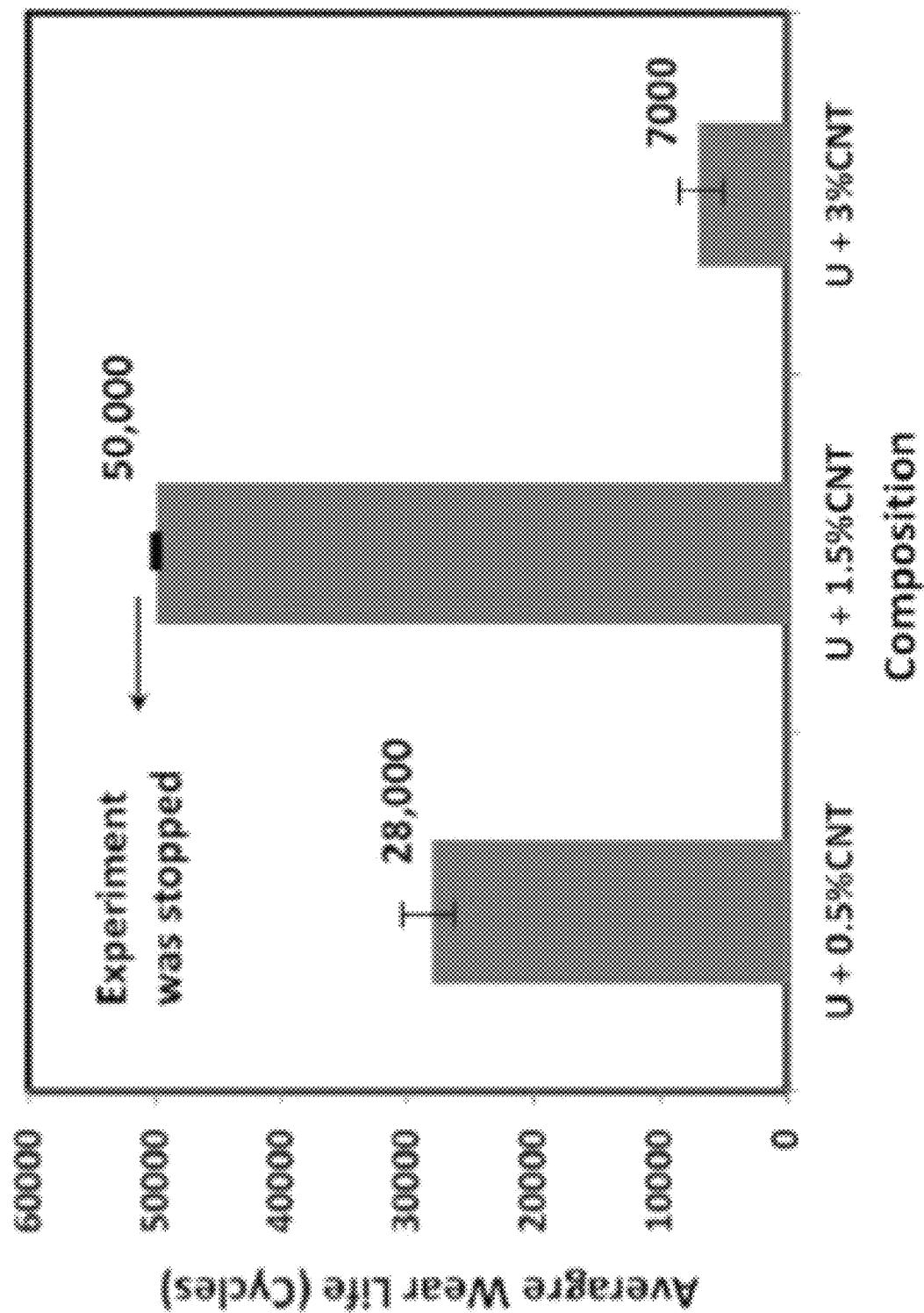
FIG. 4A shows a chart presenting the average wear life as a function of normal load of a substrate coated with UHMWPE comprising different amounts of CNTs.

FIG. 4A shows the results of loadings of 0.5, 1.5, and 3 wt. % CNTs introduced into the UHMWPE matrix, whereby three samples of each composition were tested at a load of 12 N initially with a sliding velocity of 0.1 m/s for 50,000 cycles (6276 seconds).

The addition of 0.5 wt. % CNTs into the UHMWPE polymer matrix was observed to improve the wear life of the coatings compared to pure UHMWPE coatings. The coating of UHMWPE loaded with 0.5 wt. % CNTs failed at ~28,000 cycles. A combination of adhesive and abrasive mode of failure of the coating can be observed in the SEM image as shown in FIG. 4B, and the EDX analysis confirms the exposure of the substrate.

Optical profilometry was also conducted on the wear tracks after the wear tests, and the 3D and 2D wear profiles for the different nanocomposite coatings are shown in FIG. 6A through 6L. The failure of the UHMWPE/0.5 wt % CNTs nanocomposite coating is also confirmed by the 2-D profile which shows a profile depth of ~182 µm in FIG. 6A. 182 µm is approximately the coating thickness. The optical images of the counterface ball sliding against the coating recorded before and after the test, before cleaning and after cleaning, for typical runs are shown in FIGS. 6B to 6D, 6F to 6H, and 6J to 6L. A good amount of material pullout is clearly visible on the counterface ball in FIGS. 6C, 6G, and 6K, and a scar mark indicating a metal to metal contact can be seen in FIGS. 6D, 6H, and 6L. The failure of the 0.5 wt. % CNT-loaded UHMWPE coating may be explained by the lower amount of CNTs in the UHMWPE polymer matrix causing an inefficient anchoring of the polymer chains and more material pull out, ultimately resulting in the failure of the coating.

Figure 4E:
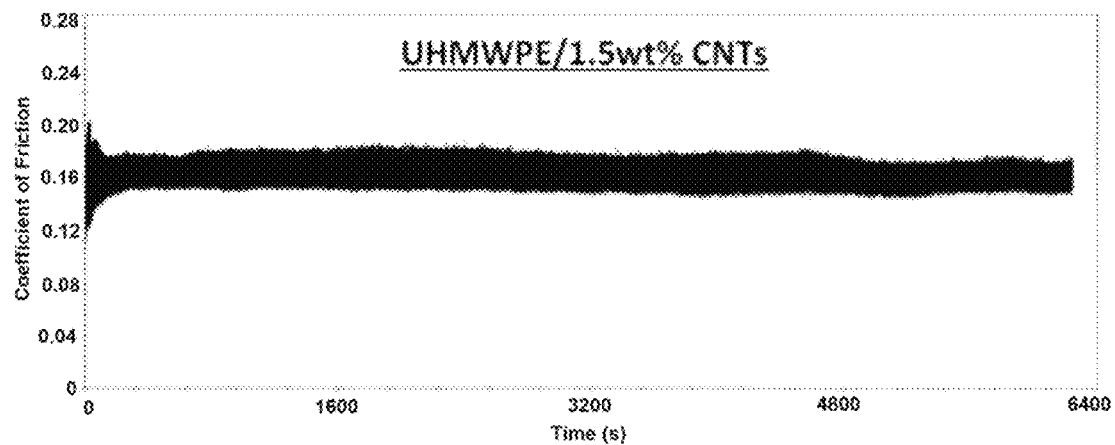
FIG. 4E shows a COF plot of a substrate coated with UHMWPE comprising 1.5 wt. % of CNTs after a wear test conducted at a normal load of 12 N and a sliding velocity of 0.1 m/s for 50,000 cycles (6276 seconds)
Figure 4F:
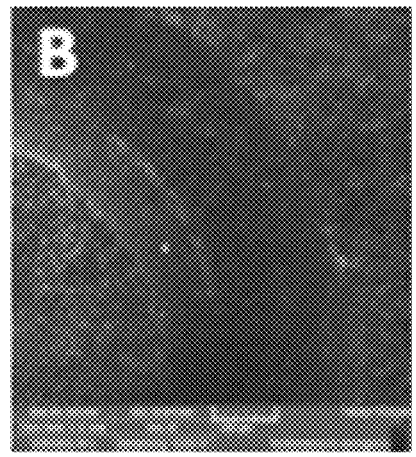
FIG. 4F shows an SEM image of the wear track from the coated substrate from FIG. 4E.
Figure 4G:
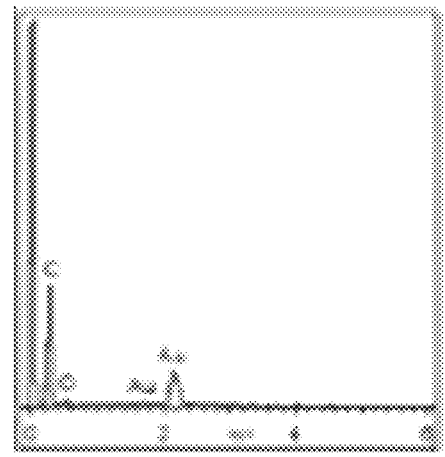
FIG. 4G shows an EDX spectrum of the region of the wear track from the coated substrate from FIG. 4E.
Figure 6A:
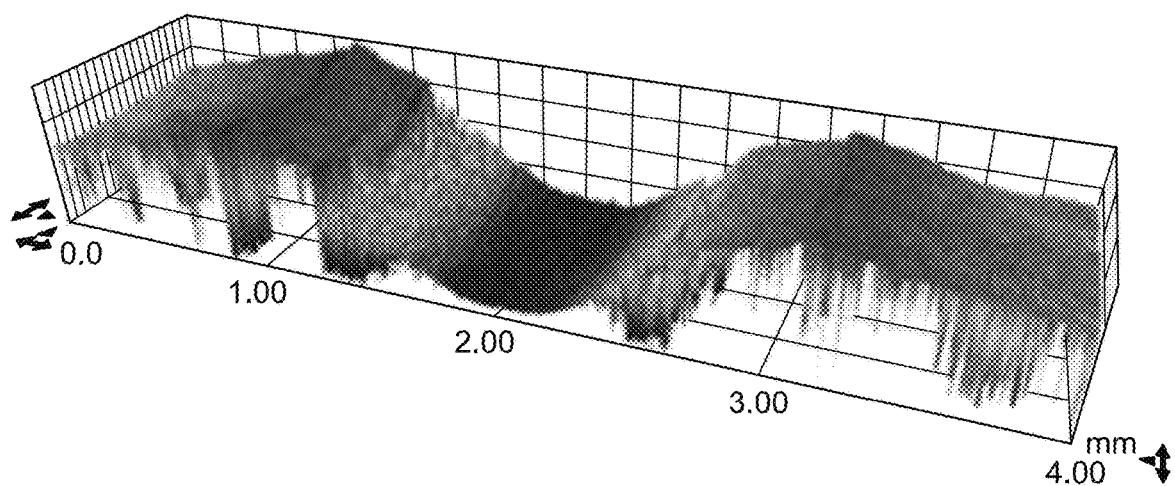
FIG. 6A shows 3-D and 2-D profiles of a substrate coated with UHMWPE comprising 0.5 wt. % of CNTs after a wear test conducted at a normal load of 12 N and a sliding velocity of 0.1 m/s for 50,000 cycles (6276 seconds)
Figure 6A:
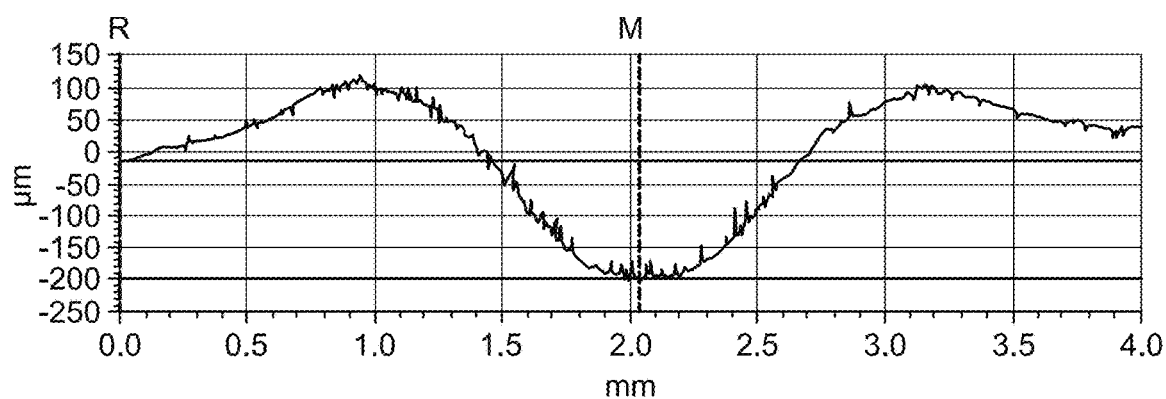
Figure 6D:
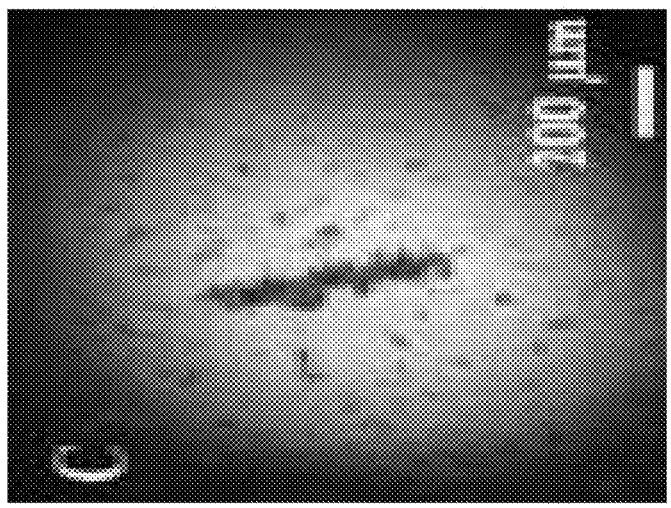
FIG. 6B to 6D show SEM images of the ball countersurface in the testing from FIG. 6A.
Figure 6C:
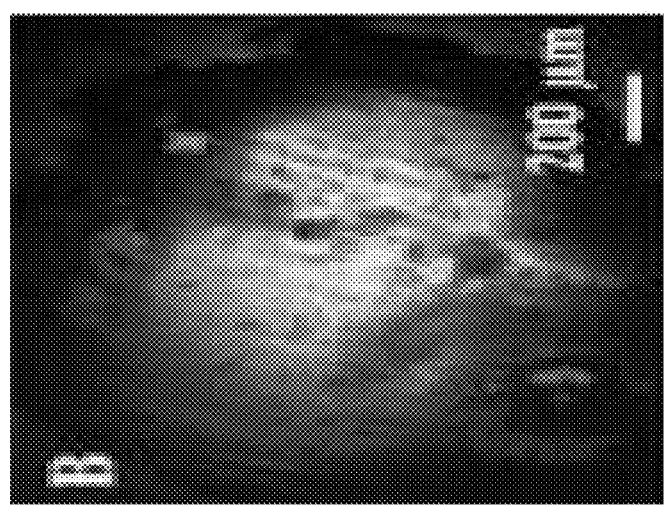
Figure 6B:
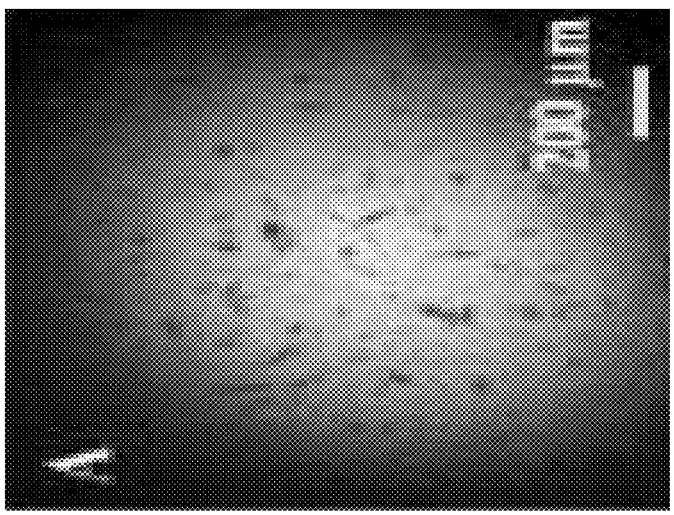
Figure 6E:
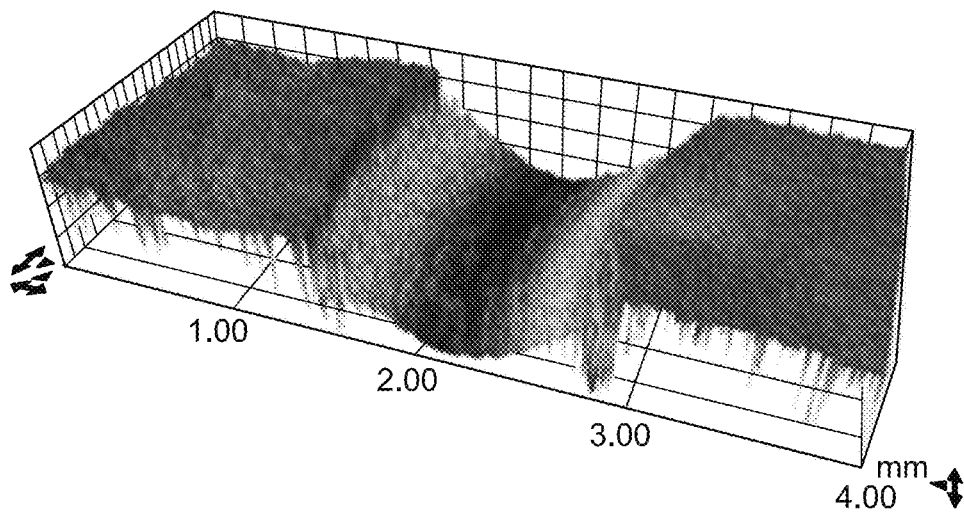
FIG. 6E shows 3-D and 2-D profiles of a substrate coated with UHMWPE comprising 1.5 wt. % of CNTs after a wear test conducted at a normal load of 12 N and a sliding velocity of 0.1 m/s for 50,000 cycles (6276 seconds)
Figure 6E:
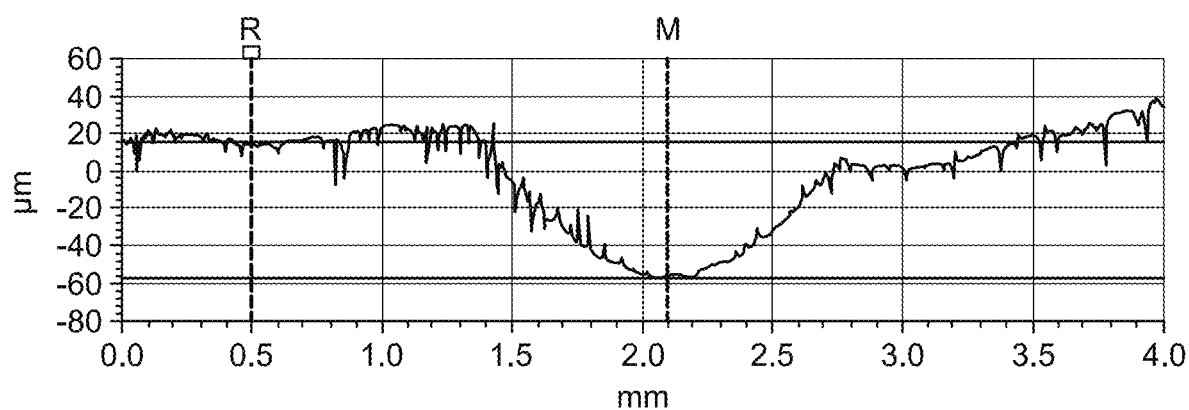
Figure 6H:
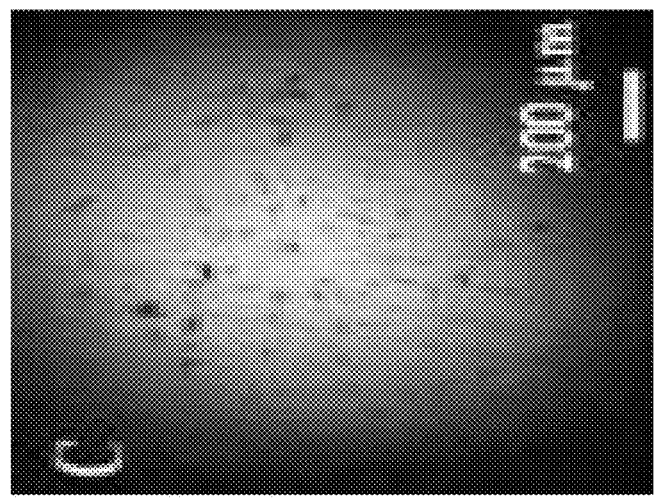
FIG. 6F to 6H show SEM images of the ball countersurface in the testing from FIG. 6E.
Figure 6G:
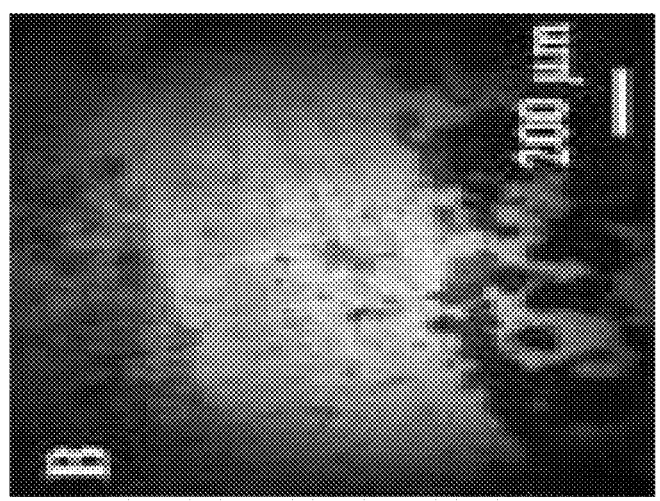
Figure 6F:
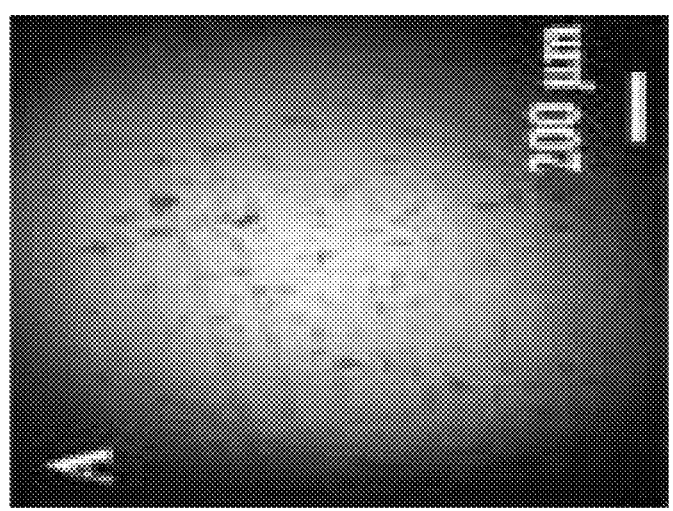
Figure 6I:
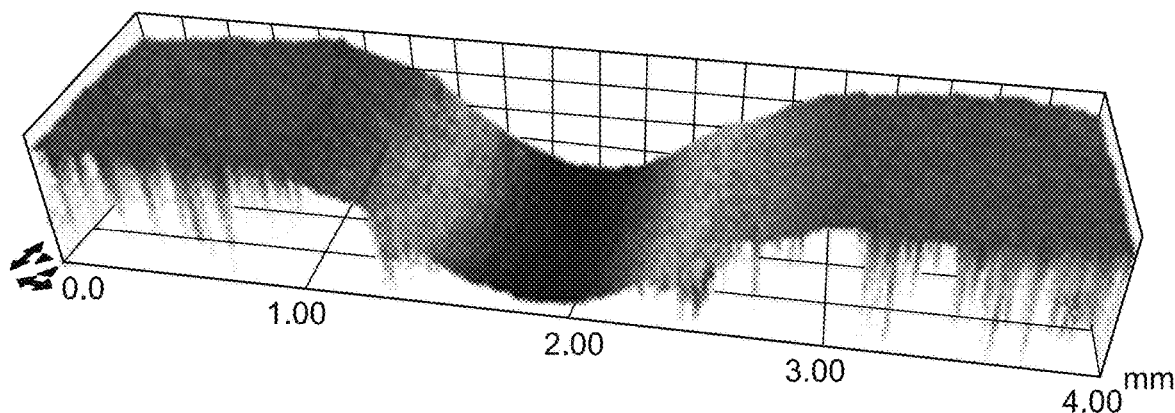
FIG. 6I shows 3-D and 2-D profiles of a substrate coated with UHMWPE comprising 3 wt. % of CNTs after a wear test conducted at a normal load of 12 N and a sliding velocity of 0.1 m/s for 50,000 cycles (6276 seconds)
Figure 6I:
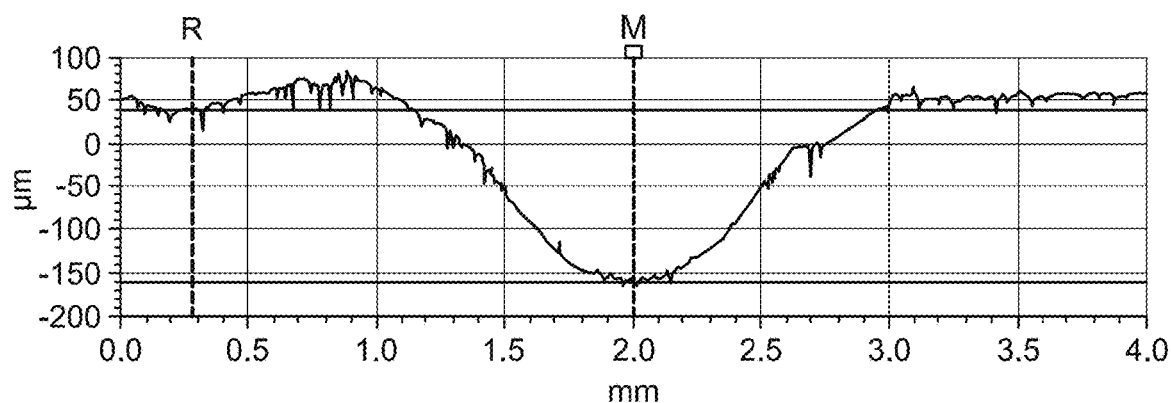
Figure 6L:
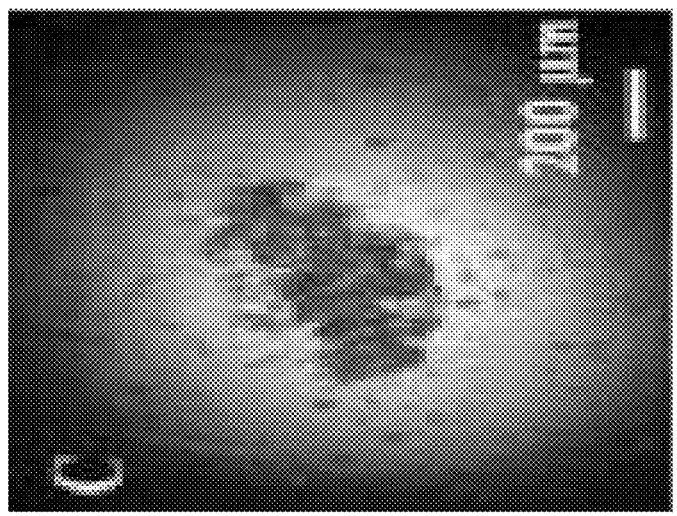
FIG. 6J to 6L show SEM images of the ball countersurface in the testing from FIG. 6I.
Figure 6K:
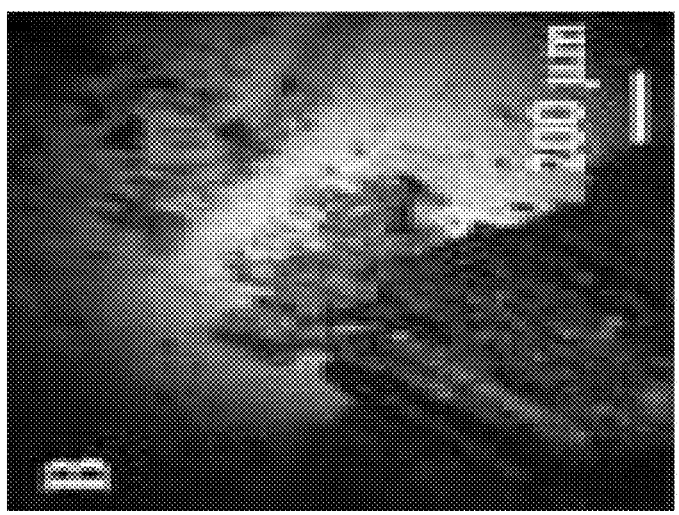
Figure 6J:
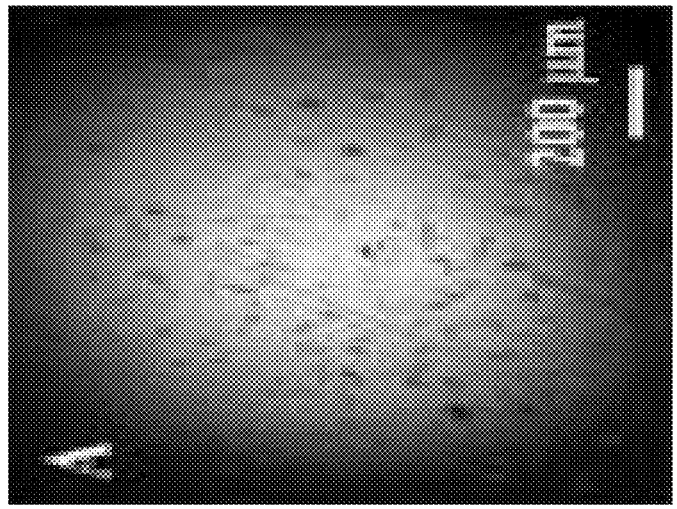

With a CNT loading of 1.5 wt. %, the UHMWPE nanocomposite coating fail only after 50,000 cycles as can be seen from FIG. 4E. The non-failure of the UHMWPE/1.5 wt. % CNT coating was also confirmed from the EDX spectrum conducted on the wear track shown in FIG. 4G and from the 2D profile of the wear track showing a wear track depth of ~72 µm seen in FIG. 4D, which is lower than the coating thickness. The optical images of the counterface ball in FIG. 6F to 6H show no scar marking, suggesting no metal to metal contact between the ball and the substrate. This improvement in the wear resistance of the nanocomposite coating may be attributed to the uniform distribution of the CNTs in the UHMWPE polymer matrix resulting in a good interaction between the matrix and the CNTs indicated by the SEM and Raman spectroscopy analysis, discussed above.

A CNT loading to 3 wt. % in the UHMWPE nanocomposite coating failed after ~7000 cycles. The failure of the coating was also indicated by the EDX spectrum of the wear track shown in FIG. 4J and the 2D profile of the wear track in FIG. 4I, which shows a wear track depth of ~196 µm which is greater than the coating thickness. The optical images of the counterface ball also shows a scar mark seen in FIG. 6K to 6L indicate a metal to metal contact. This sudden deterioration in the tribological performance of the nanocomposite coating with an increase in the loading of CNTs to 3 wt. % may be attributed to the agglomeration of CNTs in and/or on the UHMWPE matrix as detected in the Raman spectroscopy results in FIG. 1 and the SEM image in FIG. 2C, discussed above. Agglomerated CNTs in the polymer matrix may create hard and soft phases in the coating, and thus an uneven morphology, which may consequently result in coating failure, i.e., breach and/or rupture.

From the wear tests conducted on the coating comprising UHMWPE loaded with 0.5, 1.5, and 3 wt. % of CNTs, described above, it was indicated that a loading of 1.5±0.05, 0.1, 0.15, 0.2, 0.25, 0.3, 0.333, 0.35, 0.375, 0.4, 0.425, 0.45, 0.475, 0.5, 0.55, 0.6, 0.667, 0.7, 0.75, 0.8, 0.85, or 0.9 wt. % of CNTs, i.e., a range including any of these endpoints, may have the best tribological performance at a normal load of 12 N and a sliding velocity of 0.1 m/s.

Figure 5A:
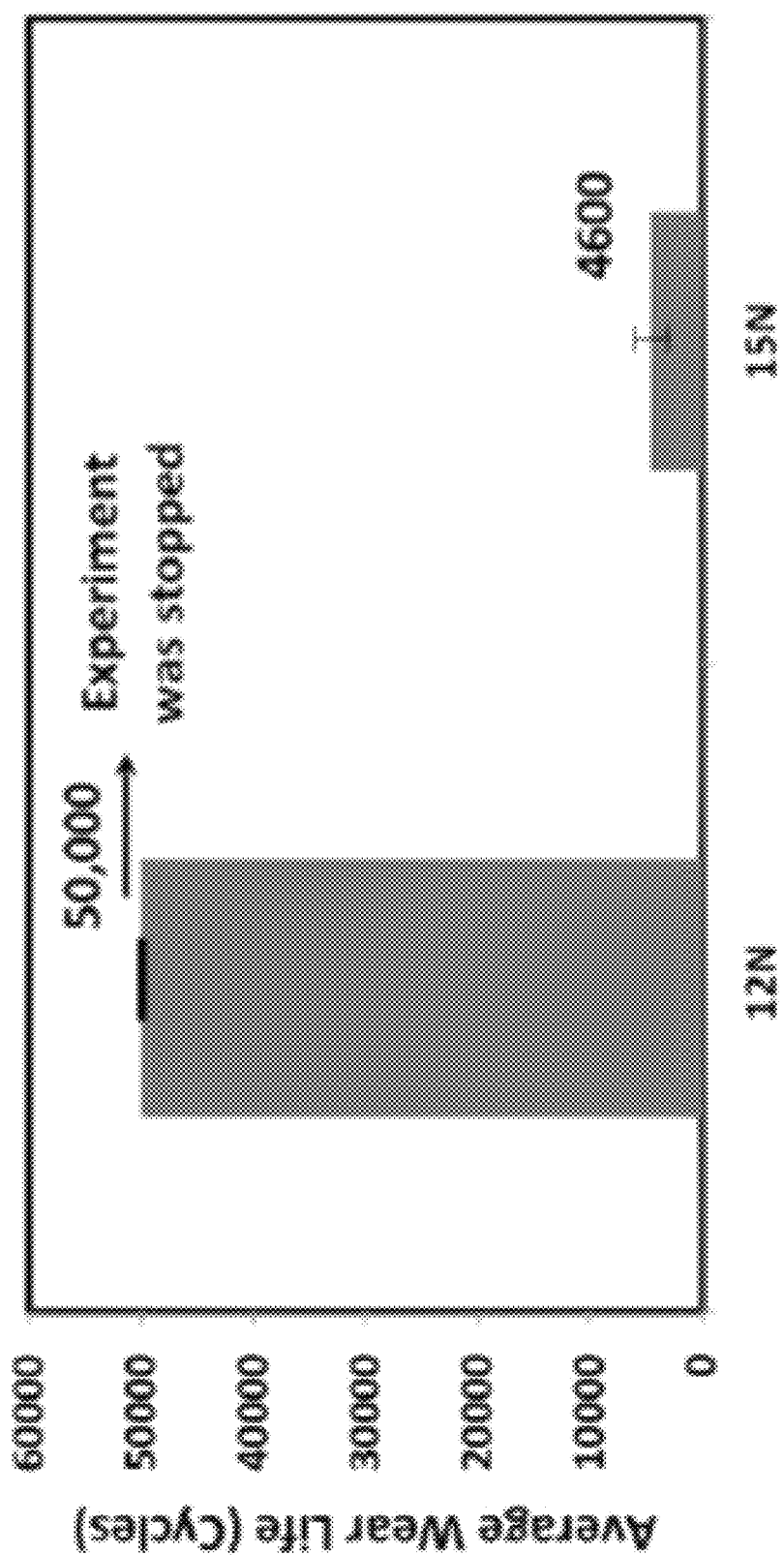
FIG. 5A shows a chart presenting the average wear life comparison from testing samples like those in FIG. 4E at two different normal loads, 12 N and 15 N.

To further evaluate the UHMWPE/1.5 wt % CNTs nanocomposite coating, wear tests were conducted at the same sliding velocity, i.e., 0.1 m/s, and a higher normal load of 15 N. FIG. 5A shows the average wear life of the UHMWPE/1.5 wt % CNT coating at normal loads of 12 and 15 N. FIG. 5A indicates that the UHMWPE/1.5 wt % CNT nanocomposite coating failed after ~4600 cycles at a normal load of 15 N, i.e., some 44000 cycles less than under 12 N force. This suggests at least a local critical region the working load for UHMWPE/1.5 wt % CNT 12±0.25, 0.5, 0.75, 1, 1.25, 1.5, 1.75, 2, 2.25, or 2.5 N at a linear speed around 0.1 m/s, i.e., ±0.025, 0.05, 0.075, 0.1, 0.125, 0.15, 0.175, 0.2, 0.225, 0.25, 0.275, 0.3, or 0.333 m/s, or any combination of these force and/or speed endpoints. FIG. 5B to 5D show the development of the coefficient of friction over time for the UHMWPE/1.5 wt % CNT coating under 15 N force.

Hybrid Nanocomposite Coating

A hybrid nanocomposite coating based on UHMWPE/1.5 wt % CNT, further adding 0.5, 1.5, 3, and 5 wt. % loads of hydroxyapatite (HA), but keeping the CNTs content constant at 1.5 wt. %.

SEM Dispersion Analysis of Ha-(1.5 Wt. %) CNT-UHMWPE

Figure 7A:
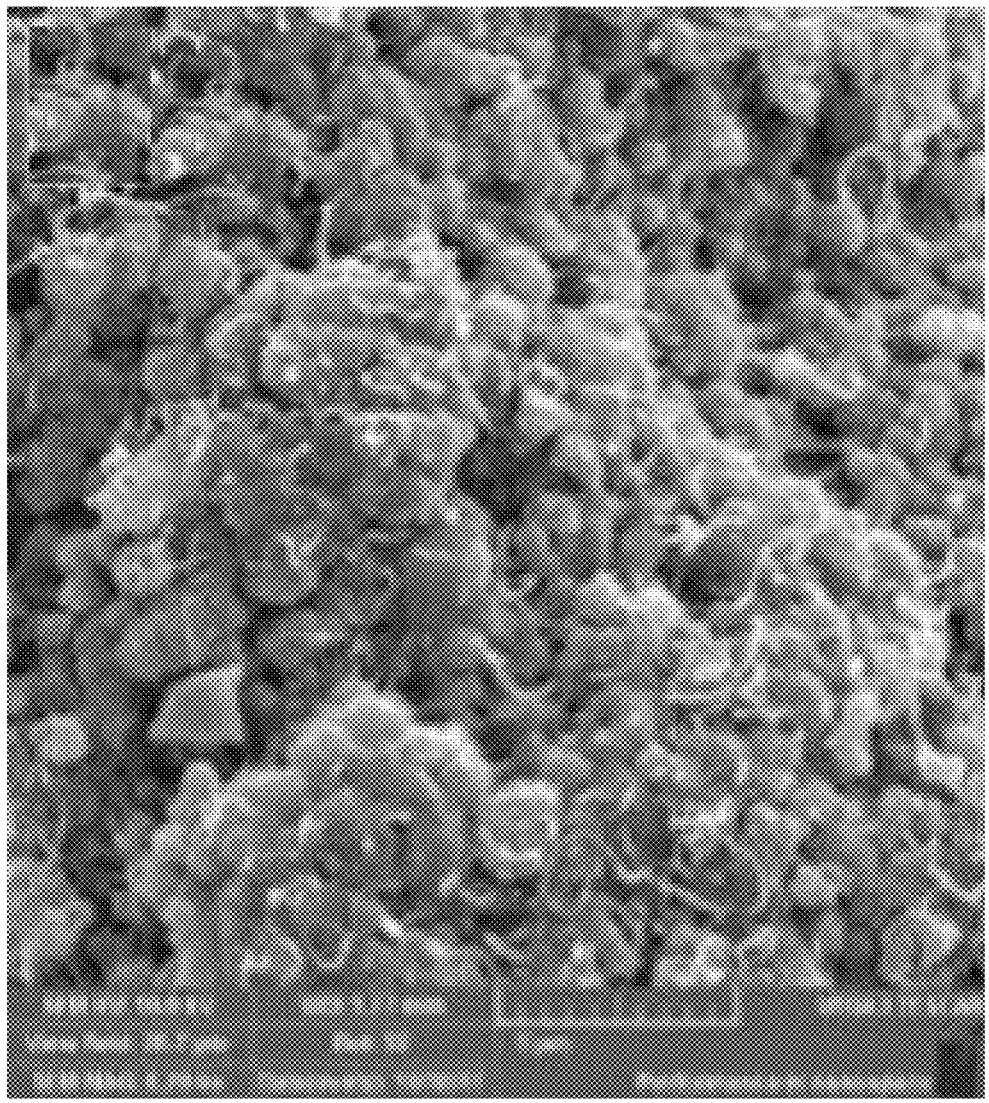
FIG. 7A shows an SEM image depicting the dispersion of CNTs in and/or on the coating comprising UHMWPE, 1.5 wt. % CNT, and 0.5 wt. % HA.
Figure 7B:
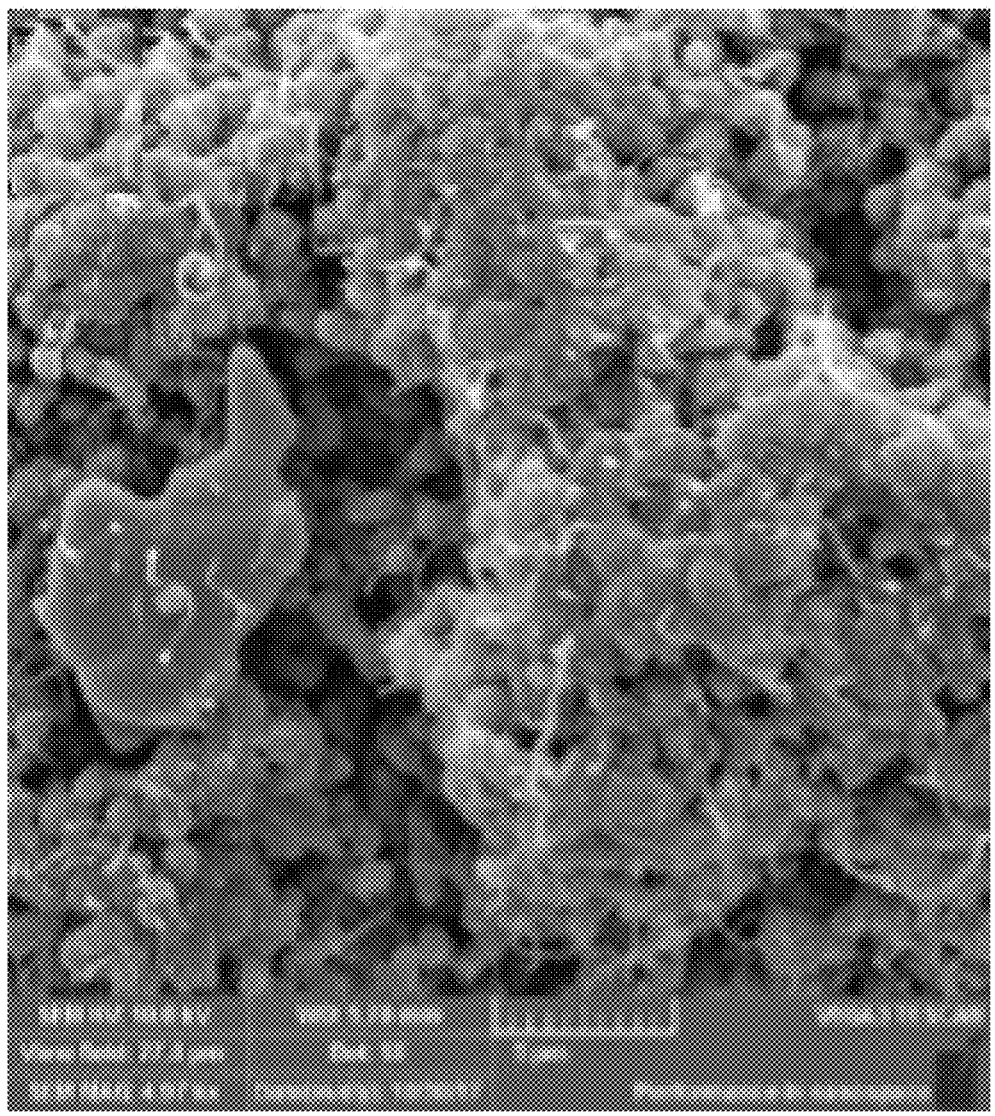
FIG. 7B shows an SEM image depicting the dispersion of CNTs in and/or on the coating comprising UHMWPE, 1.5 wt. % CNT, and 1.5 wt. % HA.
Figure 7C:
FIG. 7C shows an SEM image depicting the dispersion of CNTs in and/or on the coating comprising UHMWPE, 1.5 wt. % CNT, and 3 wt. % HA.
Figure 7D:
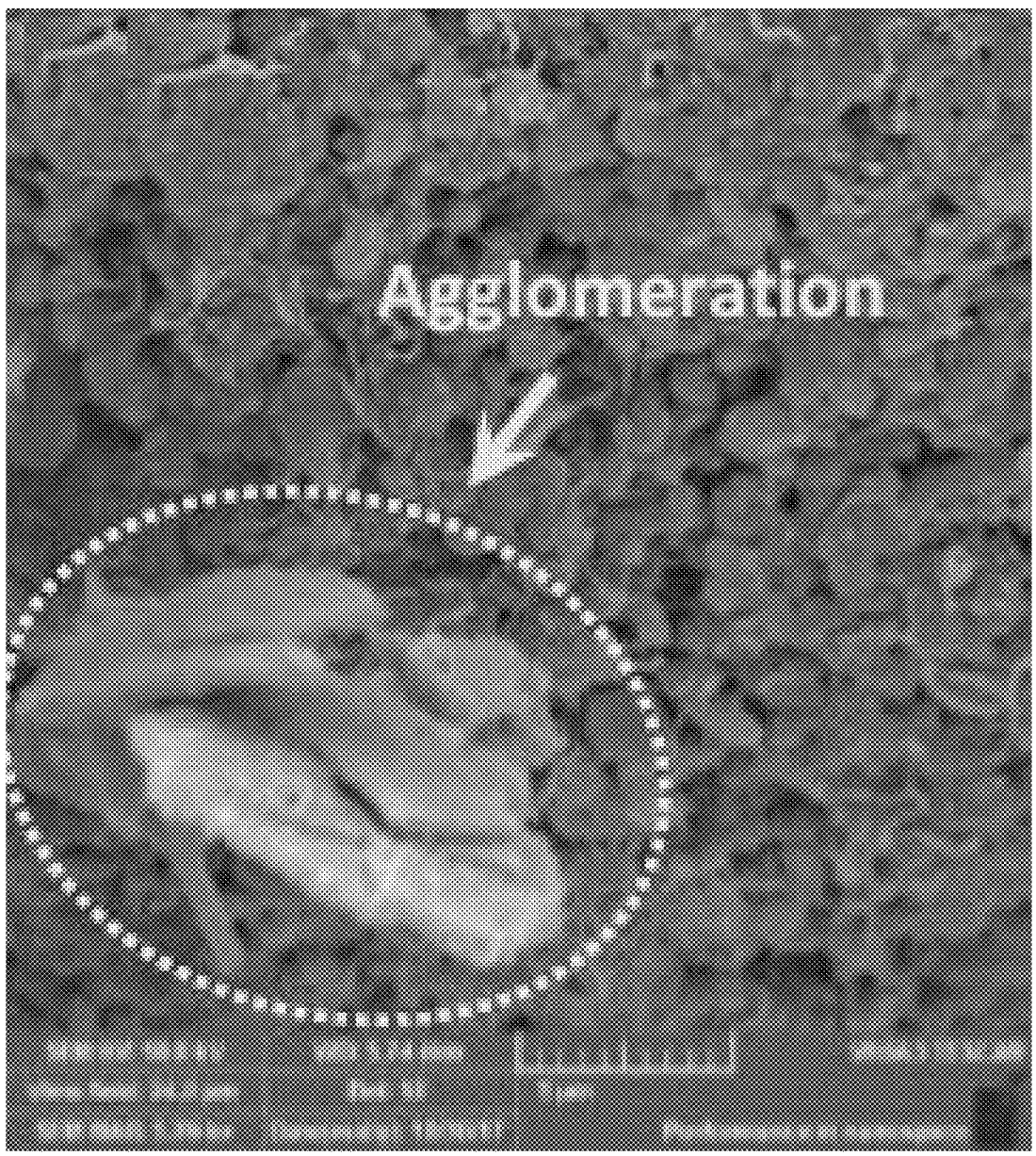
FIG. 7D shows an SEM image depicting the dispersion of CNTs in and/or on the coating comprising UHMWPE, 1.5 wt. % CNT, and 5 wt. % HA.

FIG. 7A to 7D show the SEM images of the UHMWPE/1.5 wt % CNT powders reinforced with 0.5, 1.5, 3, and 5 wt. % loadings of hydroxyapatite (HA). FIG. 7A to 7C indicate that the HA platelets are disentangled, resulting in their uniform dispersion without any agglomerates. At an HA loading of 5 wt. %, HA agglomerates were observed as seen in FIG. 7D.

Tribological Characterization of UHMWPE-CNT-HA Coating Hydroxyapatite loadings of 0.5, 1.5, 3, 5 wt. % were integrated into the UHMWPE/1.5 wt % CNT matrix, seeking to improve the bioactivity and osteocoductivity of the coating. Methods of modifying mechanical properties with additives such as HA in polymers, such as UHMWPE, are described in *Biomaterials* 2006, 27, 3701-3707, and *Advances in Materials Science and Implant Orthopedic Surgery*, R. Kossowsky and N. Kossovsky (eds), Springer: Berlin, 1995, which are incorporated by reference herein in their entirety. Mechanical and tribological properties of inventive hybrid nanocomposite coatings were explored by depositing on pure titanium substrates by the coating procedure set forth above, then running wear tests for 100,000 cycles (12552 seconds) at a normal load of 12N with a sliding velocity of 0.1 m/s. FIG. 8A to 8E shows the typical COF graphs, SEM images of wear track, EDX analysis, and the average wear life of the coatings for 100,000 cycles.

Figure 8A:
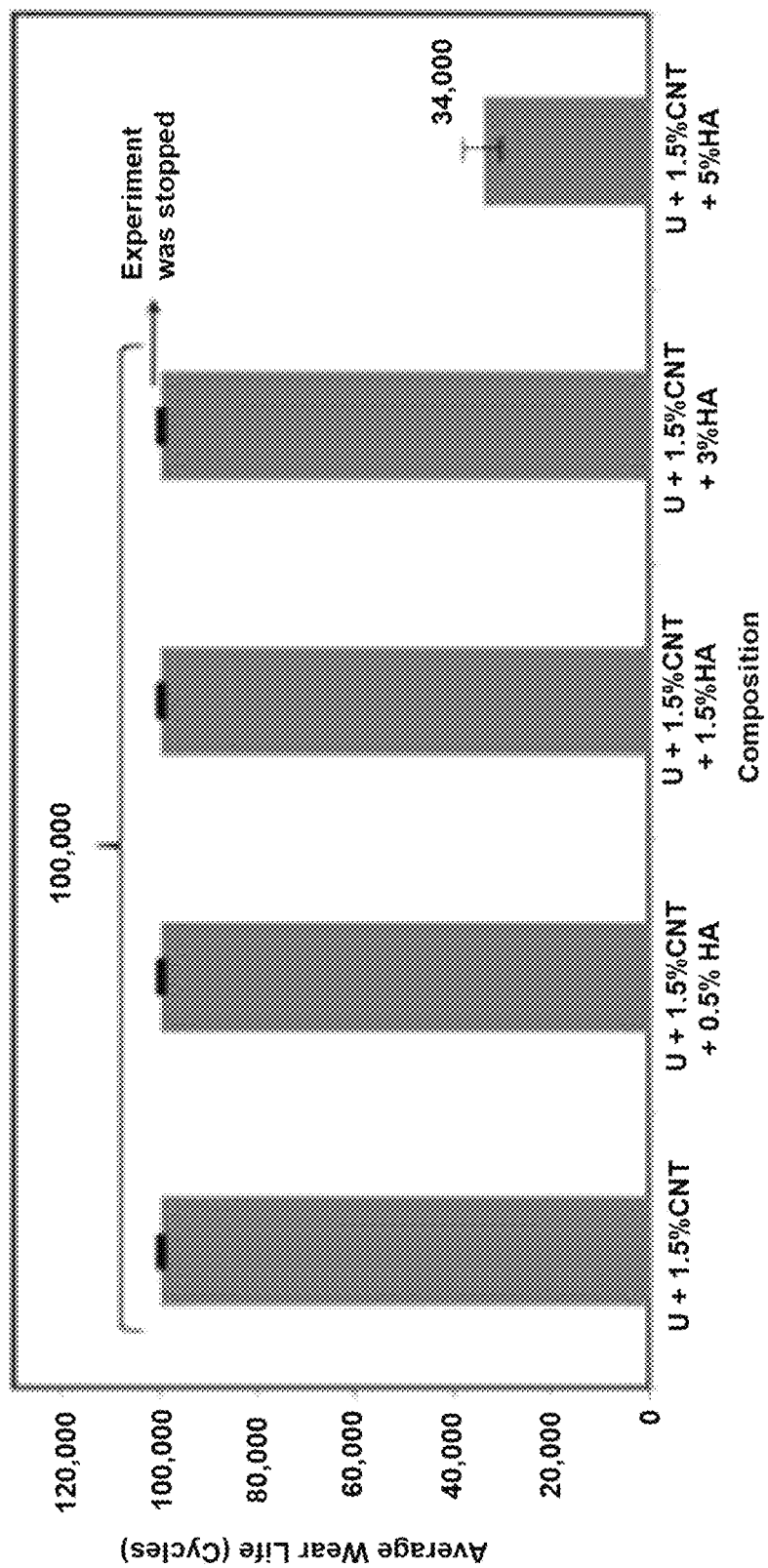
FIG. 8A shows a chart presenting the average wear life as a function of normal load of a substrate coated with UHMWPE comprising 1.5 wt. % CNT and different amounts of HA.
Figure 8B:
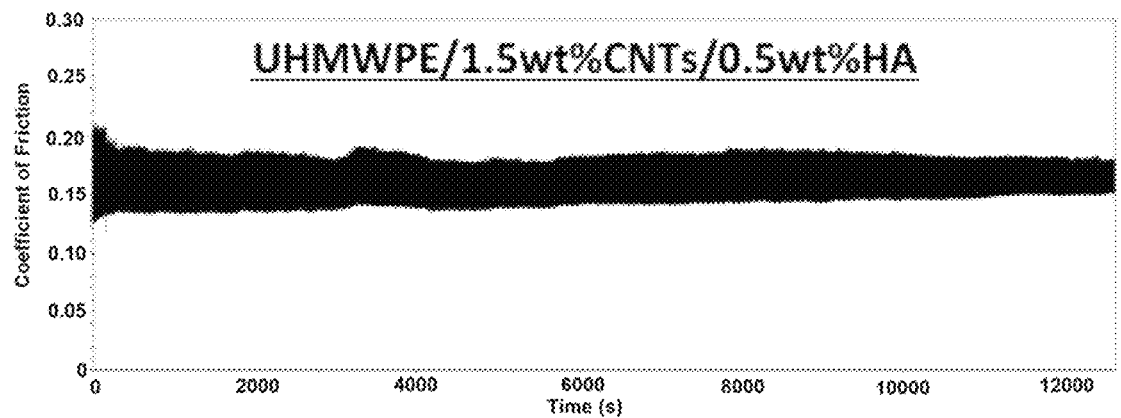
FIG. 8B shows a coefficient of friction (COF) plot of a substrate coated with UHMWPE comprising 1.5 wt. % of CNTs and 0.5 wt. % HA after a wear test conducted at a normal load of 12 N and a sliding velocity of 0.1 m/s for 100,000 cycles (12552 seconds)
Figure 8C:
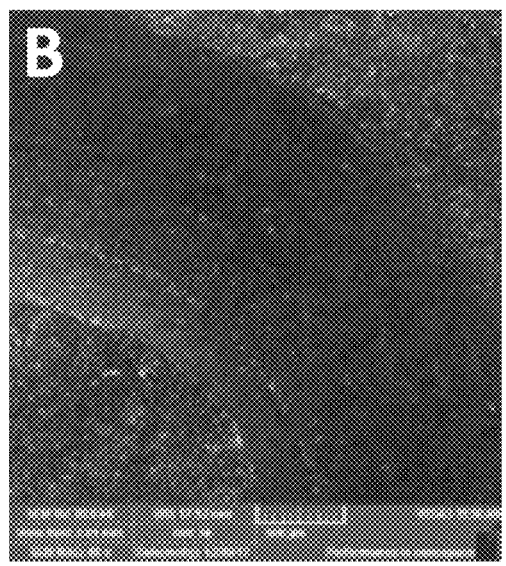
FIG. 8C shows an SEM image of the wear track from the coated substrate from FIG. 8B.
Figure 8D:
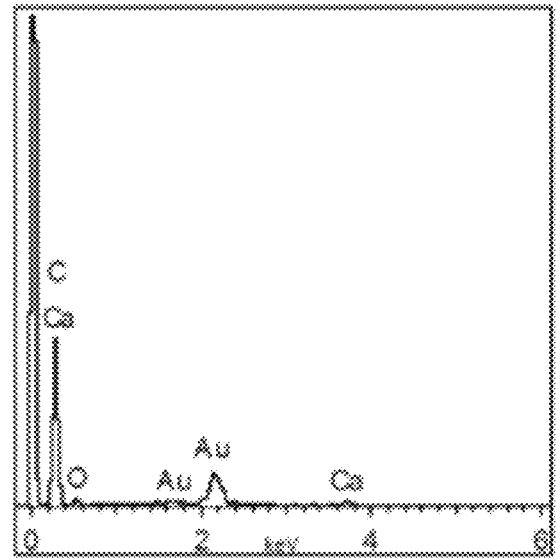
FIG. 8D shows an EDX spectrum of the region of the wear track from the coated substrate from FIG. 8B.
Figure 8E:
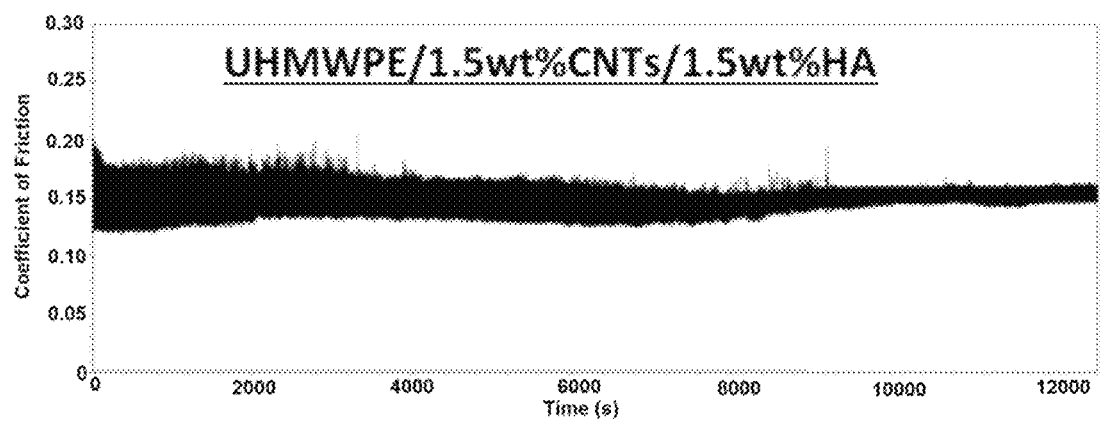
FIG. 8E shows a coefficient of friction (COF) plot of a substrate coated with UHMWPE comprising 1.5 wt. % of CNTs and 1.5 wt. % HA after a wear test conducted at a normal load of 12 N and a sliding velocity of 0.1 m/s for 100,000 cycles (12552 seconds)
Figure 8F:
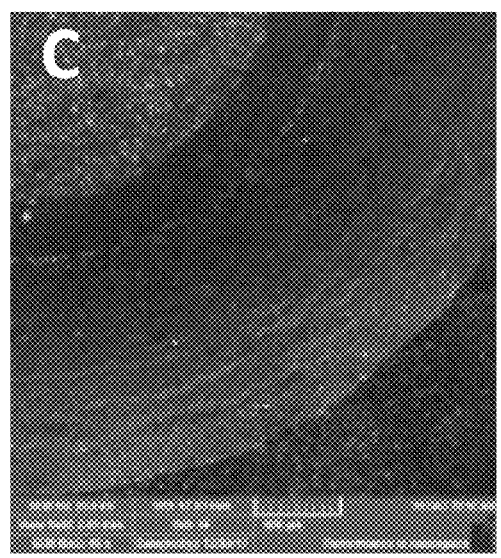
FIG. 8F shows an SEM image of the wear track from the coated substrate from FIG. 8E.
Figure 8G:
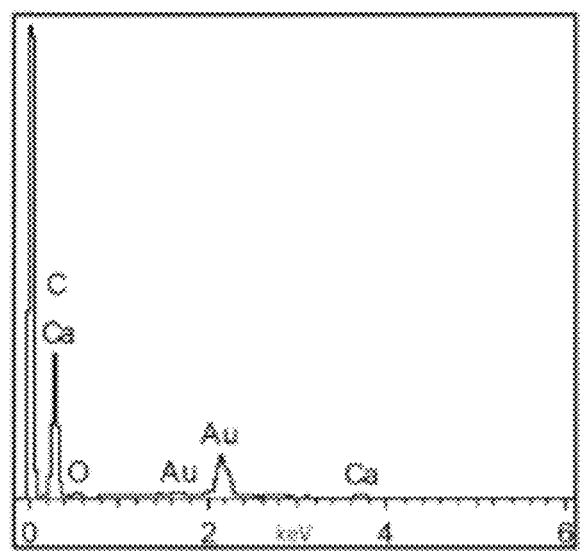
FIG. 8G shows an EDX spectrum of the region of the wear track from the coated substrate from FIG. 8E.
Figure 8H:
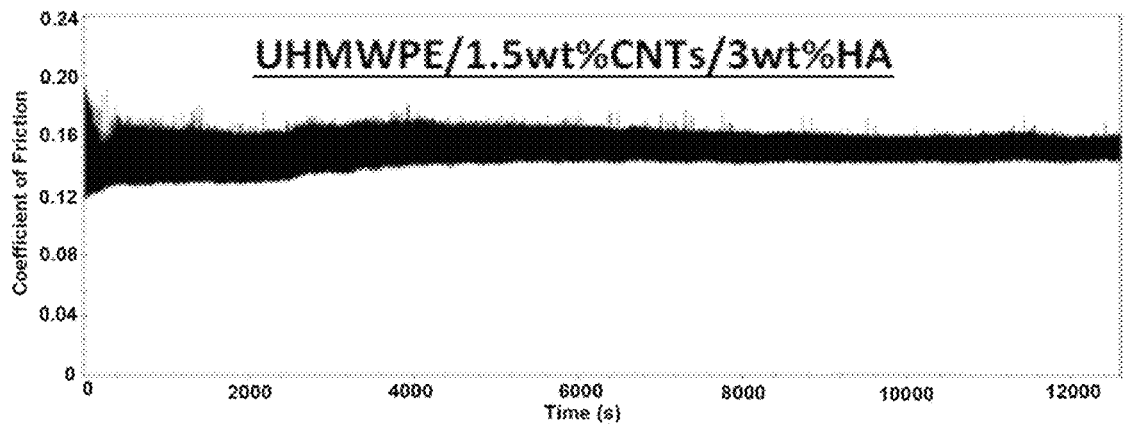
FIG. 8H shows a coefficient of friction (COF) plot of a substrate coated with UHMWPE comprising 3 wt. % of CNTs and 1.5 wt. % HA after a wear test conducted at a normal load of 12 N and a sliding velocity of 0.1 m/s for 100,000 cycles (12552 seconds)
Figure 8I:
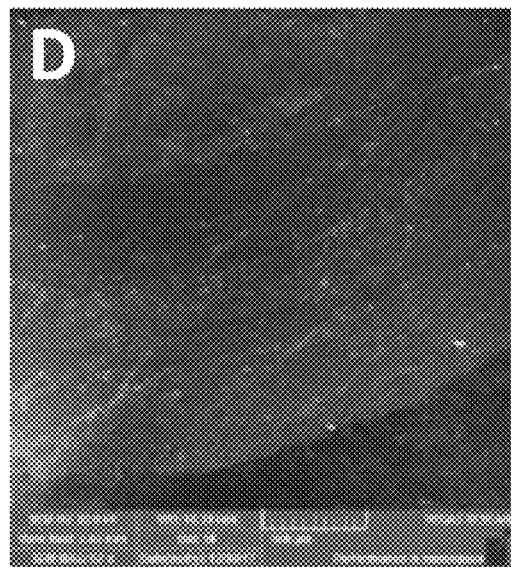
FIG. 8I shows an SEM image of the wear track from the coated substrate from FIG. 8H.
Figure 8J:
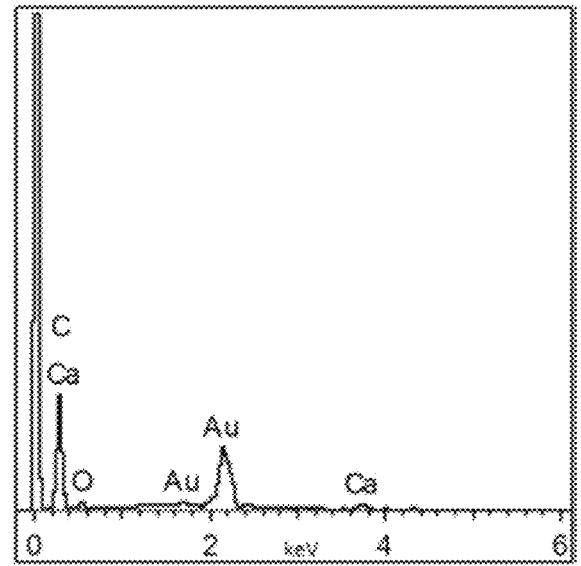
FIG. 8J shows an EDX spectrum of the region of the wear track from the coated substrate from FIG. 8H.
Figure 8K:
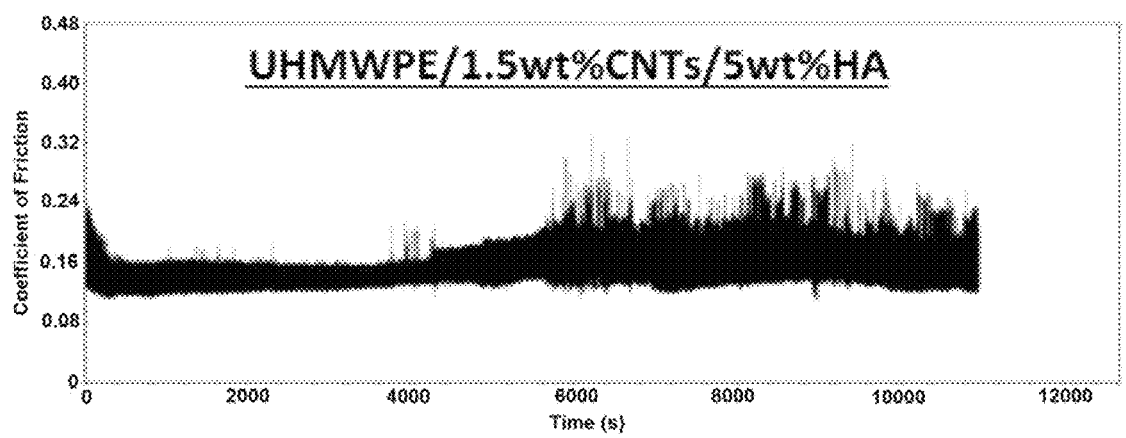
FIG. 8K shows a coefficient of friction (COF) plot of a substrate coated with UHMWPE comprising 1.5 wt. % of CNTs and 5 wt. % HA after a wear test conducted at a normal load of 12 N and a sliding velocity of 0.1 m/s for 100,000 cycles (12552 seconds)
Figures 8L, 8M:
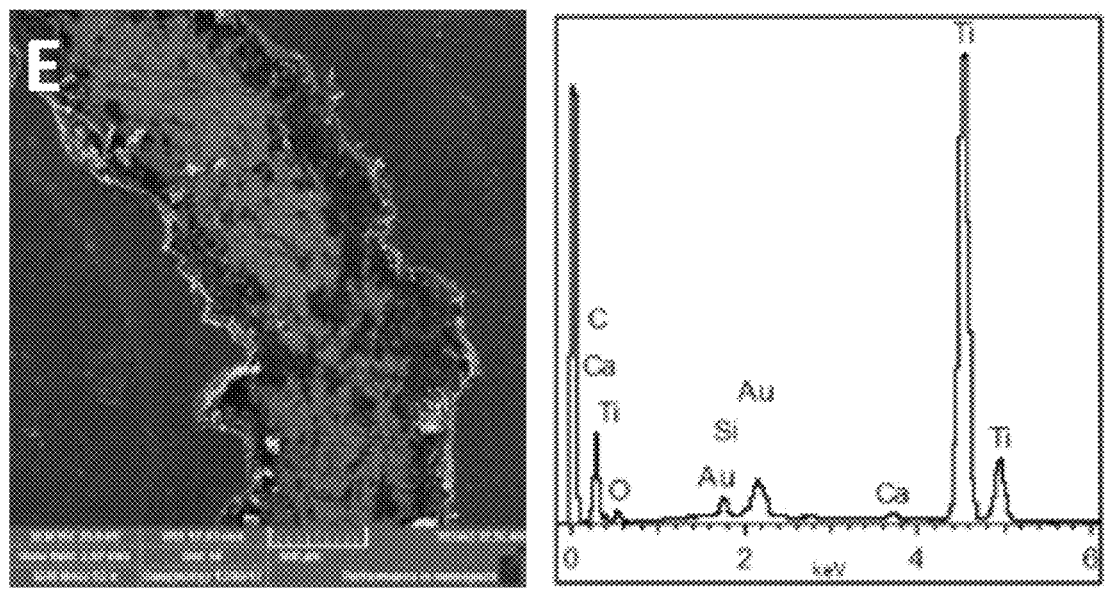
FIG. 8L shows an SEM image of the wear track from the coated substrate from FIG. 8K.
FIG. 8M shows an EDX spectrum of the region of the wear track from the coated substrate from FIG. 8K.

FIG. 8A shows test results of exemplary hybrid nanocomposite coatings of UHMWPE/1.5 wt % CNTs reinforced with 0.5, 1.5, and 3 wt. % HA, whereby each completed the 100,000 cycle test without failure. By increasing the percentage of HA to 5 wt. %, failure of the coating resulted after ~34,000 cycles. The failure was supported by the insets, including the EDX spectrum in FIG. 8E, wherein the wear track is visible and a peak of Ti can be seen, indicating metal to metal contact. The failure of the 5 wt. % HA sample may be attributed to the agglomerations and the pile up of HA plates as seen in the SEM image in FIG. 7D. The agglomerations of the HA may result in non-uniform properties throughout the polymer matrix, potentially causing material pull-out and high wear.

Since the coatings of UHMWPE with 1.5 wt. % CNTs reinforced with 0.5, 1.5, and 3 wt. % of HA did not fail at 100,000 cycles (12552 seconds), to ascertain wear resistance of these hybrid nanocomposite coating for prolonged durations, these 0.5, 1.5, and 3 wt. % HA coatings were further tested for a 250,000 cycles (31380 seconds), at a load of 12 N and a sliding velocity of 0.1 m/s. SEM images of the wear track along with the EDX spectrum, typical coefficient of friction (COF) graphs and the average wear life are shown in FIG. 9A to 9D for all the tested hybrid nanocomposite coatings after a wear test of 250,000 cycles.

Figure 9A:
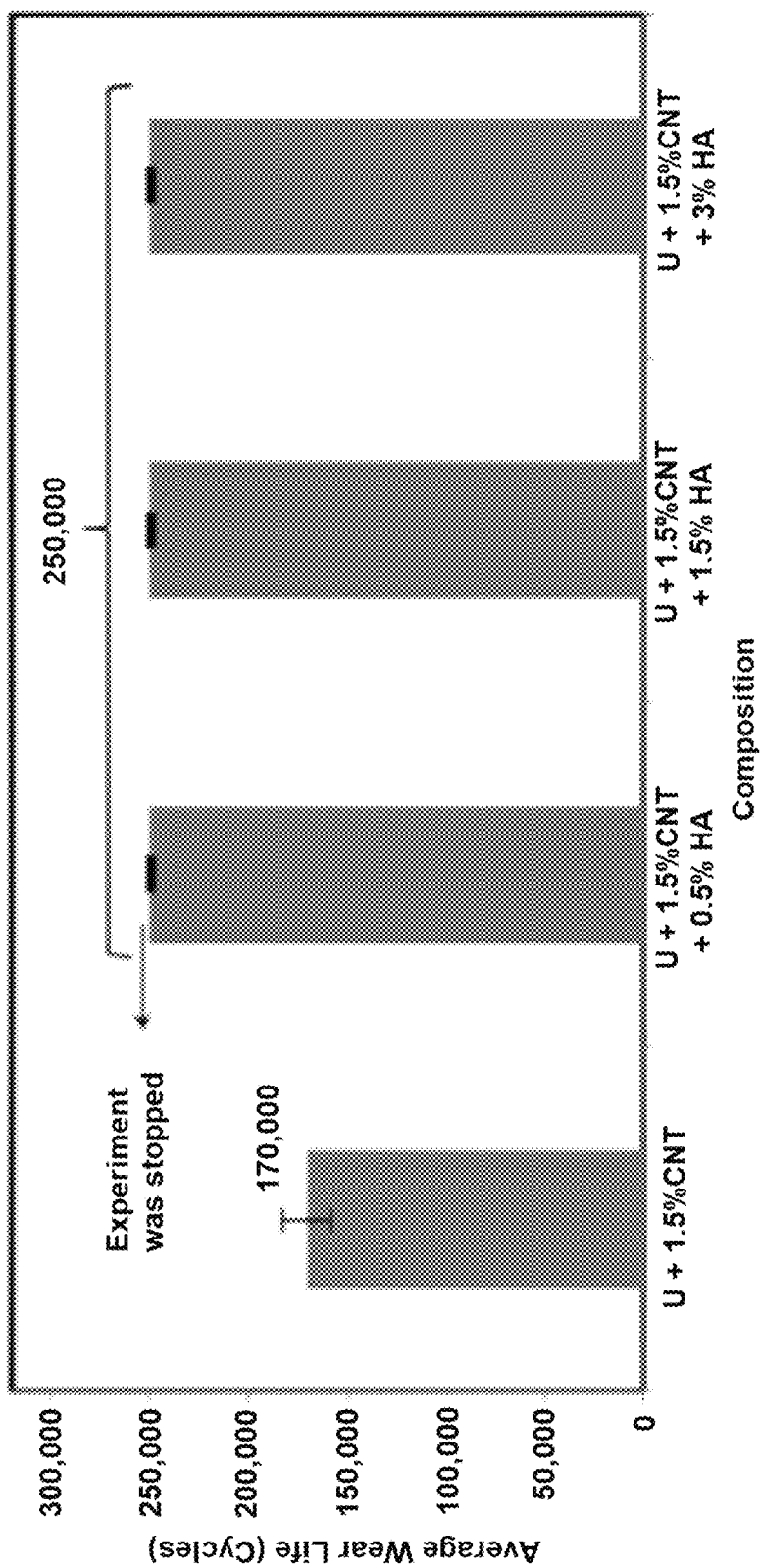
FIG. 9A shows a chart presenting the average wear life as a function of normal load of a substrate coated with UHMWPE comprising 1.5 wt. % CNT and different amounts of HA.
Figure 9B:
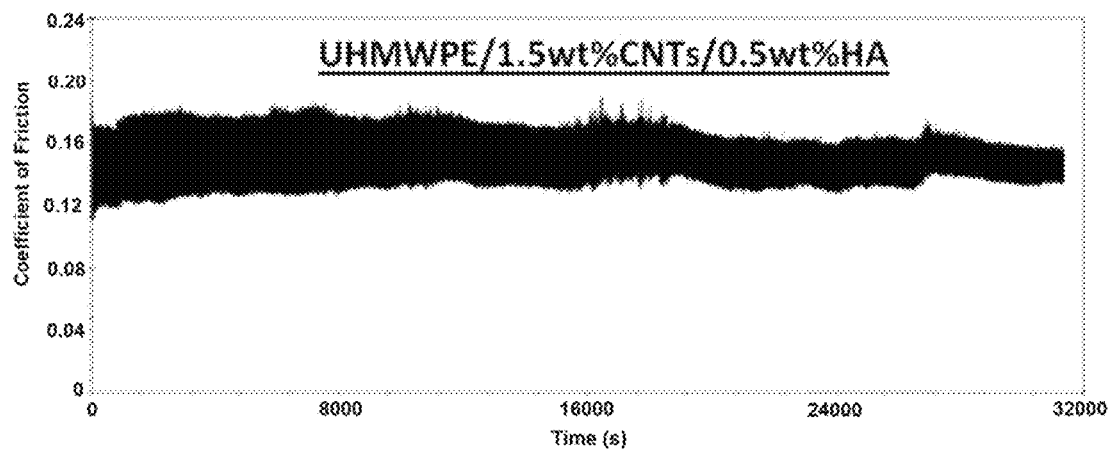
FIG. 9B to 9D show the COF graph, SEM image of the wear track, and EDX spectrum of a sample of the same type as shown in FIG. 8B wherein the wear test is conducted for 250,000 cycles (31380 seconds)
Figures 9C, 9D:
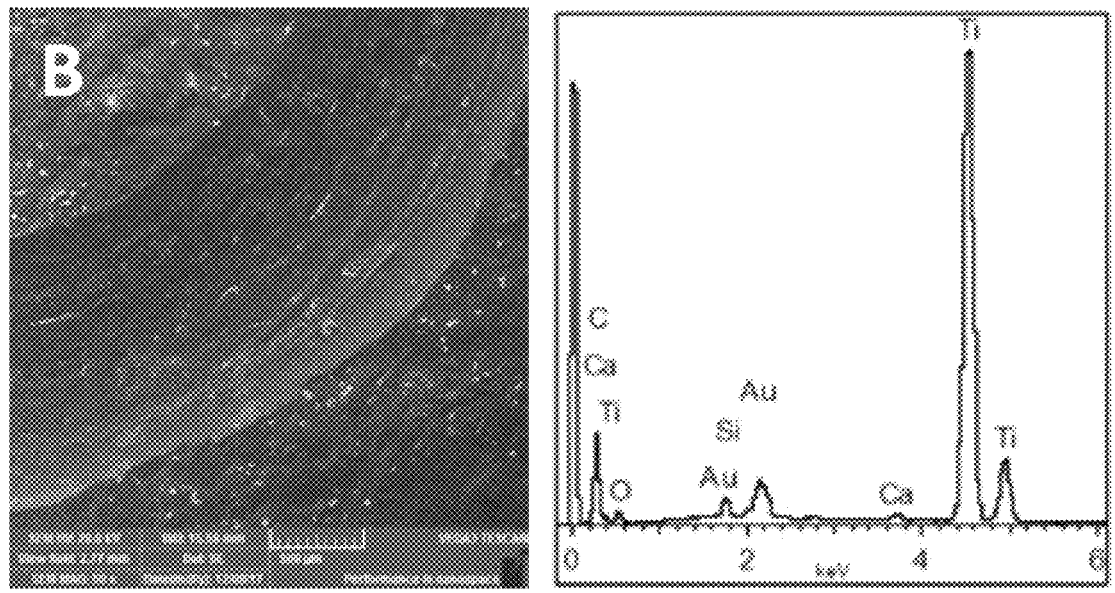
Figure 9H:
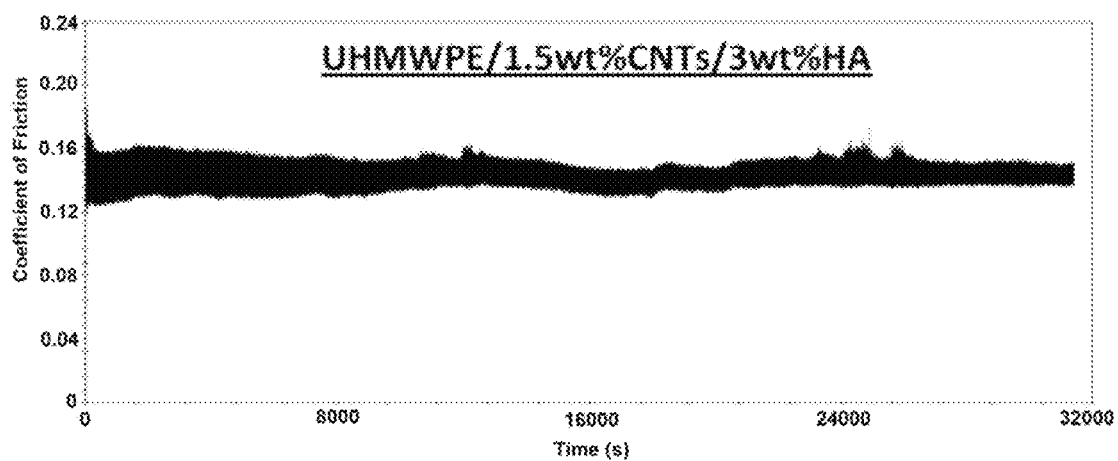
FIG. 9H to 9J show the COF graph, SEM image of the wear track, and EDX spectrum of a sample of the same type as shown in FIG. 8D wherein the wear test is conducted for 250,000 cycles (31380 seconds)
Figure 9I:
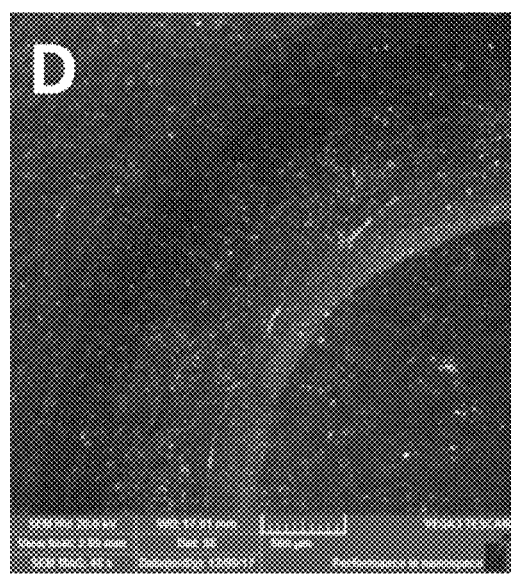
Figure 9J:
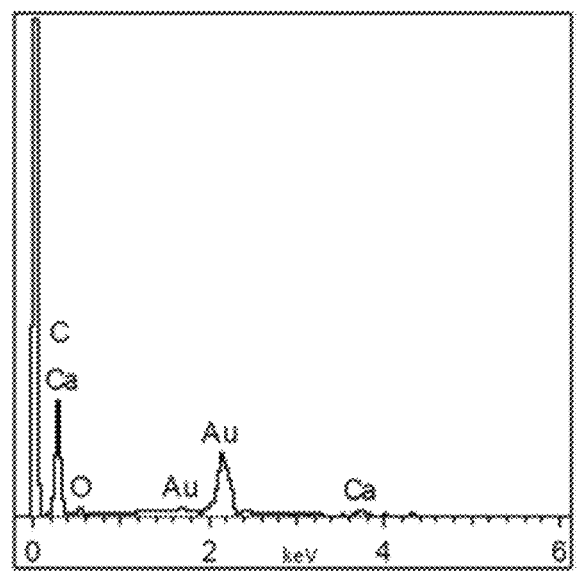
Figure 10A:
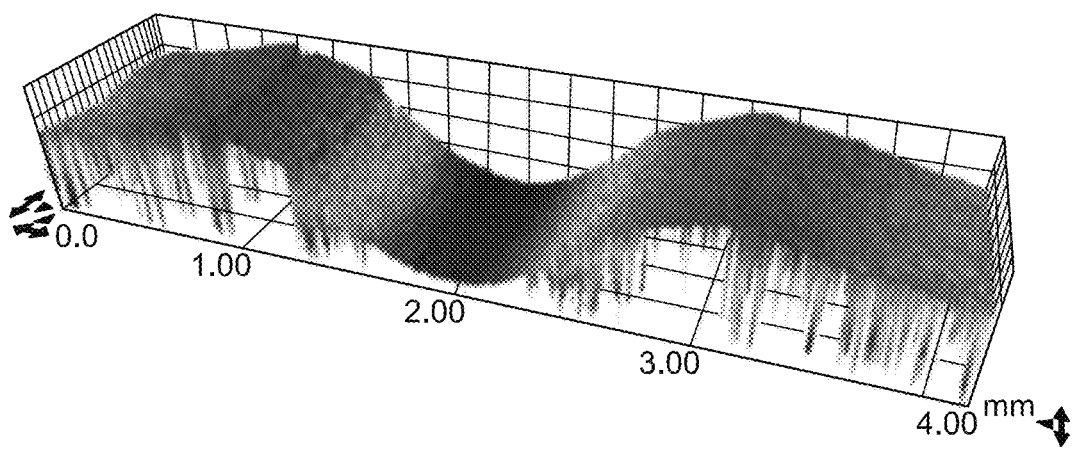
FIG. 10A shows 3-D and 2-D profiles of a substrate coated with UHMWPE comprising 1.5 wt. % of CNTs and 0.5 wt. % of HA after a wear test conducted at a normal load of 12 N and a sliding velocity of 0.1 m/s for 250,000 cycles (31380 seconds)
Figure 10A:
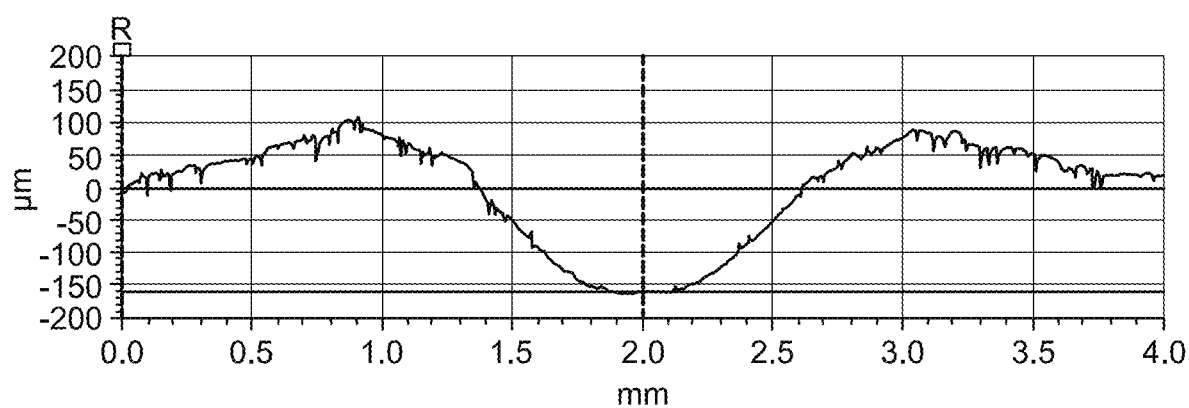
Figure 10D:
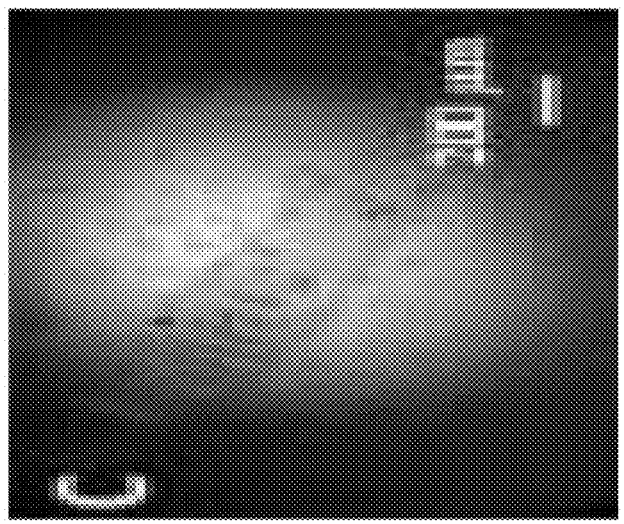
FIG. 10B to 10D show SEM images of the ball countersurface in the testing from FIG. 10A.
Figure 10C:
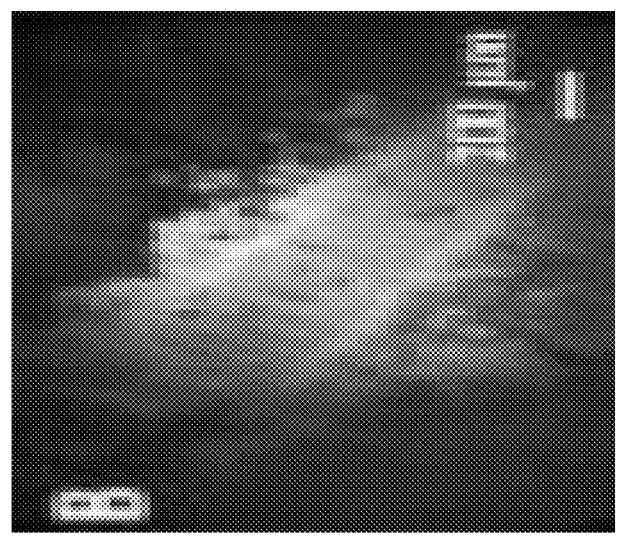
Figure 10B:
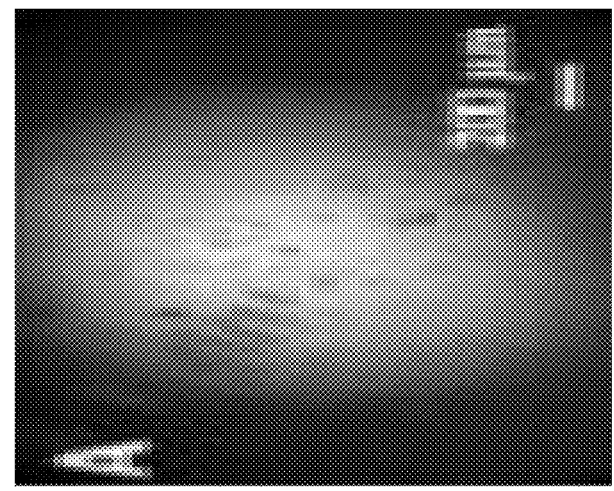
Figure 10E:
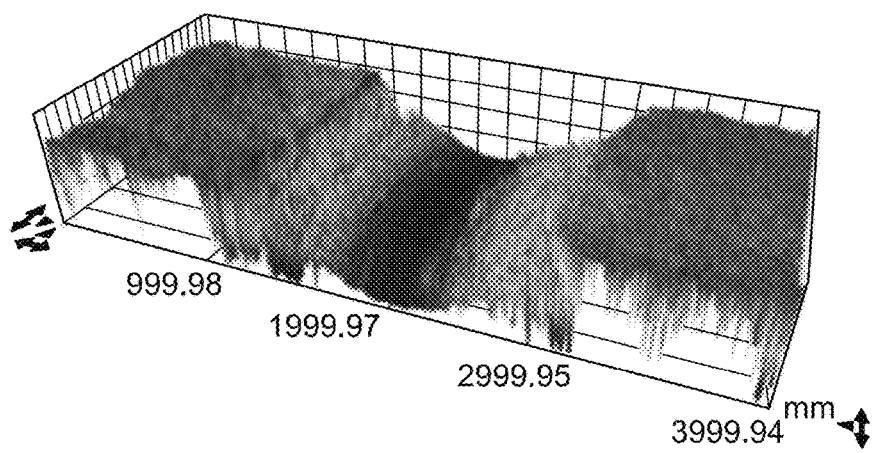
FIG. 10E shows 3-D and 2-D profiles of a substrate coated with UHMWPE comprising 1.5 wt. % of CNTs and 1.5 wt. % of HA after a wear test conducted at a normal load of 12 N and a sliding velocity of 0.1 m/s for 250,000 cycles (31380 seconds)
Figure 10E:
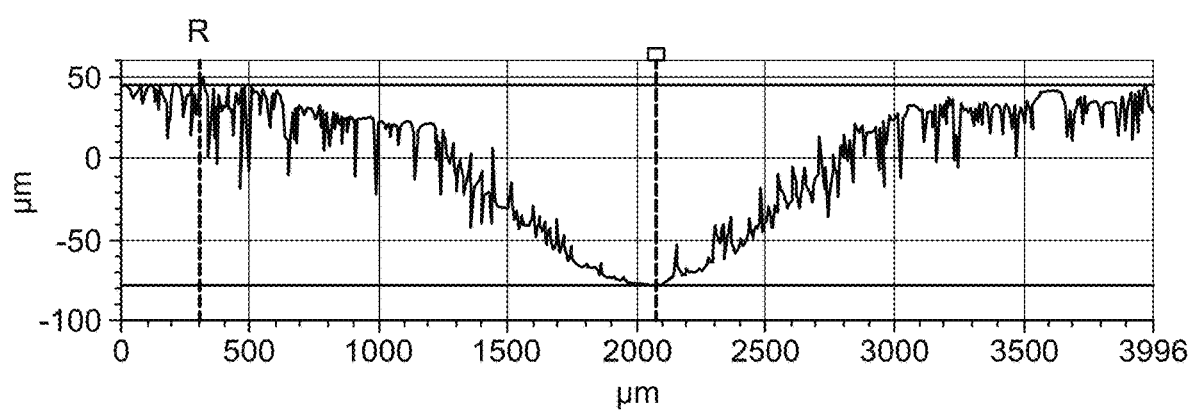
Figure 10H:
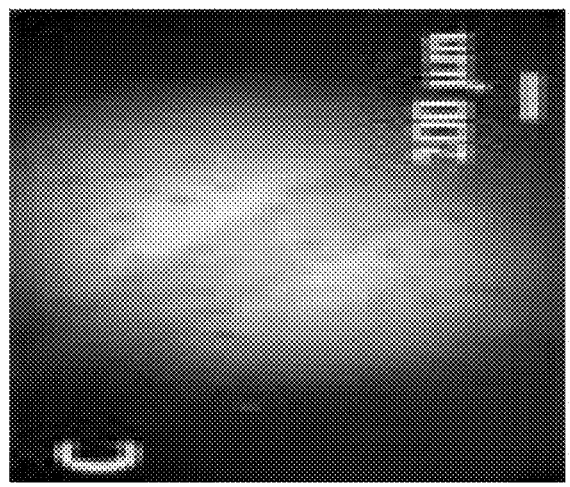
FIG. 10F to 10H show SEM images of the ball countersurface in the testing from FIG. 10E.
Figure 10G:
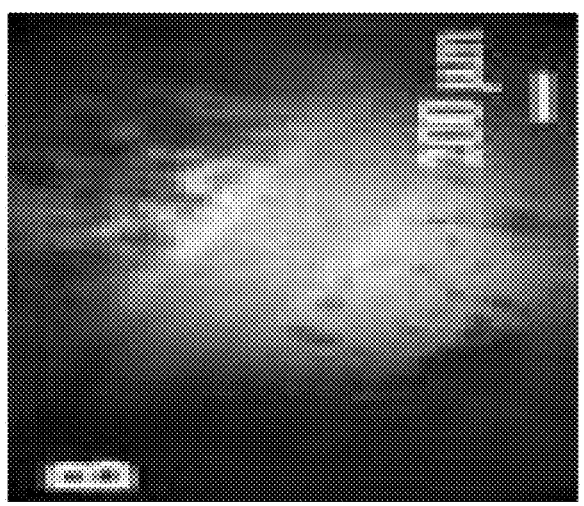
Figure 10F:
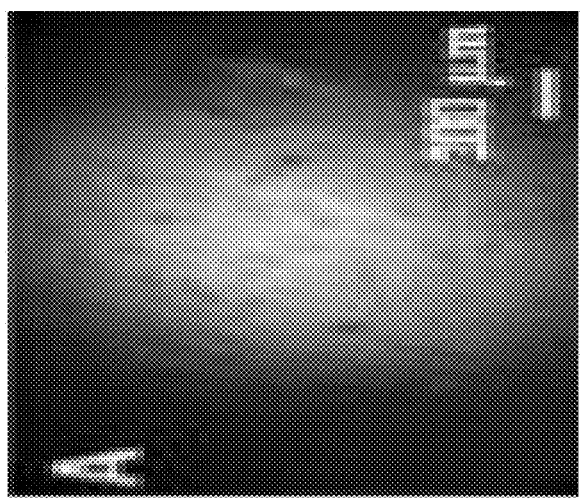
Figure 10I:
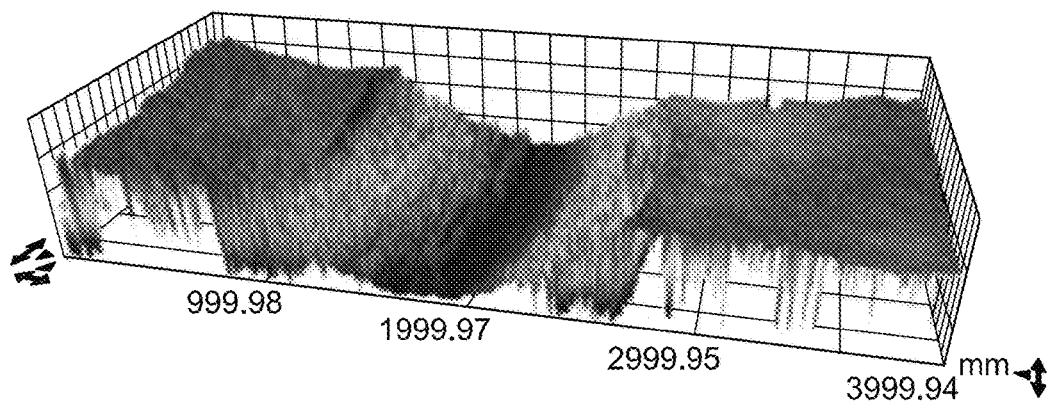
FIG. 10I shows 3-D and 2-D profiles of a substrate coated with UHMWPE comprising 1.5 wt. % of CNTs and 3 wt. % of HA after a wear test conducted at a normal load of 12 N and a sliding velocity of 0.1 m/s for 250,000 cycles 250,000 cycles (31380 seconds)
Figure 10I:
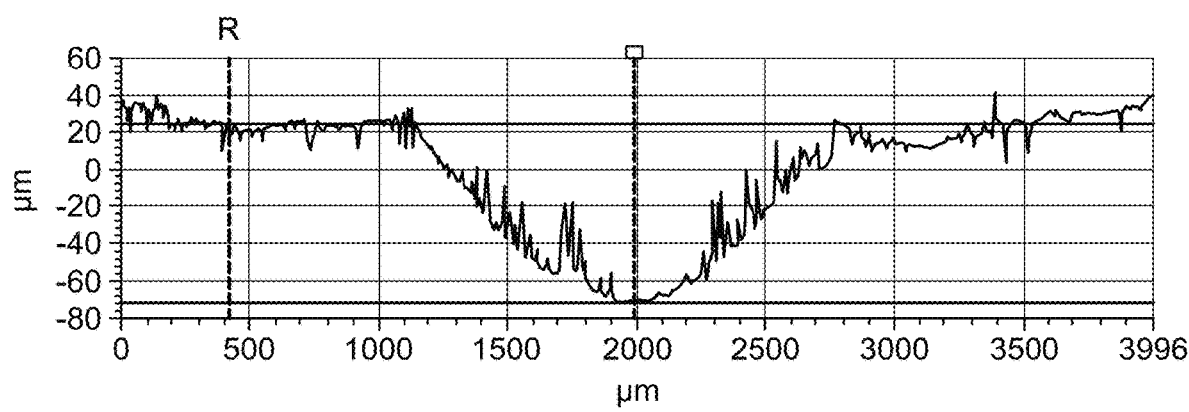
Figure 10L:
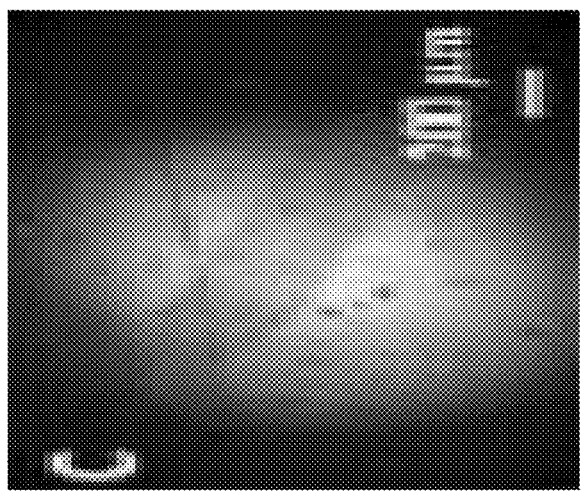
FIG. 10J to 10L show SEM images of the ball countersurface in the testing from FIG. 10I.
Figure 10K:
Figure 10J:
Figure 11A:
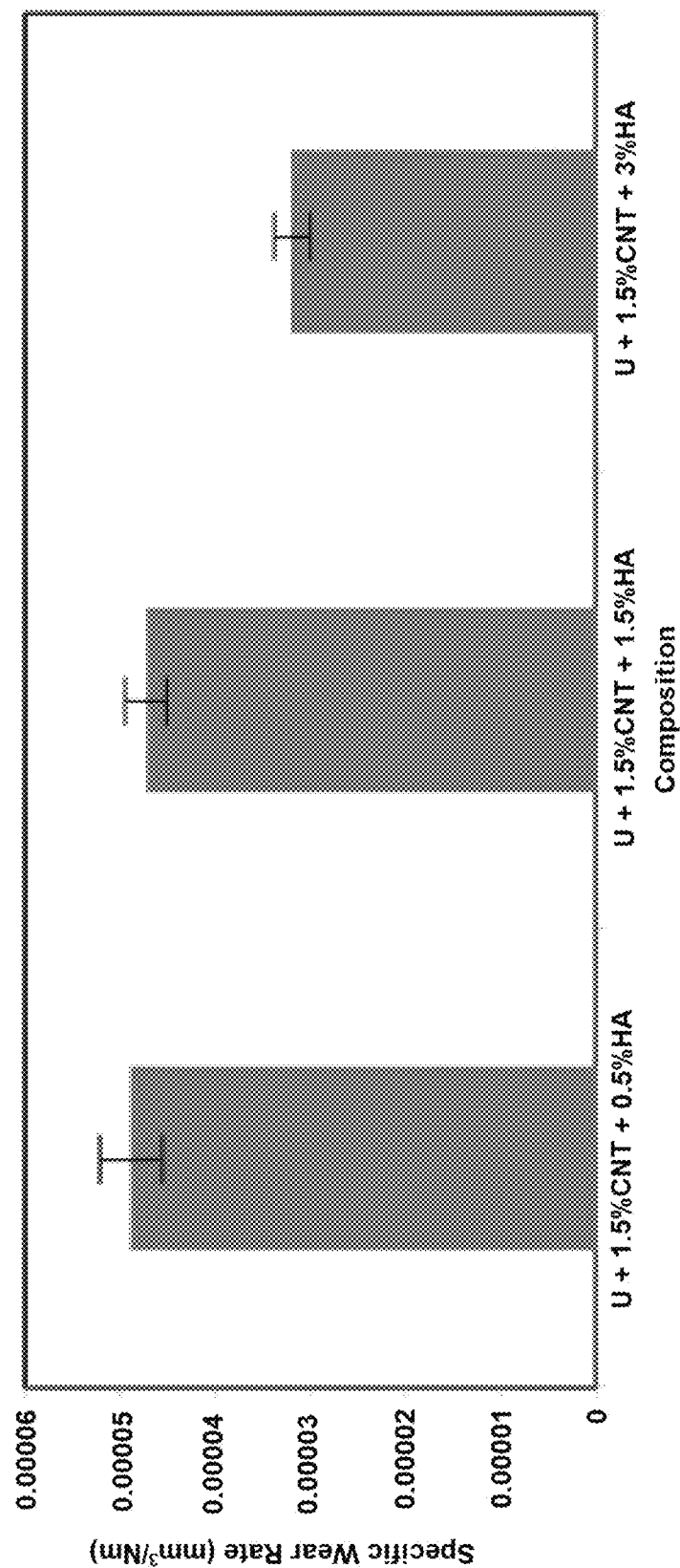
FIG. 11A shows a chart presenting the specific wear rate as a function of normal load of a substrate coated with UHMWPE comprising 1.5 wt. % CNT and different amounts of HA.
Figure 11B:
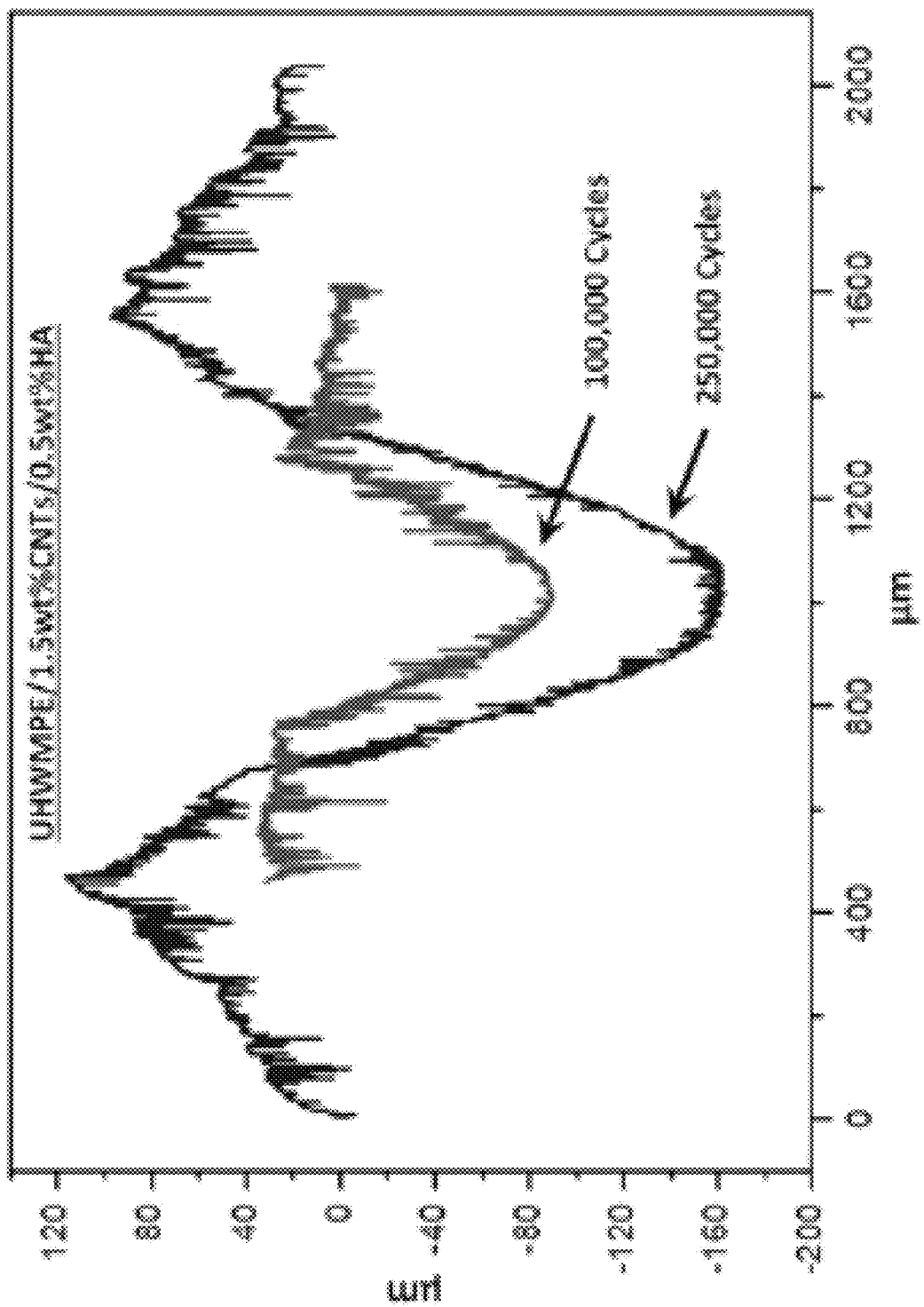
FIG. 11B shows 2D profiles of coatings comprising UHMWPE, 1.5 wt. % of CNTs, and 0.5 wt. % of HA, recorded at a tribological test conducted for 100,000 cycles and 250,000 cycles to evaluate the difference in track depth.
Figure 11C:
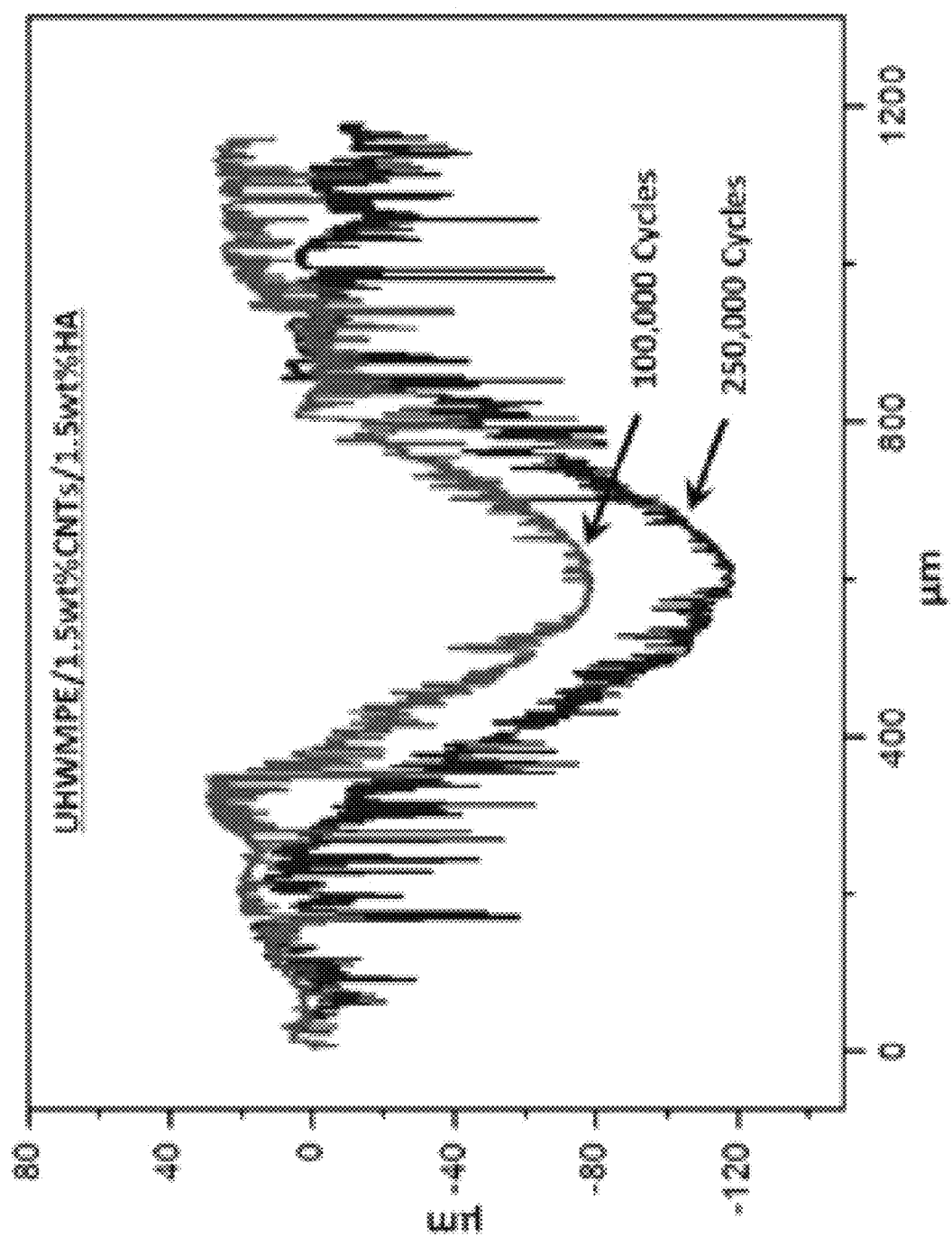
FIG. 11C shows 2D profiles of coatings comprising UHMWPE, 1.5 wt. % of CNTs, and 1.5 wt. % of HA, recorded at a tribological test conducted for 100,000 cycles and 250,000 cycles to evaluate the difference in track depth.
Figure 11D:
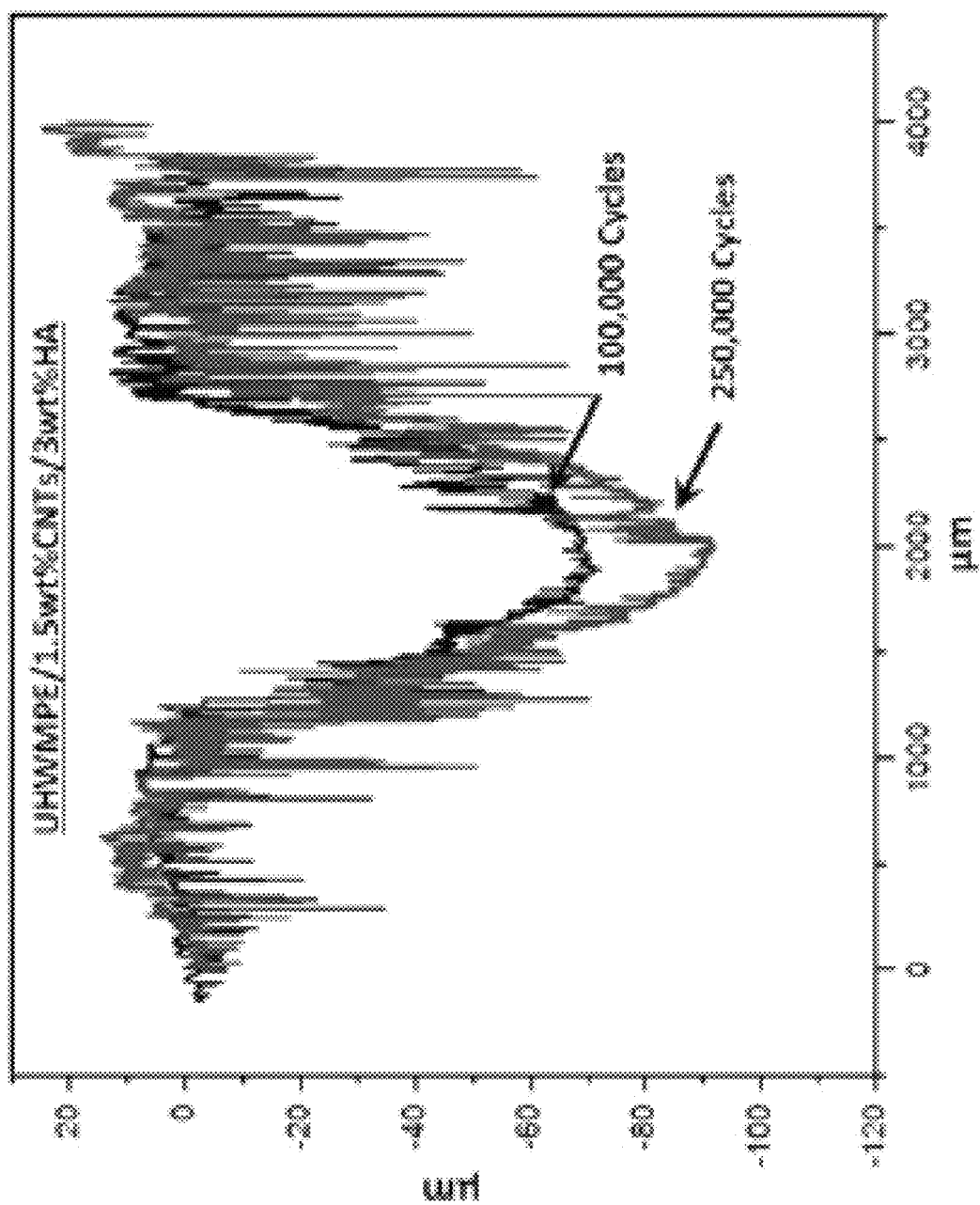
FIG. 11D shows 2D profiles of coatings comprising UHMWPE, 1.5 wt. % of CNTs, and 3 wt. % of HA, recorded at a tribological test conducted for 100,000 cycles and 250,000 cycles to evaluate the difference in track depth.

FIG. 9A shows that the UHMWPE/1.5 wt % CNT coating failed earlier at an average wear life of ~170,000 cycles, though the nanocomposite coatings with 0.5, 1.5, and 3 wt. % of HA completed the 250,000 cycle test without failure. The 3-D profiles, 2-D profiles, and counterface ball images of a typical tests are shown in FIGS. 10B to 10D, 10F to 10H, and 10J to 10L. The endurance of the UHMWPE/1.5 wt % CNT coatings with loadings of 0.5, 1.5 and 3 wt. % of HA through the 100,000 cycle wear test prompted a 250,000 cycle wear test, to evaluate the change in the wear depth and individual wear resistances. FIG. 11B to 11D show comparisons of 2D wear track profiles for all the three compositions after wear 100,000 and 250,000 cycle tests for UHMWPE/1.5 wt % CNT/0.5 wt % HA (FIG. 11B), UHMWPE/1.5 wt % CNT/1.5 wt % HA (FIG. 11C), and UHMWPE/1.5 wt % CNT/3 wt % HA (FIG. 11D) coatings.

An increase in the HA content from 0.5 to 3 wt. % was observed to decrease the wear depth 75.7% to 39.2% upon increasing the tests from 100,000 cycles to 250,000 cycles for. Furthermore, a 70.7% and 42% increase in wear volume was observed for 0.5 and 3 wt. % HA upon increasing the test from 100,000 cycles to 250,000 cycles. Specific wear rates were calculated as shown in FIG. 11A. The coating with 3 wt. % HA was observed to have the lowest specific wear rate, indicating the 3 wt. % HA as a more wear resistant coating compared to 0.5 and 1.5 wt. %.

Tribological Characterization of Coating on Ti6Al4V Alloy

Figure 12A:
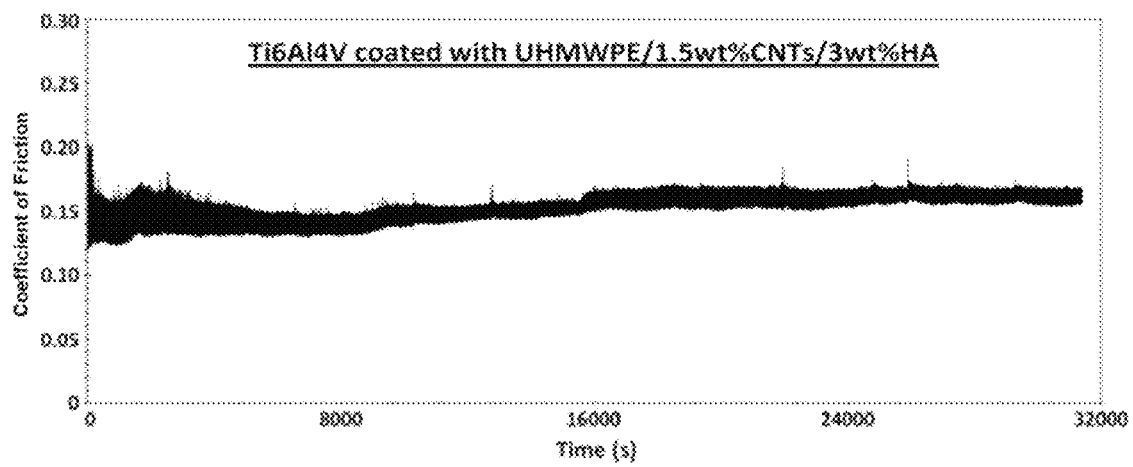
FIG. 12A to 12C show the COF graph, SEM image of the wear track, and EDX spectrum of a sample of the same type as shown in FIG. 8B wherein the substrate is Ti6Al4V rather than pure Ti.
Figure 12B:
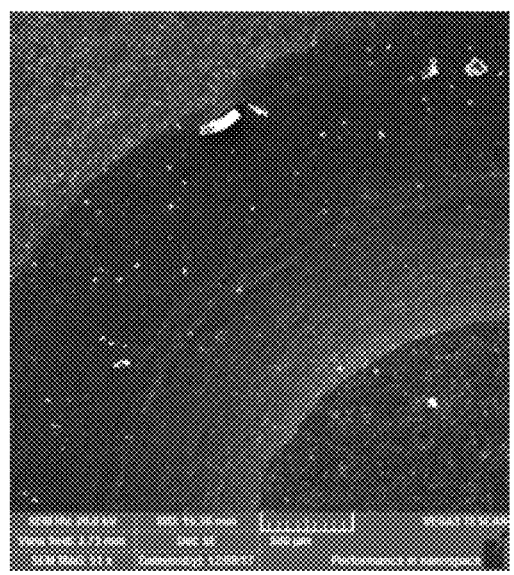
Figure 12C:
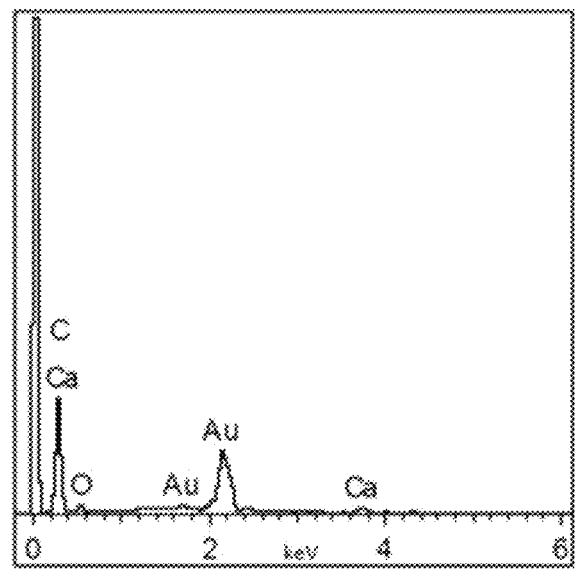

The UHMWPE/1.5 wt % CNTs/3 wt % HA coating was deposited on a Ti6Al4V alloy to study the effect of substrate on the tribological performance of the hybrid coating. Three samples of Ti6Al4V were coated with UHMWPE reinforced with 1.5 wt. % CNT and 3 wt. % HA and tribologically characterized using the same test parameters as above, i.e., a normal load of 12 N and a sliding speed of 0.1 m/s. No substrate effect was observed. The coating completed the 250,000 cycle test without failure for all the three tests. FIG. 12 shows the coefficient of friction (COF) graph along with the wear track and EDX analysis for one of the tested samples.

Hardness Evaluation of Coatings

Figure 13:
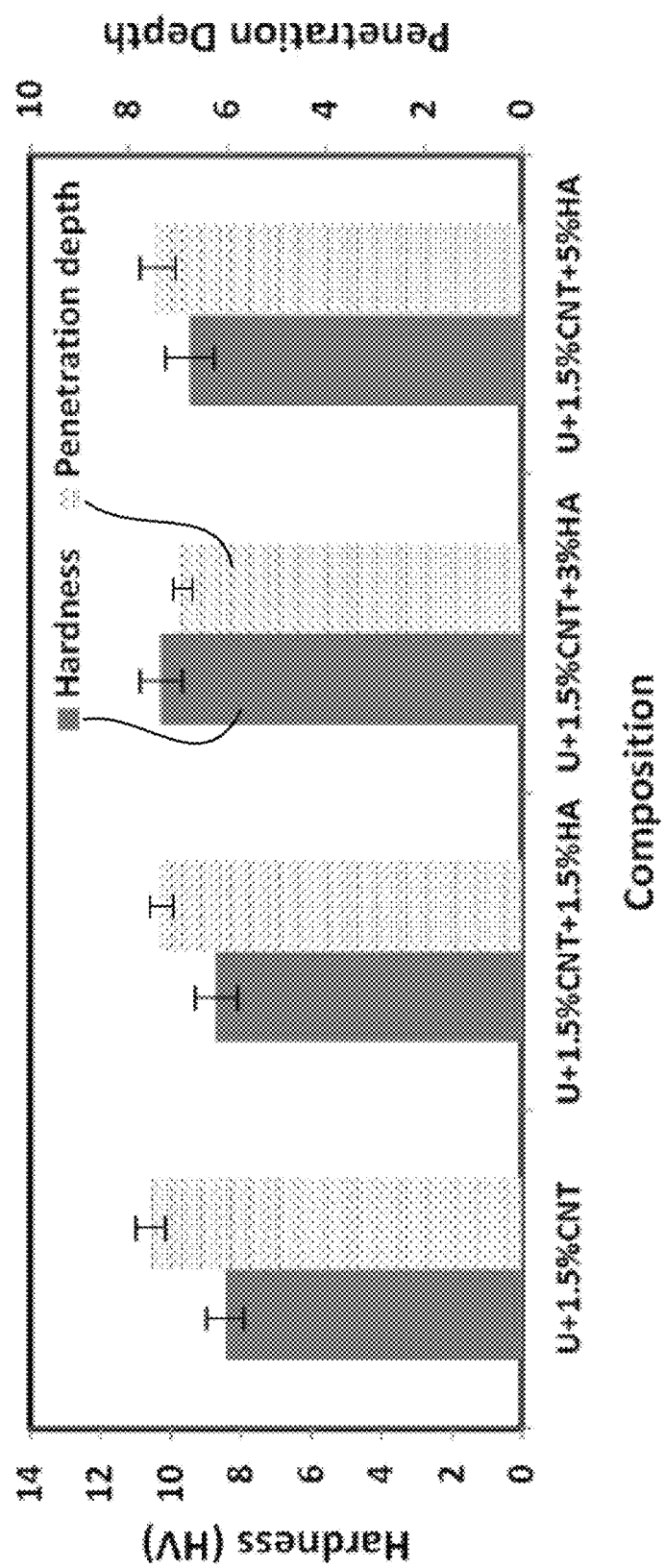
FIG. 13 shows a chart of Vickers hardness and penetration depth for coating compositions comprising UHMWPE and 1.5 wt. % of CNTs (leftmost), UHMWPE, 1.5 wt. % of CNTs, and 1.5 wt. % of HA ($2^{nd}$ from left), UHMWPE, 1.5 wt. % of CNTs, and 3 wt. % of HA ($2^{nd}$ from right), and UHMWPE, 1.5 wt. % of CNTs, and 5 wt. % of HA (rightmost)

FIG. 13 shows the change in hardness and penetration depth for different compositions of HA added to UHMWPE reinforced with 1.5 wt. % CNTs. A 22.1% increase (e.g., at least 17.5, 18, 19, 20, 21, 22, 22.5, 23, 24, 25%, or more) in the hardness value and a 9% decrease (e.g., at least 5, 6, 6.67, 7, 7.5, 8, 8.5, 9. 9.5, 10, 10.5, 11, 11.5, 12, 12.5% or greater) in penetration depth is observed for 0 to 3 wt. % HA. The hardness and penetration depth was calculated from the average of 20 different indentations made at different locations on the sample. The improved tribological performance for 3 wt. % HA may be attributed to the increase in harness. A drop in the hardness value and an increase in penetration depth was observed for 5 wt % HA this could be due to agglomerations of HA plates as seen during SEM analysis.

Evaluation of Coating Scratch Resistance

Linear scratch tests were conducted on pure UHMWPE, UHMWPE reinforced with 1.5 wt. % CNT, and UHMWPE reinforced with 1.5 wt. % CNT and 3 wt. % HA coatings.

Figure 14A:
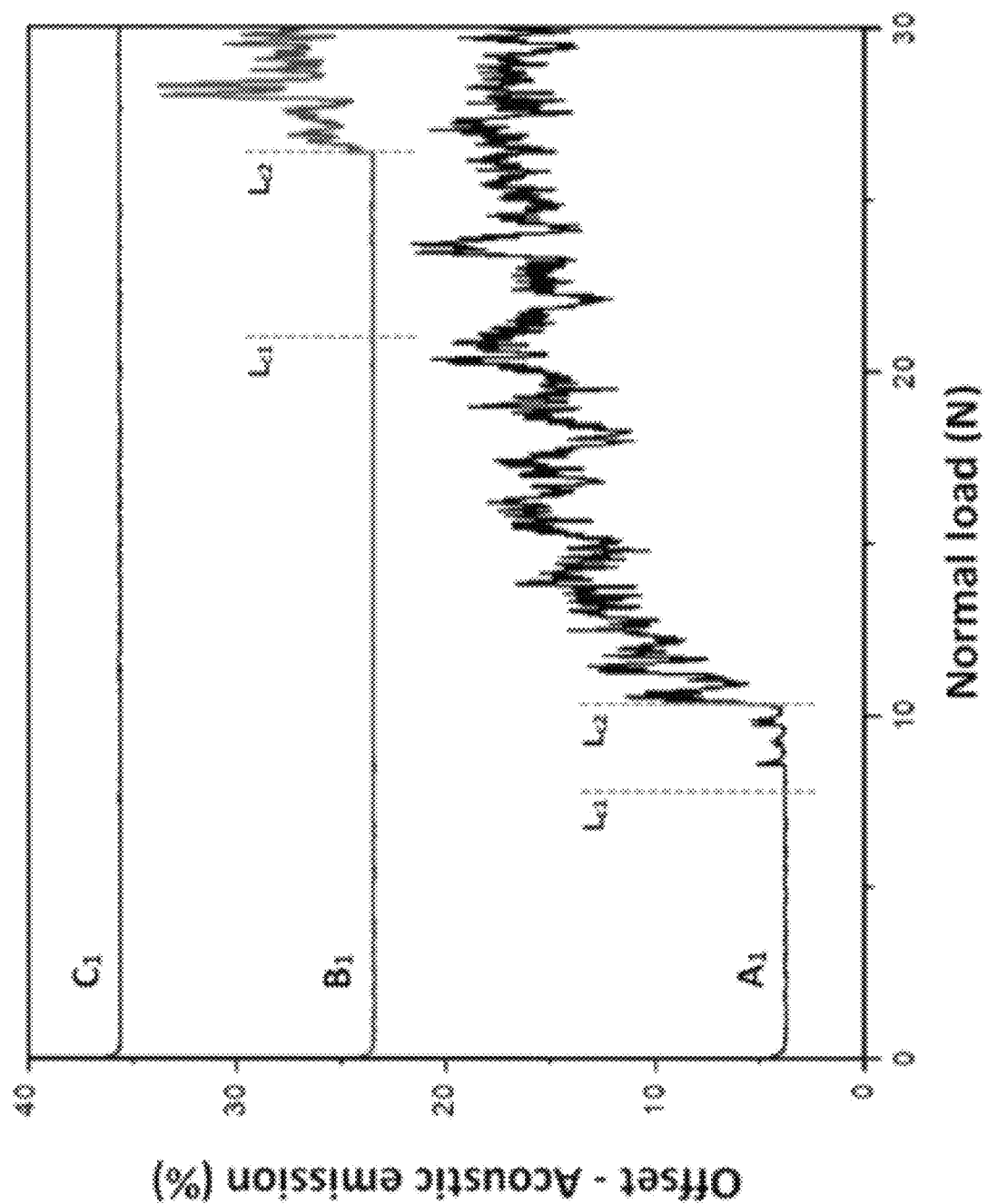
FIG. 14A shows an acoustic emission plot with respect to the applied normal load from 0 to 30 N for coatings comprising pure UHMWPE ($A_1$), UHMWPE and 1.5 wt. % CNTs ($B_1$), and UHMWPE, 1.5 wt. % CNTs, and 3 wt. % HA ($C_1$)
Figure 14D:
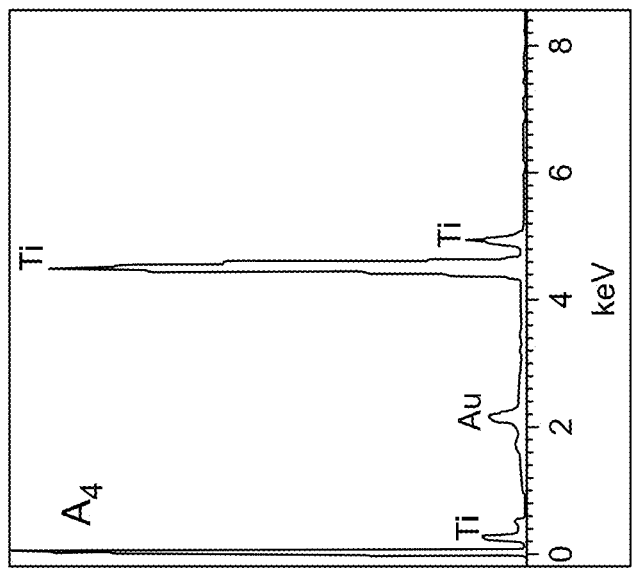
FIG. 14D shows an EDX spectrum for a coating comprising pure UHMWPE ($A_4$) after wear testing.
Figure 14C:
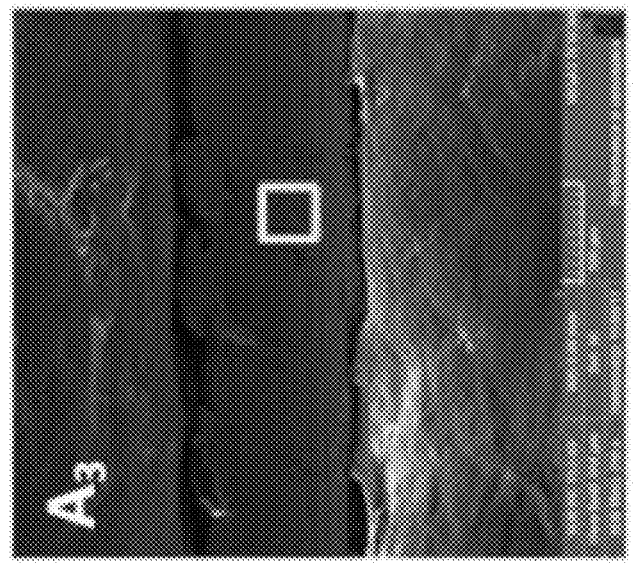
FIGS. 14B and 14C show SEM images of scratching for a coating comprising pure UHMWPE ($A_2$ and $A_3$) after wear testing.
Figure 14B:
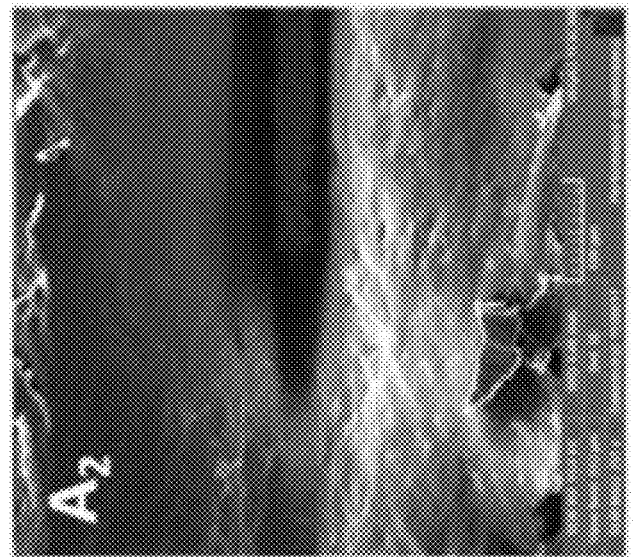

FIG. 14A shows the acoustic emission ($A_1$) with respect to the applied normal load for pure UHMWPE coated on pure titanium, wherein $L_{c1}$ represents the initial load at failure, and $L_{c2}$ represents the complete/ultimate load at failure. At an average load of ~7.3 N, the failure begins to occurs and the diamond tip penetrates the coating, as seen in the SEM image in FIG. 14H. Complete failure of the coating occurred at a load of ~10.2 N, with considerable peeling off and plowing observed and clear signs of plastic deformation along the edges of the scratch, as seen in the SEM images in FIG. 14I and EDX spectrum in FIG. 14J indicates the exposure of titanium.

Figure 14G:
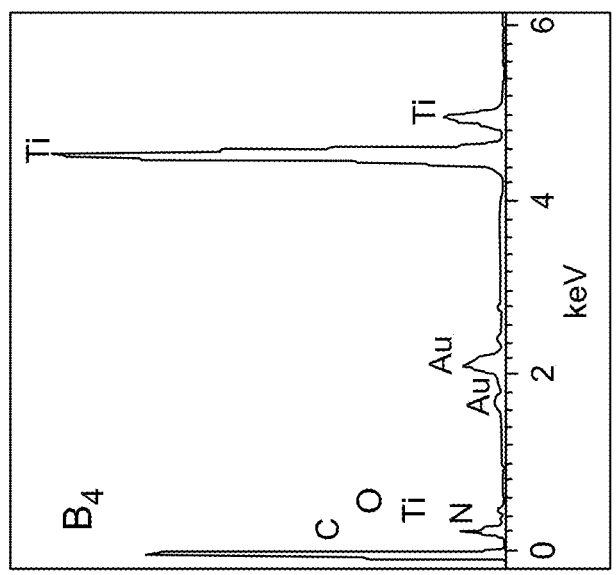
FIG. 14G shows an EDX spectrum for a coating comprising UHMWPE and 1.5 wt. % CNTs ($B_4$) after wear testing.
Figure 14F:
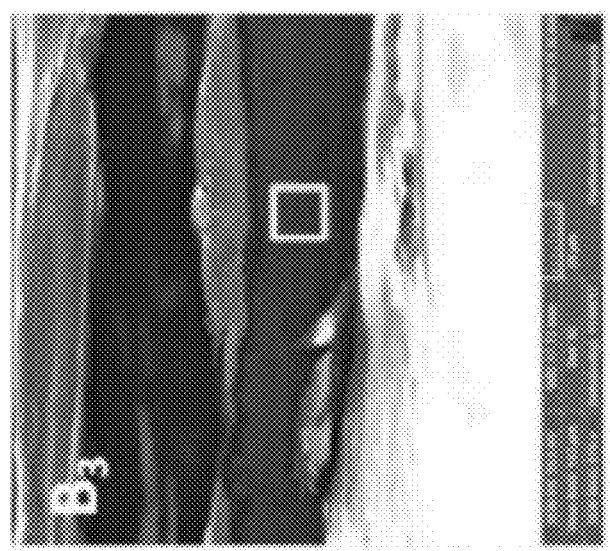
FIGS. 14E and 14F show SEM images of scratching for a coating comprising UHMWPE and 1.5 wt. % CNTs ($B_2$ and $B_3$) after wear testing.
Figure 14E:
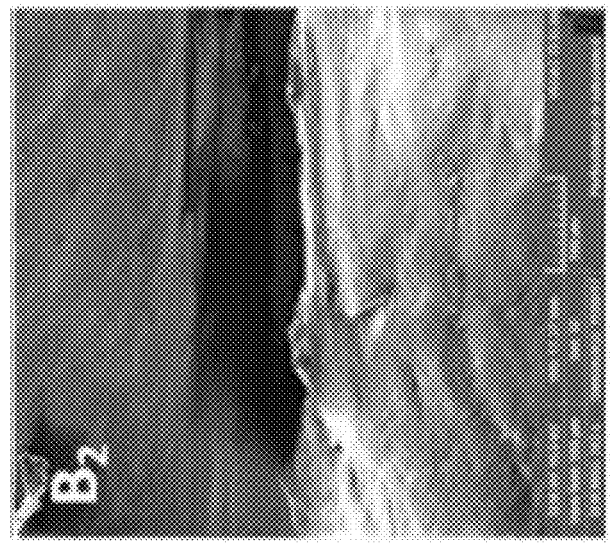
Figure 14J:
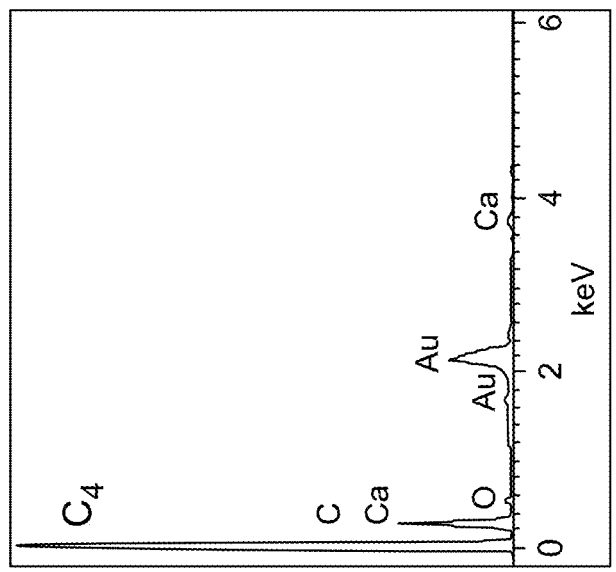
FIG. 14J shows an EDX spectrum for a coating comprising UHMWPE, 1.5 wt. % CNTs, and 3 wt. % HA ($C_4$) after wear testing.
Figure 14I:
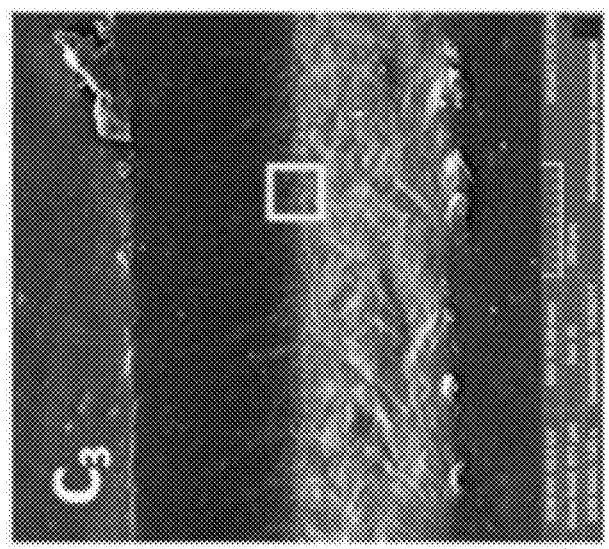
FIGS. 14H and 14I show SEM images of scratching for a coating comprising UHMWPE, 1.5 wt. % CNTs, and 3 wt. % HA ($C_2$ and $C_3$) after wear testing.
Figure 14H:
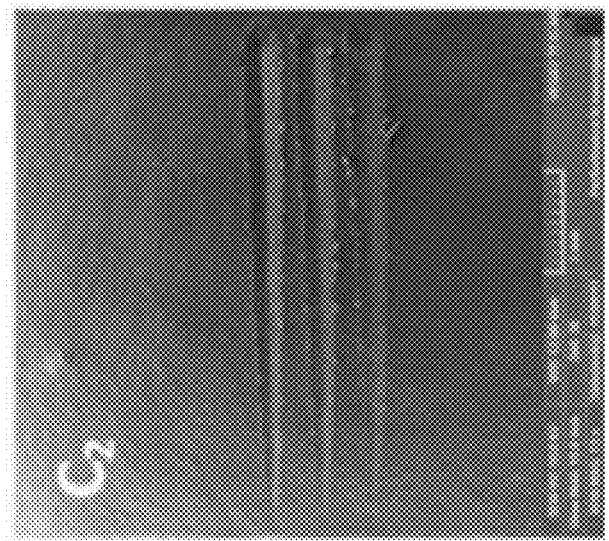

The coating comprising UHMWPE reinforced with 1.5 wt. % CNT initially failed at an average normal load of 21.8 N and reached complete failure at an average normal load of 26.4 N, as seen in FIG. 13 ($B_1$). FIG. 13 ($B_1$) shows an increase in the scratch resistance of the nanocomposite coating as compared to pure UHMWPE, indicating that the addition of CNTs improves the adhesive strength/scratch resistance of the coating. FIG. 14E to 14G show two SEM images along with an EDX analysis at the location of the failure.

The coating comprising UHMWPE reinforced with 1.5 wt. % CNT and 3 wt. % HA did not fail during a linear progressive scratch test, as shown in FIG. 13 ($C_1$). Its acoustic emission remains constant throughout the test indicating the indenter not being able to penetrate the coating until a normal load of 30N implying a very adhesive and a scratch resistant coating. FIG. 14B shows the full length of the scratch and FIG. 14C shows a location of the scratch at ~29N normal load.

Tribological Performance Comparison

Figure 15A:
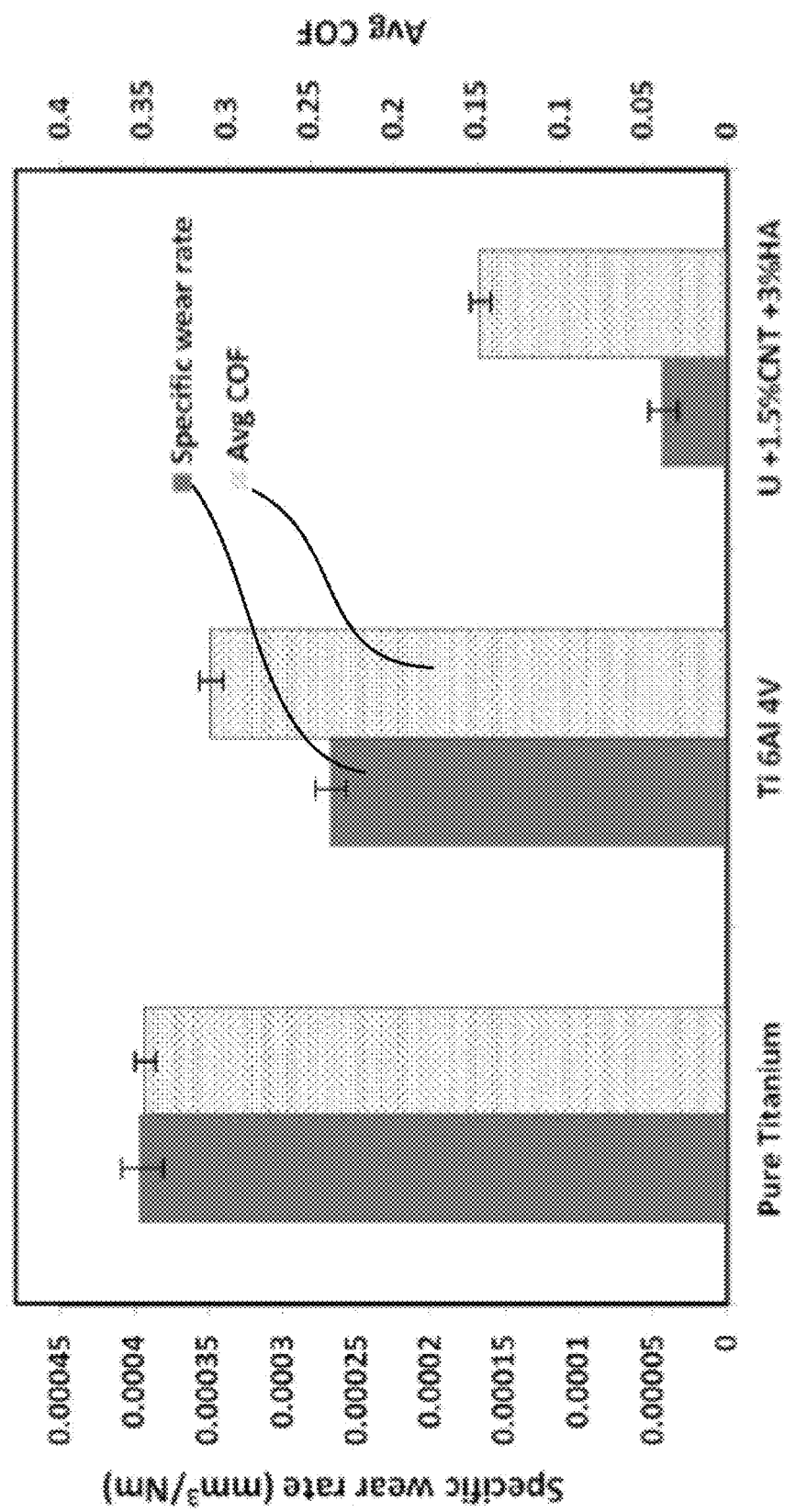
FIG. 15A shows a chart of specific wear rates and average coefficients of friction for bare substrates and a pure Ti substrate with a coating comprising UHMWPE, 1.5 wt. % CNTs, and 3 wt. % HA tested under at a normal load of 12N and a sliding velocity of 0.1 m/s.

The specific wear rate (SWR) and coefficient of friction (COF) of inventive coatings were compared to those of the bare substrates to investigate the efficiency of the inventive coatings in improving the wear life of the substrates and in protecting the substrates from wear and tear. Specific wear rates (SWR) were calculated for the bare substrates and the exemplary UHMWPE coating comprising 1.5 wt. % CNT and 3 wt. % HA. As illustrated in FIG. 15A, the exemplary inventive coating had a lower SWR and lower COF relative to the uncoated substrates.

Figure 15B:
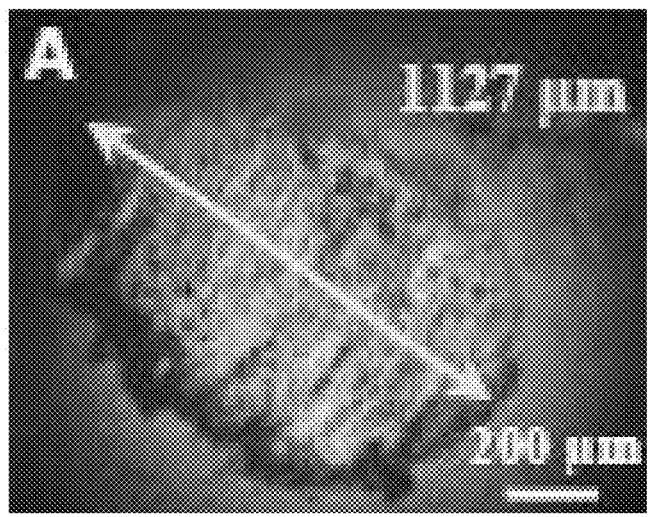
FIG. 15B to 15D show SEM images for the ball countersurfaces of the bare substrates and the coated substrate from FIG. 15A.
Figure 15C:
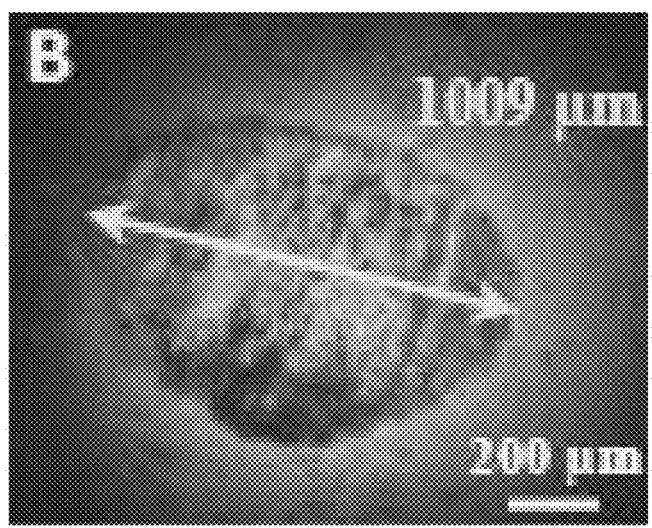
Figure 15D:
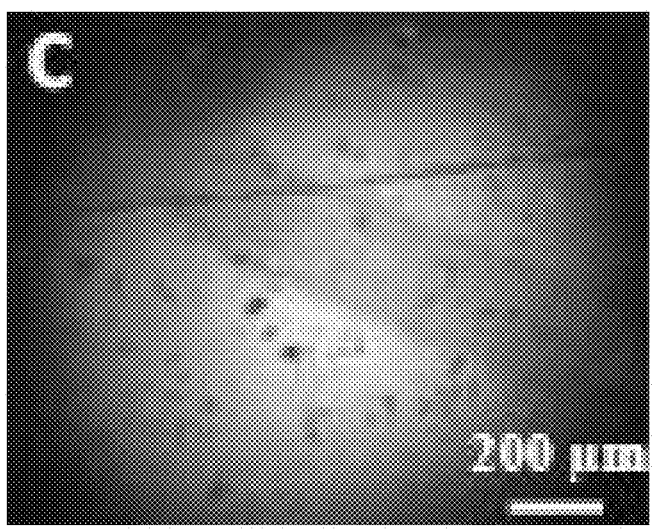

In tribological application, the wear life of both the mating surfaces is relevant. Coatings and/or surface modifications done to improve the tribological properties of one of the mating surfaces should ideally be able to protect even the counterface material from wear, as is generally the case for inventive coatings. As seen in FIG. 15A, the specific wear rate and the COF for the exemplary inventive coatings is lower than the bare substrates. In addition, even the counterface ball, slid against the exemplary inventive coatings shows no (or few) signs of wear, based on the optical image of the ball in FIG. 15D. FIG. 15D was recorded after a 250,000 cycle test, indicating improved tribological performance of the coating in protecting the complete system, i.e., coated surface and uncoated, countersurface. FIGS. 15B and 15C show, however, that the ball countersurface, slid against the bare Ti substrates, scarred after 2400 cycles of a test run. Thus, exemplary inventive coatings can reduce the COF and SWR of the titanium alloys, as well as the countersurface.

Surface Corrosion Test

Figure 16A:
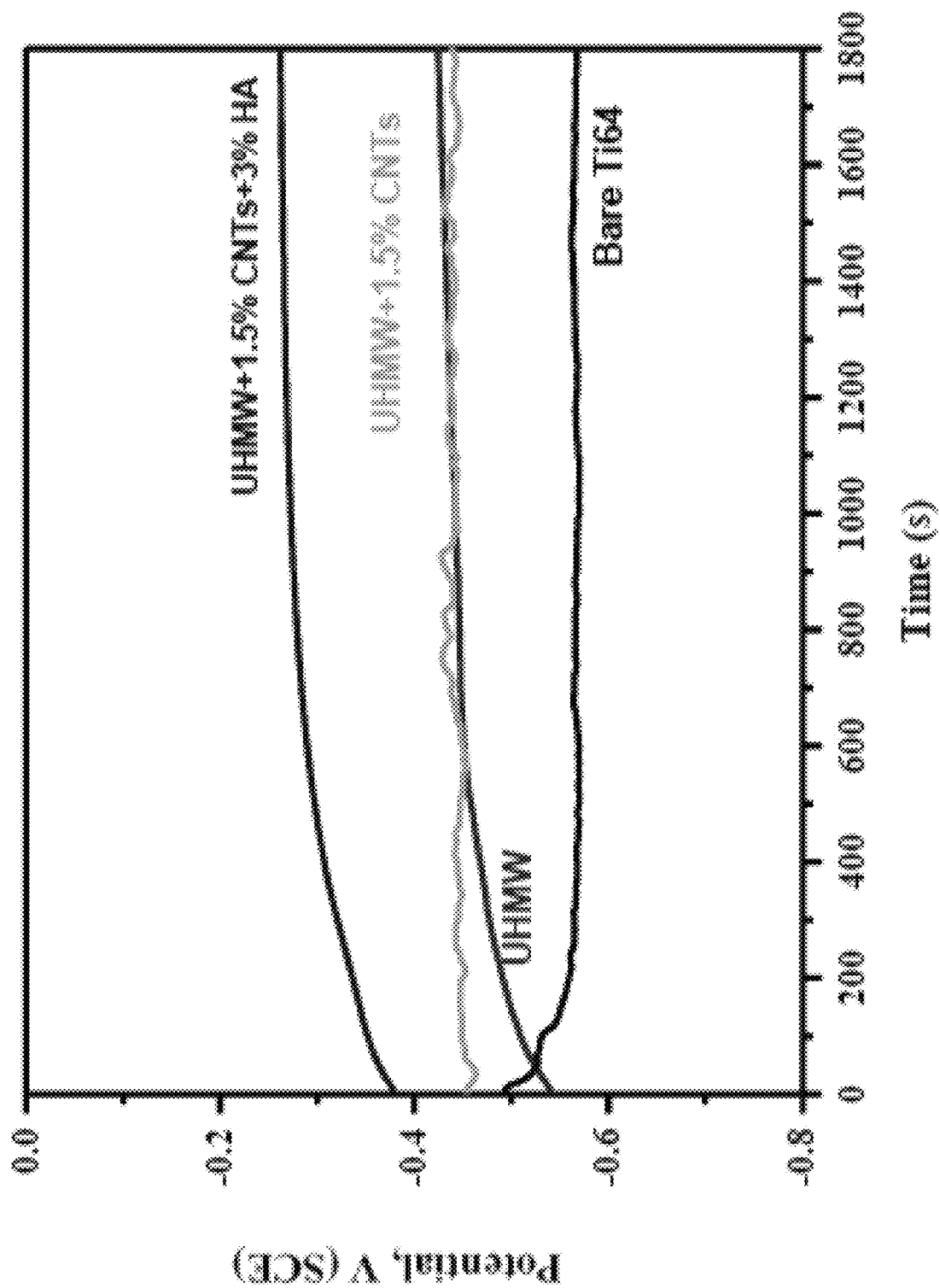
FIG. 16A shows plots monitoring of open circuit potential values over time for bare and coated substrates.

FIG. 16A shows the monitoring of open circuit potential (OCP) values for uncoated and coated Ti6aAl4V alloy samples in simulated body fluid (SBF) medium. Uncoated Ti6Al4V sample required approx. 400 seconds to reach approx. −542 mV against a saturated calomel electrode (SCE), after which approx. 400 seconds the OCP value stabilized, representing the stabilization of the passive layer. The OCP of coated samples increases more quickly with the time at the initial 500 seconds, demonstrating compact coating, and then maintains a higher steady value. The OCP value of Ti6Al4V coated with UHMW(PE) including 1.5 wt. % CNT and optionally further 3 wt. % HA shifted in the noble direction, i.e., more positively, with the UHMWPE coating comprising 1.5 wt. % CNT and 3 wt. % HA exhibiting the noblest shift in potential. Such positive-shift behavior indicates an enhanced corrosion protection performance of UHMWPE coatings incorporating 1.5 wt. % CNTs and/or 3 wt. % HA.

Figure 16B:
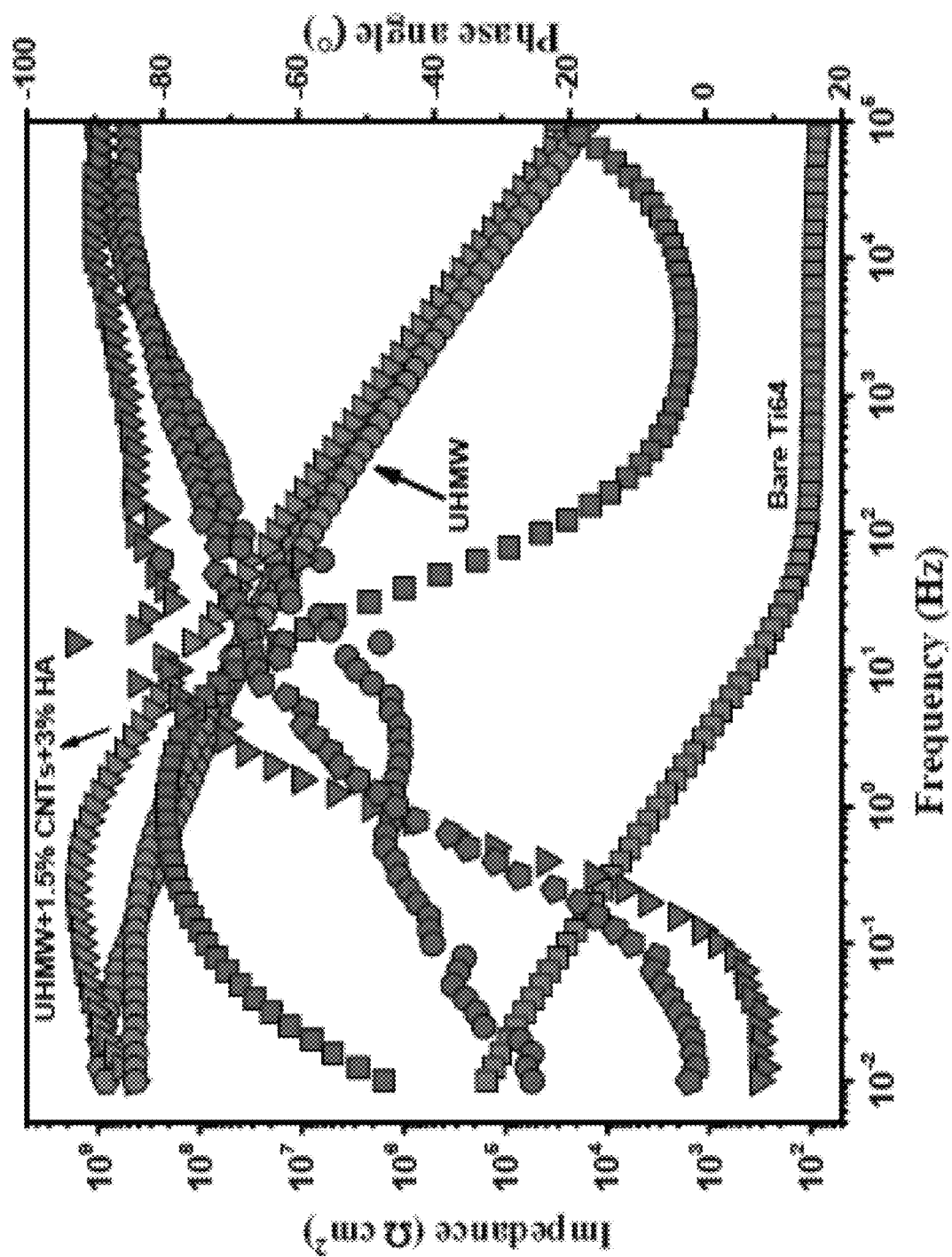
FIG. 16B shows electrochemical impedance spectroscopy plots of impedance values and phase angles versus frequency for bare and coated substrates.

FIG. 16B shows electrochemical impedance spectroscopic (EIS) data in Bode formats. In the Bode graphs, all of the coated samples suggest different EIS curves from each other and the uncoated Ti6Al4V.

For uncoated substrates, a large phase angle continued about −80° at mid and low-frequency regions while the slope of resistant curves was found to be about −1, indicating a distinctive result of a capacitive behavior of native passive layer. In contrast, two maxima in phase angles were obtained at the high and low-frequency regions in the case of coated Ti6Al4V samples, revealing the association of at least two-time constants related with the two-layer structure of the coated Ti6Al4V samples.

In particular, the coatings incorporating 1.5 wt. % CNTs and 3 wt. % HA exhibited the highest impedance values, indicating improved protective behavior of the coatings. In general, in Bode plots, a higher impedance modulus (Z) at a lower frequency region indicates a higher corrosion resistance of a metal substrate, as described in *Electrochim. Acta* 2012, 69, 287-294, which is incorporated by reference herein in its entirety. The impedance in the low-frequency region for the coated Ti6Al4V substrates appears to be nearly four orders of magnitude higher than that shown by the uncoated Ti6Al4V substrate. The higher impedance is possibly due to a barrier performance where the coating obstructs admission of hostile electrolytic species to the metal/coating interface.

Quantitative analysis of EIS data generally requires fitting with an accurate equivalent circuit model. Thus, an equivalent circuit with two-time constants was utilized to analyze the obtained EIS curves of the coated specimens, as described in *RSC Adv.* 2015, 5, 96601-96610, and *Prog. Org. Coatings* 2015, 86, 41-48, each of which is incorporated by reference herein in its entirety.

The fitted equivalent circuit model can be denoted as $R_s$ ($R_{ct}Q_1$) ($R_fQ_2$), which contains two combinations of resistors and capacitors with the solution resistance, wherein $R_s$ signifies the solution resistance, related to systemic ohmic resistance, $R_{ct}$ represents the charge transfer resistance, $R_f$ represents the film resistance, $Q_1$ represents the capacitance of the double layer, and $Q_2$ represents the capacitance of the film. A constant phase element (CPE) is used instead of a pure capacitance since ideal capacitive behavior is not observed in real solutions. In addition, using a constant phase element reduces error and provides more detailed information about the non-ideal dielectric properties of the coating. The CPE in the current work was calculated using the following Equation 2, below, based on *Prog. Org. Coatings* 2015, 86, 41-48, and *Carbohydr. Polym.* 2017, 173, 121-130, each of which is incorporated by reference herein in its entirety.

$$Z = Y_0^{-1}(j\Omega)^{-n} \qquad \text{Eq. 2.}$$

In Equation 2, Z is the CPE, ω is the angular frequency (2πf), Y is a proportionality factor, n is the deviation parameter related to the surface roughness, n is 1 for an ideal capacitor wherein $Q_1=C_{dl}$, and j is current.

The Ra value for the Ti6Al4V substrates with coatings increased from 151.26 kΩ/cm² for bare (uncoated) to 422.35 kΩ/cm² for the UHMWPE, 853.25 kΩ/cm² for UHMWPE including 1.5 wt. % CNTs, and 914.54 kΩ/cm² for UHMWPE including 1.5 wt. % CNTs and 3 wt. % HA, indicating improved anticorrosion behavior. Generally, $R_f$ values may be influenced by the number of pores/capillary networks in the coatings surface, through which the hostile species from the solution spread to the metal-coating interface. The highest $R_f$ value of 1.18 GΩ cm² was obtained for the Ti6Al4V coated with UHMWPE including 1.5 wt. % CNTs and 3 wt. % HA, indicating that this is the least porous coating.

Hence, the inclusion of nanocomposite in the UHMW matrix appears to reduce the porosity of the UHMW coatings by covering and/or sealing the micro cracks and voids inside the coating. The high impedance values determined can delay the diffusion/dissemination of hostile and/or caustic species, thereby improving the surface protective performance of the coatings against corrosion. Increased $Q_1$ and $Q_2$ values may be associated with the diffusion of active species to the interface and/or expanding the delaminated area. Comparing the $Q_1$ and $Q_2$ values of the coated Ti6Al4V samples indicates that samples including 1.5 wt. % CNTs and 3 wt. % HA had the lowest $Q_1$ ($1.5\times10^{-3}$ μF/cm$^2$) and $Q_2$ values ($8.6\times10^{-3}$ μF/cm$^2$), indicating that the 1.5 wt. % CNTs with 3 wt. % HA coating retained a stable coating/metal interface devoid of any corrosion. Based on the electrochemical results, it can be revealed that the UHMWPE coatings including 1.5 wt. % CNTs with 3 wt. % HA exhibit the better corrosion protection performance than pure UHMWPE and uncoated Ti6Al4V sample in SBF medium.

Numerous modifications and variations of the present invention are possible in light of the above teachings. It is therefore to be understood that within the scope of the appended claims, the invention may be practiced otherwise than as specifically described herein.

The invention claimed is:

1. An article, comprising:
   a metallic substrate; and
   a coating directly contacting the metallic substrate, the coating comprising:
   a polymer matrix of at least 75 wt. % ultra high molecular weight polyethylene;
   from 0.5 to 4.75 wt. % of platelets of hydroxyapatite; and
   from 0.5 to 2.75 wt. % carbon nanotubes;
   wherein
   the platelets of hydroxyapatite and carbon nanotubes are uniformly dispersed in the polymer matrix,
   the metallic substrate comprises at least one metal selected from the group consisting of elemental titanium, gold, cobalt, tantalum, chromium, nickel, and stainless steel,
   a specific surface area of the carbon nanotubes is from 60 m$^2$/g to 70 m$^2$/g, and
   the coating has a thickness of between 60 and 1000 μm.

2. The article of claim 1, wherein the metallic substrate comprises at least 75 wt. % pure titanium or Ti6Al4V, based upon total substrate weight.

3. The article of claim 1, wherein the metallic substrate is pure titanium.

4. The article of claim 1, wherein the metallic substrate is Ti6Al4V.

5. The article of claim 1, wherein the coating comprises the carbon nanotubes in a range of from 1 to 2 wt. % and the hydroxyapatite platelets in a range of from 2.5 to 3.5 wt. %.

6. The article of claim 1, wherein the coating comprises the ultra high molecular weight polyethylene in an amount of at least 97.5 wt. %, relative to all polymer content in the coating.

7. The article of claim 1, wherein the ultra high molecular weight polyethylene has a Mn of at least 1,000,000 g/mol.

8. The article of claim 1, wherein the coating has a thickness of from 100 μm to 1000 μm.

9. The article of claim 1, wherein the carbon nanotubes have
   an outer diameter in a range of from 40 to 60 nm, and
   a length in a range of from 1 to 2 μm.

10. The article of claim 1, wherein the carbon nanotubes are multi-walled.

11. The article of claim 1, having a Vickers hardness on a surface of the coating opposite the substrate of at least 8.

12. A method for preparing the article of claim 1, comprising:
    pretreating the metallic substrate including contacting the substrate with plasma, to obtain a pretreated metallic substrate; and
    electrospraying onto the pretreated metallic substrate a powder comprising at least 75 wt. % of ultra high molecular weight polyethylene, 0.5 to 4.75 wt. % of hydroxyapatite platelets, and 0.5 to 2.75 wt. % of carbon nanotubes, to obtain the coated substrate.

13. The method of claim 12, further comprising, after the contacting, heating the metallic substrate contacted with plasma to at least 140° C., to obtain a pretreated substrate.

14. The method of claim 13, further comprising,
    heating the electrosprayed coated substrate to at least 140° C.

15. The article of claim 1, wherein the coating consists of the ultra high molecular weight polyethylene, the carbon nanotubes and the hydroxyapatite platelets, and wherein the coating contains the carbon nanotubes in a range of from 1 to 2 wt,% and the hydroxyapatite platelets in a range of from 2.5 to 3.5 wt. %; and
    wherein the metallic substrate comprises at least 75 wt. % pure titanium or Ti6Al4V.

* * * * *